US010856984B2

(12) United States Patent
Lane et al.

(10) Patent No.: US 10,856,984 B2
(45) Date of Patent: Dec. 8, 2020

(54) SEQUENTIALLY DEPLOYED TRANSCATHETER MITRAL VALVE PROSTHESIS

(71) Applicant: Neovasc Tiara Inc., Richmond (CA)

(72) Inventors: Randy Matthew Lane, Langley (CA);
Colin A. Nyuli, Vancouver (CA);
Alexei J. Marko, Vancouver (CA);
Krista L. Neale, Vancouver (CA)

(73) Assignee: Neovasc Tiara Inc., Richmond (CA)

( * ) Notice: Subject to any disclaimer, the term of this patent is extended or adjusted under 35 U.S.C. 154(b) by 258 days.

(21) Appl. No.: 16/111,898

(22) Filed: Aug. 24, 2018

(65) Prior Publication Data

US 2019/0060071 A1 Feb. 28, 2019

Related U.S. Application Data

(60) Provisional application No. 62/550,368, filed on Aug. 25, 2017.

(51) Int. Cl.
*A61F 2/24* (2006.01)

(52) U.S. Cl.
CPC ............ *A61F 2/2445* (2013.01); *A61F 2/243* (2013.01); *A61F 2/2418* (2013.01);
(Continued)

(58) Field of Classification Search
CPC ........ A61F 2/24; A61F 2/2403; A61F 2/2409; A61F 2/2412; A61F 2/2418; A61F 2/2427; A61F 2/243; A61F 2/2436; A61F 2/2439

See application file for complete search history.

(56) References Cited

U.S. PATENT DOCUMENTS 6,629,534 B1 10/2003 St. Goar et al.
8,449,599 B2 * 5/2013 Chau .................... A61F 2/2412
623/1.26
(Continued)

FOREIGN PATENT DOCUMENTS

CN 111263622 A 6/2020
DE 10103955 B4 11/2001
(Continued)

OTHER PUBLICATIONS

"International Application Serial No. PCT/CA2018/051019, International Search Report dated Nov. 19, 2018", 5 pgs.
(Continued)

*Primary Examiner* — Ryan J. Severson
(74) *Attorney, Agent, or Firm* — Schwegman Lundberg & Woessner, P.A.

(57) ABSTRACT

A sequentially deployed prosthetic cardiac valve includes a self-expanding frame having an atrial skirt, a ventricular skirt, and an annular region disposed therebetween. A first anterior tab is disposed on an anterior portion of the frame. A posterior tab is on a posterior portion of the self-expanding frame. The frame may be designed so that any portion may expand sequentially in any desired order. For example, a portion of the first anterior tab and a portion of the posterior tab may partially self-expand first. Next, the first anterior tab may fully self-expand before the posterior tab fully self-expands. The posterior tab may fully self-expand next followed by the ventricular skirt, or the ventricular skirt may self-expand next followed by full expansion of the posterior tab.

44 Claims, 51 Drawing Sheets

(52) U.S. Cl.
CPC .......... *A61F 2/2436* (2013.01); *A61F 2/2457* (2013.01); *A61F 2/2466* (2013.01); *A61F 2210/0014* (2013.01); *A61F 2220/0016* (2013.01); *A61F 2220/0075* (2013.01)

(56) References Cited

U.S. PATENT DOCUMENTS

| | | | |
|---|---|---|---|
| 8,579,964 B2 | 11/2013 | Lane et al. | |
| 9,125,738 B2 | 9/2015 | Figulla et al. | |
| 9,125,740 B2* | 9/2015 | Morriss | A61F 2/2403 |
| 9,241,790 B2* | 1/2016 | Lane | A61F 2/2412 |
| 9,248,014 B2* | 2/2016 | Lane | A61F 2/2409 |
| 9,308,087 B2 | 4/2016 | Lane et al. | |
| 9,439,763 B2* | 9/2016 | Geist | A61F 2/2418 |
| 9,522,062 B2* | 12/2016 | Tuval | A61F 2/2412 |
| 9,554,897 B2* | 1/2017 | Lane | A61F 2/2436 |
| 9,572,665 B2* | 2/2017 | Lane | A61F 2/2436 |
| 9,713,529 B2 | 7/2017 | Lane et al. | |
| 9,770,329 B2* | 9/2017 | Lane | A61F 2/2427 |
| 10,363,133 B2* | 7/2019 | Lane | A61F 2/2418 |
| 10,383,728 B2* | 8/2019 | Lane | A61N 1/362 |
| 10,433,952 B2* | 10/2019 | Lane | A61F 2/2409 |
| 10,449,042 B2* | 10/2019 | Lane | A61F 2/2427 |
| 10,537,422 B2* | 1/2020 | Lane | A61F 2/2403 |
| 10,583,002 B2* | 3/2020 | Lane | A61F 2/2418 |
| 10,631,984 B2* | 4/2020 | Nyuli | A61F 2/2436 |
| 2006/0241745 A1 | 10/2006 | Solem | |
| 2007/0016286 A1 | 1/2007 | Herrmann et al. | |
| 2011/0015731 A1 | 1/2011 | Carpentier et al. | |
| 2011/0208297 A1* | 8/2011 | Tuval | A61F 2/2418 623/2.17 |
| 2011/0208298 A1* | 8/2011 | Tuval | A61F 2/2418 623/2.17 |
| 2012/0078353 A1* | 3/2012 | Quadri | A61F 2/2418 623/2.11 |
| 2013/0190861 A1* | 7/2013 | Chau | A61F 2/2418 623/2.18 |
| 2013/0310928 A1 | 11/2013 | Morriss et al. | |
| 2014/0222136 A1 | 8/2014 | Geist et al. | |
| 2017/0281336 A1 | 10/2017 | Lane et al. | |
| 2017/0348100 A1 | 12/2017 | Lane et al. | |
| 2019/0060071 A1* | 2/2019 | Lane | A61F 2/2418 |

FOREIGN PATENT DOCUMENTS

| | | |
|---|---|---|
| DE | 10033858 B4 | 1/2002 |
| DE | 102005052628 A1 | 5/2007 |
| DE | 102006052564 B3 | 12/2007 |
| DE | 102006013113 B4 | 12/2008 |
| DE | 102008015781 B4 | 9/2011 |
| DE | 102010051632 B4 | 9/2013 |
| DE | 102005032974 B4 | 11/2013 |
| DE | 102005052628 B4 | 6/2014 |
| DE | 10301026 B4 | 10/2014 |
| DE | 212013000104 U1 | 11/2014 |
| DE | 102008012438 B4 | 12/2014 |
| DE | 102011107551 B4 | 5/2015 |
| DE | 102011054176 B4 | 2/2016 |
| DE | 102014114762 B3 | 3/2016 |
| DE | 102013208038 B4 | 9/2016 |
| DE | 102010012677 B4 | 8/2017 |
| DE | 202011110951 U1 | 10/2017 |
| DE | 202011110985 U1 | 12/2017 |
| DE | 202016105963 U1 | 1/2018 |
| DE | 10394350 B4 | 5/2018 |
| DE | 102009024648 B4 | 5/2018 |
| DE | 102015206098 B4 | 9/2018 |
| DE | 10065824 B4 | 10/2018 |
| DE | 202017104793 U1 | 11/2018 |
| DE | 102011106928 B4 | 2/2019 |
| DE | 202016008737 U1 | 4/2019 |
| DE | 102013205519 B4 | 5/2019 |
| DE | 102008014730 B4 | 7/2019 |
| DE | 102018102940 B4 | 10/2019 |
| DE | 102009009158 B4 | 11/2020 |
| EP | 1077072 B1 | 11/2003 |
| EP | 1140244 B1 | 11/2003 |
| EP | 1214106 B1 | 11/2003 |
| EP | 1143864 B1 | 2/2004 |
| EP | 1220651 B1 | 3/2004 |
| EP | 1265534 B1 | 6/2004 |
| EP | 1347785 B1 | 7/2004 |
| EP | 1245202 B1 | 8/2004 |
| EP | 1161204 B1 | 9/2004 |
| EP | 1266641 B1 | 10/2004 |
| EP | 1102567 B1 | 11/2004 |
| EP | 1117446 B1 | 11/2004 |
| EP | 1107710 B1 | 12/2004 |
| EP | 1121070 B1 | 12/2004 |
| EP | 1217966 B1 | 12/2004 |
| EP | 1233731 B1 | 12/2004 |
| EP | 1294318 B1 | 12/2004 |
| EP | 1237510 B1 | 1/2005 |
| EP | 1034753 B1 | 2/2005 |
| EP | 1259194 B1 | 2/2005 |
| EP | 1121069 B1 | 3/2005 |
| EP | 1143879 B1 | 3/2005 |
| EP | 1023879 B1 | 4/2005 |
| EP | 1339356 B1 | 4/2005 |
| EP | 1214022 B1 | 5/2005 |
| EP | 1318774 B1 | 5/2005 |
| EP | 1088529 B1 | 6/2005 |
| EP | 1171060 B1 | 6/2005 |
| EP | 1251803 B1 | 6/2005 |
| EP | 1259776 B1 | 6/2005 |
| EP | 1272123 B1 | 6/2005 |
| EP | 1049422 B1 | 7/2005 |
| EP | 1230901 B1 | 8/2005 |
| EP | 1335683 B1 | 8/2005 |
| EP | 1307246 B1 | 9/2005 |
| EP | 1267753 B1 | 10/2005 |
| EP | 1284688 B1 | 10/2005 |
| EP | 1343536 B1 | 10/2005 |
| EP | 1027020 B1 | 11/2005 |
| EP | 1152780 B1 | 11/2005 |
| EP | 1171059 B1 | 11/2005 |
| EP | 1237508 B1 | 11/2005 |
| EP | 1303234 B1 | 11/2005 |
| EP | 1328215 B1 | 11/2005 |
| EP | 1341487 B1 | 11/2005 |
| EP | 1392197 B1 | 11/2005 |
| EP | 1469797 B1 | 11/2005 |
| EP | 1255505 B1 | 12/2005 |
| EP | 1360942 B1 | 12/2005 |
| EP | 1322260 B1 | 1/2006 |
| EP | 1359870 B1 | 1/2006 |
| EP | 1237586 B1 | 2/2006 |
| EP | 1112043 B1 | 4/2006 |
| EP | 1309360 B1 | 4/2006 |
| EP | 1322259 B1 | 5/2006 |
| EP | 1124592 B1 | 6/2006 |
| EP | 1237516 B1 | 6/2006 |
| EP | 1098673 B1 | 7/2006 |
| EP | 1124591 B1 | 7/2006 |
| EP | 1083845 B1 | 8/2006 |
| EP | 1155666 B1 | 8/2006 |
| EP | 1463462 B1 | 8/2006 |
| EP | 1519695 B1 | 9/2006 |
| EP | 1444993 B1 | 10/2006 |
| EP | 1117350 B1 | 11/2006 |
| EP | 1212011 B1 | 11/2006 |
| EP | 1261294 B1 | 11/2006 |
| EP | 1318775 B1 | 11/2006 |
| EP | 1429690 B1 | 11/2006 |
| EP | 1173111 B1 | 12/2006 |
| EP | 1239795 B1 | 12/2006 |
| EP | 1299049 B1 | 12/2006 |
| EP | 1487382 B1 | 12/2006 |
| EP | 1112044 B1 | 1/2007 |
| EP | 1482997 B1 | 1/2007 |
| EP | 1117352 B1 | 2/2007 |
| EP | 1128849 B1 | 2/2007 |
| EP | 1392666 B1 | 2/2007 |

(56) References Cited

FOREIGN PATENT DOCUMENTS

| | | | |
|---|---|---|---|
| EP | 1474077 B1 | 2/2007 |
| EP | 1251805 B1 | 3/2007 |
| EP | 1117334 B1 | 4/2007 |
| EP | 1263484 B1 | 5/2007 |
| EP | 1313410 B1 | 5/2007 |
| EP | 1370200 B1 | 5/2007 |
| EP | 1560526 B1 | 6/2007 |
| EP | 1173117 B1 | 7/2007 |
| EP | 1434615 B1 | 7/2007 |
| EP | 1465546 B1 | 7/2007 |
| EP | 1499366 B1 | 7/2007 |
| EP | 1225948 B1 | 8/2007 |
| EP | 1519962 B1 | 9/2007 |
| EP | 1337285 B1 | 10/2007 |
| EP | 1112042 B1 | 11/2007 |
| EP | 1148821 B1 | 11/2007 |
| EP | 1143882 B1 | 12/2007 |
| EP | 1330189 B1 | 12/2007 |
| EP | 1489996 B1 | 12/2007 |
| EP | 1296618 B1 | 1/2008 |
| EP | 1401356 B1 | 1/2008 |
| EP | 1629795 B1 | 1/2008 |
| EP | 1128786 B1 | 2/2008 |
| EP | 1616532 B1 | 2/2008 |
| EP | 1289447 B1 | 3/2008 |
| EP | 1115353 B1 | 5/2008 |
| EP | 1330190 B1 | 5/2008 |
| EP | 1383448 B1 | 6/2008 |
| EP | 1251804 B1 | 7/2008 |
| EP | 1294310 B1 | 7/2008 |
| EP | 1313409 B1 | 7/2008 |
| EP | 1395202 B1 | 7/2008 |
| EP | 1395204 B1 | 7/2008 |
| EP | 1395205 B1 | 7/2008 |
| EP | 1423066 B1 | 7/2008 |
| EP | 1560545 B1 | 7/2008 |
| EP | 1605871 B1 | 7/2008 |
| EP | 1671608 B1 | 7/2008 |
| EP | 1690515 B1 | 7/2008 |
| EP | 1180987 B1 | 8/2008 |
| EP | 1337386 B1 | 8/2008 |
| EP | 1492579 B1 | 9/2008 |
| EP | 1524942 B1 | 9/2008 |
| EP | 1627091 B1 | 9/2008 |
| EP | 1827577 B1 | 9/2008 |
| EP | 1259195 B1 | 10/2008 |
| EP | 1704834 B1 | 10/2008 |
| EP | 1146835 B1 | 11/2008 |
| EP | 1498086 B1 | 11/2008 |
| EP | 1622548 B1 | 11/2008 |
| EP | 1235537 B1 | 12/2008 |
| EP | 1237509 B1 | 12/2008 |
| EP | 1355590 B1 | 12/2008 |
| EP | 1455680 B1 | 12/2008 |
| EP | 1472995 B1 | 12/2008 |
| EP | 1513474 B1 | 12/2008 |
| EP | 1562522 B1 | 12/2008 |
| EP | 1620042 B1 | 12/2008 |
| EP | 1690514 B1 | 12/2008 |
| EP | 1258232 B1 | 1/2009 |
| EP | 1420723 B1 | 1/2009 |
| EP | 1570809 B1 | 1/2009 |
| EP | 1395182 B1 | 2/2009 |
| EP | 1408882 B1 | 2/2009 |
| EP | 1482868 B1 | 2/2009 |
| EP | 1255510 B3 | 3/2009 |
| EP | 1330213 B1 | 3/2009 |
| EP | 1429651 B1 | 3/2009 |
| EP | 1610727 B1 | 4/2009 |
| EP | 1617788 B1 | 4/2009 |
| EP | 1634547 B1 | 4/2009 |
| EP | 1790318 B1 | 4/2009 |
| EP | 1250165 B1 | 5/2009 |
| EP | 1842508 B1 | 6/2009 |
| EP | 1968482 B1 | 6/2009 |
| EP | 1343438 B1 | 7/2009 |
| EP | 1406608 B1 | 7/2009 |
| EP | 1509256 B1 | 7/2009 |
| EP | 1626681 B1 | 7/2009 |
| EP | 1723935 B1 | 7/2009 |
| EP | 1803420 B1 | 7/2009 |
| EP | 1401359 B1 | 8/2009 |
| EP | 1411865 B1 | 8/2009 |
| EP | 1485033 B1 | 8/2009 |
| EP | 1581120 B1 | 8/2009 |
| EP | 1620040 B1 | 8/2009 |
| EP | 1684667 B1 | 8/2009 |
| EP | 1872743 B1 | 8/2009 |
| EP | 1100378 B1 | 9/2009 |
| EP | 1198203 B1 | 9/2009 |
| EP | 1370201 B1 | 9/2009 |
| EP | 1408850 B1 | 9/2009 |
| EP | 1472996 B1 | 9/2009 |
| EP | 1478364 B1 | 9/2009 |
| EP | 1653888 B1 | 9/2009 |
| EP | 1785154 B1 | 9/2009 |
| EP | 1881804 B1 | 9/2009 |
| EP | 1903991 B1 | 9/2009 |
| EP | 1418865 B1 | 10/2009 |
| EP | 1561437 B1 | 10/2009 |
| EP | 1615595 B1 | 10/2009 |
| EP | 1353612 B1 | 11/2009 |
| EP | 1348406 B1 | 12/2009 |
| EP | 1370202 B1 | 12/2009 |
| EP | 1603492 B1 | 12/2009 |
| EP | 1670364 B1 | 12/2009 |
| EP | 1759663 B1 | 12/2009 |
| EP | 1994887 B1 | 12/2009 |
| EP | 1615593 B1 | 1/2010 |
| EP | 1643938 B1 | 1/2010 |
| EP | 1863402 B1 | 1/2010 |
| EP | 1943942 B1 | 1/2010 |
| EP | 2010101 B1 | 1/2010 |
| EP | 2081518 B1 | 1/2010 |
| EP | 1703865 B1 | 2/2010 |
| EP | 1276437 B1 | 3/2010 |
| EP | 1276439 B1 | 3/2010 |
| EP | 1411867 B1 | 3/2010 |
| EP | 1458301 B1 | 3/2010 |
| EP | 1520519 B1 | 3/2010 |
| EP | 1648340 B1 | 3/2010 |
| EP | 1682048 B1 | 3/2010 |
| EP | 1773239 B1 | 3/2010 |
| EP | 1935377 B1 | 3/2010 |
| EP | 1994912 B1 | 3/2010 |
| EP | 1154738 B1 | 4/2010 |
| EP | 1531762 B1 | 4/2010 |
| EP | 1600178 B1 | 4/2010 |
| EP | 1626682 B1 | 4/2010 |
| EP | 1511445 B1 | 5/2010 |
| EP | 1198213 B1 | 6/2010 |
| EP | 1250097 B1 | 6/2010 |
| EP | 1272249 B1 | 6/2010 |
| EP | 1978895 B1 | 6/2010 |
| EP | 1572033 B1 | 7/2010 |
| EP | 1968491 B1 | 7/2010 |
| EP | 1610722 B1 | 8/2010 |
| EP | 1682047 B1 | 8/2010 |
| EP | 1952772 B1 | 8/2010 |
| EP | 1427356 B1 | 9/2010 |
| EP | 1631218 B1 | 9/2010 |
| EP | 1765224 B1 | 9/2010 |
| EP | 1871290 B1 | 9/2010 |
| EP | 1895288 B1 | 9/2010 |
| EP | 1895913 B1 | 9/2010 |
| EP | 2014257 B1 | 9/2010 |
| EP | 1176913 B1 | 10/2010 |
| EP | 1178758 B1 | 10/2010 |
| EP | 1248579 B1 | 10/2010 |
| EP | 1913899 B1 | 10/2010 |
| EP | 1259193 B1 | 11/2010 |
| EP | 1928357 B1 | 11/2010 |
| EP | 1968660 B1 | 11/2010 |
| EP | 1408895 B1 | 12/2010 |

(56) References Cited

FOREIGN PATENT DOCUMENTS

| | | | |
|---|---|---|---|
| EP | 1465554 B1 | 12/2010 |
| EP | 1732473 B1 | 12/2010 |
| EP | 1768610 B1 | 12/2010 |
| EP | 1827314 B1 | 12/2010 |
| EP | 1940321 B1 | 12/2010 |
| EP | 1964532 B1 | 12/2010 |
| EP | 2078498 B1 | 12/2010 |
| EP | 1600182 B1 | 1/2011 |
| EP | 1617789 B1 | 1/2011 |
| EP | 1663332 B1 | 1/2011 |
| EP | 2147659 B1 | 1/2011 |
| EP | 1187582 B1 | 2/2011 |
| EP | 1450733 B1 | 2/2011 |
| EP | 1803421 B1 | 2/2011 |
| EP | 1833425 B1 | 2/2011 |
| EP | 2029053 B1 | 2/2011 |
| EP | 2068770 B1 | 2/2011 |
| EP | 1441784 B1 | 3/2011 |
| EP | 1534177 B1 | 3/2011 |
| EP | 1893132 B1 | 3/2011 |
| EP | 1951153 B1 | 3/2011 |
| EP | 1359978 B1 | 4/2011 |
| EP | 1667750 B1 | 4/2011 |
| EP | 1718249 B1 | 4/2011 |
| EP | 1903989 B1 | 4/2011 |
| EP | 2018122 B1 | 4/2011 |
| EP | 1610728 B1 | 5/2011 |
| EP | 2105110 B1 | 5/2011 |
| EP | 1347717 B1 | 6/2011 |
| EP | 1347791 B1 | 7/2011 |
| EP | 1862128 B1 | 7/2011 |
| EP | 2120795 A1 | 7/2011 |
| EP | 2229020 B1 | 7/2011 |
| EP | 1637087 B1 | 8/2011 |
| EP | 2153799 B1 | 8/2011 |
| EP | 2247263 B1 | 8/2011 |
| EP | 1441672 B1 | 9/2011 |
| EP | 1625832 B1 | 9/2011 |
| EP | 2173279 B1 | 9/2011 |
| EP | 2160150 B1 | 10/2011 |
| EP | 1626679 B1 | 11/2011 |
| EP | 1719476 B1 | 11/2011 |
| EP | 1928355 B1 | 11/2011 |
| EP | 2237747 B1 | 11/2011 |
| EP | 1572031 B1 | 12/2011 |
| EP | 1603493 B1 | 12/2011 |
| EP | 1945109 B1 | 12/2011 |
| EP | 1998688 B1 | 12/2011 |
| EP | 1443877 B1 | 1/2012 |
| EP | 1281375 B1 | 2/2012 |
| EP | 1699501 B1 | 2/2012 |
| EP | 1788984 B1 | 2/2012 |
| EP | 1833415 B1 | 2/2012 |
| EP | 1952785 B1 | 2/2012 |
| EP | 2055266 B1 | 2/2012 |
| EP | 2205184 B1 | 2/2012 |
| EP | 1337188 B1 | 3/2012 |
| EP | 1443974 B1 | 3/2012 |
| EP | 1542623 B1 | 3/2012 |
| EP | 1942835 B1 | 3/2012 |
| EP | 2074964 B1 | 3/2012 |
| EP | 2244661 B1 | 3/2012 |
| EP | 2273928 B1 | 3/2012 |
| EP | 1401336 B1 | 4/2012 |
| EP | 1749544 B1 | 4/2012 |
| EP | 2119417 B1 | 4/2012 |
| EP | 2152330 B1 | 4/2012 |
| EP | 2231069 B1 | 4/2012 |
| EP | 2019652 B1 | 5/2012 |
| EP | 2020958 B1 | 5/2012 |
| EP | 2192875 B1 | 5/2012 |
| EP | 2217174 B1 | 5/2012 |
| EP | 2218425 B1 | 5/2012 |
| EP | 1411847 B1 | 6/2012 |
| EP | 1727499 B1 | 6/2012 |
| EP | 2082690 B1 | 6/2012 |
| EP | 1740747 B1 | 7/2012 |
| EP | 1861044 B1 | 7/2012 |
| EP | 2052699 B1 | 7/2012 |
| EP | 1887975 B1 | 8/2012 |
| EP | 2000116 B1 | 8/2012 |
| EP | 2222247 B1 | 8/2012 |
| EP | 1605870 B1 | 9/2012 |
| EP | 1887980 B1 | 9/2012 |
| EP | 1740126 B1 | 10/2012 |
| EP | 1865889 B1 | 10/2012 |
| EP | 2033593 B1 | 10/2012 |
| EP | 2124824 B1 | 10/2012 |
| EP | 2139431 B1 | 10/2012 |
| EP | 1430853 B1 | 11/2012 |
| EP | 1928512 B1 | 11/2012 |
| EP | 2008615 B1 | 11/2012 |
| EP | 2088965 B1 | 11/2012 |
| EP | 1557138 B1 | 12/2012 |
| EP | 1924221 B1 | 12/2012 |
| EP | 2250970 B1 | 12/2012 |
| EP | 2285317 B1 | 12/2012 |
| EP | 1494731 B1 | 1/2013 |
| EP | 1610752 B1 | 1/2013 |
| EP | 1796597 B1 | 1/2013 |
| EP | 1919397 B1 | 1/2013 |
| EP | 1942834 B1 | 1/2013 |
| EP | 2015709 B1 | 1/2013 |
| EP | 2079400 B1 | 1/2013 |
| EP | 2238947 B1 | 1/2013 |
| EP | 2241287 B1 | 1/2013 |
| EP | 2359774 B1 | 1/2013 |
| EP | 1512383 B1 | 2/2013 |
| EP | 1578474 B1 | 2/2013 |
| EP | 1648339 B1 | 2/2013 |
| EP | 1750622 B1 | 2/2013 |
| EP | 1994482 B1 | 2/2013 |
| EP | 2250975 B1 | 2/2013 |
| EP | 2257242 B1 | 2/2013 |
| EP | 2265225 B1 | 2/2013 |
| EP | 1659992 B1 | 3/2013 |
| EP | 1701668 B1 | 3/2013 |
| EP | 2151216 B1 | 3/2013 |
| EP | 2340075 B1 | 3/2013 |
| EP | 1781183 B1 | 4/2013 |
| EP | 1786367 B1 | 4/2013 |
| EP | 1850795 B1 | 4/2013 |
| EP | 1861041 B1 | 4/2013 |
| EP | 2319458 B1 | 4/2013 |
| EP | 2526898 B1 | 4/2013 |
| EP | 2537487 B1 | 4/2013 |
| EP | 1901682 B1 | 5/2013 |
| EP | 1951166 B1 | 5/2013 |
| EP | 1994913 B1 | 5/2013 |
| EP | 2231070 B1 | 5/2013 |
| EP | 2401970 B1 | 5/2013 |
| EP | 2409651 B1 | 5/2013 |
| EP | 1694246 B1 | 6/2013 |
| EP | 1948078 B1 | 6/2013 |
| EP | 2135559 B1 | 6/2013 |
| EP | 1115335 B1 | 7/2013 |
| EP | 1663339 B1 | 7/2013 |
| EP | 1864687 B1 | 7/2013 |
| EP | 1977719 B1 | 7/2013 |
| EP | 2111337 B1 | 7/2013 |
| EP | 2298237 B1 | 7/2013 |
| EP | 2309949 B1 | 7/2013 |
| EP | 1599151 B1 | 8/2013 |
| EP | 1761211 B1 | 8/2013 |
| EP | 2047871 B1 | 8/2013 |
| EP | 2142144 B1 | 8/2013 |
| EP | 2150206 B1 | 8/2013 |
| EP | 2319459 B1 | 8/2013 |
| EP | 2397108 B1 | 8/2013 |
| EP | 1758523 B1 | 9/2013 |
| EP | 1545392 B1 | 10/2013 |
| EP | 1638627 B1 | 10/2013 |
| EP | 1779868 B1 | 10/2013 |
| EP | 2073756 B1 | 10/2013 |

(56) References Cited

FOREIGN PATENT DOCUMENTS

| | | |
|---|---|---|
| EP | 2111190 B1 | 10/2013 |
| EP | 1848375 B1 | 11/2013 |
| EP | 1928356 B1 | 11/2013 |
| EP | 1933766 B1 | 11/2013 |
| EP | 2109417 B1 | 11/2013 |
| EP | 2194925 B1 | 11/2013 |
| EP | 2387977 B1 | 11/2013 |
| EP | 2476394 B1 | 11/2013 |
| EP | 2529701 B1 | 11/2013 |
| EP | 1945142 B1 | 12/2013 |
| EP | 2387972 B1 | 12/2013 |
| EP | 2477555 B1 | 12/2013 |
| EP | 2117476 B1 | 1/2014 |
| EP | 2526895 B1 | 1/2014 |
| EP | 2526899 B1 | 1/2014 |
| EP | 2529696 B1 | 1/2014 |
| EP | 2529697 B1 | 1/2014 |
| EP | 2529698 B1 | 1/2014 |
| EP | 2529699 B1 | 1/2014 |
| EP | 1395214 B1 | 2/2014 |
| EP | 1499266 B1 | 2/2014 |
| EP | 1838241 B1 | 2/2014 |
| EP | 2520250 B1 | 2/2014 |
| EP | 2526977 B1 | 2/2014 |
| EP | 1629794 B1 | 3/2014 |
| EP | 1919398 B1 | 3/2014 |
| EP | 2099508 B1 | 3/2014 |
| EP | 2399549 B1 | 3/2014 |
| EP | 2422823 B1 | 3/2014 |
| EP | 1804860 B1 | 4/2014 |
| EP | 1926455 B1 | 4/2014 |
| EP | 2081519 B1 | 4/2014 |
| EP | 2117477 B1 | 4/2014 |
| EP | 2405966 B1 | 4/2014 |
| EP | 2420205 B1 | 4/2014 |
| EP | 2593048 B1 | 4/2014 |
| EP | 1499265 B1 | 5/2014 |
| EP | 1594569 B1 | 5/2014 |
| EP | 2029056 B1 | 5/2014 |
| EP | 2257243 B1 | 5/2014 |
| EP | 1791500 B1 | 6/2014 |
| EP | 2073753 B1 | 6/2014 |
| EP | 2306933 B1 | 6/2014 |
| EP | 2331017 B1 | 6/2014 |
| EP | 2337522 B1 | 6/2014 |
| EP | 2389897 B1 | 6/2014 |
| EP | 2606723 B1 | 6/2014 |
| EP | 1487350 B1 | 7/2014 |
| EP | 1977718 B1 | 7/2014 |
| EP | 2117469 B1 | 7/2014 |
| EP | 2124826 B1 | 7/2014 |
| EP | 2258316 B1 | 7/2014 |
| EP | 1667604 B1 | 8/2014 |
| EP | 1786368 B1 | 8/2014 |
| EP | 2211779 B1 | 8/2014 |
| EP | 2293740 B1 | 8/2014 |
| EP | 2367504 B1 | 8/2014 |
| EP | 2453942 B1 | 8/2014 |
| EP | 2475328 B1 | 8/2014 |
| EP | 2545884 B1 | 8/2014 |
| EP | 2571460 B1 | 8/2014 |
| EP | 1935378 B1 | 9/2014 |
| EP | 2246011 B1 | 9/2014 |
| EP | 2422749 B1 | 9/2014 |
| EP | 2531139 B1 | 9/2014 |
| EP | 2609893 B1 | 9/2014 |
| EP | 1850796 B1 | 10/2014 |
| EP | 1853199 B1 | 10/2014 |
| EP | 2133039 B1 | 10/2014 |
| EP | 2549955 B1 | 10/2014 |
| EP | 2549956 B1 | 10/2014 |
| EP | 2651335 B1 | 10/2014 |
| EP | 2049721 B1 | 11/2014 |
| EP | 2142143 B1 | 11/2014 |
| EP | 2229921 B4 | 11/2014 |
| EP | 2288403 B1 | 11/2014 |
| EP | 2415421 B1 | 11/2014 |
| EP | 1551274 B1 | 12/2014 |
| EP | 1768735 B1 | 12/2014 |
| EP | 1959865 B1 | 12/2014 |
| EP | 2077718 B1 | 12/2014 |
| EP | 2303185 B1 | 12/2014 |
| EP | 2334857 B1 | 12/2014 |
| EP | 2365840 B1 | 12/2014 |
| EP | 2420207 B1 | 12/2014 |
| EP | 2422750 B1 | 12/2014 |
| EP | 2707073 B1 | 12/2014 |
| EP | 1768630 B1 | 1/2015 |
| EP | 2254515 B1 | 1/2015 |
| EP | 2641569 B1 | 1/2015 |
| EP | 2709559 B1 | 1/2015 |
| EP | 1903990 B1 | 2/2015 |
| EP | 2255753 B1 | 2/2015 |
| EP | 2335649 B1 | 2/2015 |
| EP | 2522308 B1 | 2/2015 |
| EP | 2591754 B1 | 2/2015 |
| EP | 1861045 B1 | 3/2015 |
| EP | 2029057 B1 | 3/2015 |
| EP | 2193761 B1 | 3/2015 |
| EP | 2379010 B1 | 3/2015 |
| EP | 2416737 B1 | 3/2015 |
| EP | 1791495 B1 | 4/2015 |
| EP | 2298252 B1 | 4/2015 |
| EP | 2536359 B1 | 4/2015 |
| EP | 2538879 B1 | 4/2015 |
| EP | 2609894 B1 | 4/2015 |
| EP | 2693984 B1 | 4/2015 |
| EP | 2712633 B1 | 4/2015 |
| EP | 2747707 B1 | 4/2015 |
| EP | 1465555 B1 | 5/2015 |
| EP | 1924224 B1 | 5/2015 |
| EP | 1992369 B1 | 5/2015 |
| EP | 2410947 B1 | 5/2015 |
| EP | 2484311 B1 | 5/2015 |
| EP | 2654616 B1 | 5/2015 |
| EP | 1646332 B1 | 6/2015 |
| EP | 2745805 B1 | 6/2015 |
| EP | 2749254 B1 | 6/2015 |
| EP | 1729685 B1 | 7/2015 |
| EP | 1976439 B1 | 7/2015 |
| EP | 2068767 B1 | 7/2015 |
| EP | 2068769 B1 | 7/2015 |
| EP | 2444031 B1 | 7/2015 |
| EP | 2455041 B1 | 7/2015 |
| EP | 2498719 B1 | 7/2015 |
| EP | 2558030 B1 | 7/2015 |
| EP | 2752209 B1 | 7/2015 |
| EP | 1702247 B1 | 8/2015 |
| EP | 1729688 B1 | 8/2015 |
| EP | 1887979 B1 | 8/2015 |
| EP | 2032079 B1 | 8/2015 |
| EP | 2219558 B1 | 8/2015 |
| EP | 2234657 B1 | 8/2015 |
| EP | 2250976 B1 | 8/2015 |
| EP | 2262447 B1 | 8/2015 |
| EP | 2303384 B1 | 8/2015 |
| EP | 2560579 B1 | 8/2015 |
| EP | 2575621 B1 | 8/2015 |
| EP | 2590595 B1 | 8/2015 |
| EP | 2709560 B1 | 8/2015 |
| EP | 2755603 B1 | 8/2015 |
| EP | 1534185 B1 | 9/2015 |
| EP | 1765225 B1 | 9/2015 |
| EP | 1778127 B1 | 9/2015 |
| EP | 2094194 B1 | 9/2015 |
| EP | 2201911 B1 | 9/2015 |
| EP | 2306934 B1 | 9/2015 |
| EP | 2397113 B1 | 9/2015 |
| EP | 2453843 B1 | 9/2015 |
| EP | 2459127 B1 | 9/2015 |
| EP | 2675396 B1 | 9/2015 |
| EP | 2675397 B1 | 9/2015 |
| EP | 2736454 B1 | 9/2015 |
| EP | 2790609 B1 | 9/2015 |

(56) References Cited

FOREIGN PATENT DOCUMENTS

| | | | |
|---|---|---|---|
| EP | 2805693 B1 | 9/2015 |
| EP | 1734903 B1 | 10/2015 |
| EP | 1863546 B1 | 10/2015 |
| EP | 1900343 B1 | 10/2015 |
| EP | 2081515 B1 | 10/2015 |
| EP | 2191792 B1 | 10/2015 |
| EP | 2254513 B1 | 10/2015 |
| EP | 2381896 B1 | 10/2015 |
| EP | 2450008 B1 | 10/2015 |
| EP | 2544626 B1 | 10/2015 |
| EP | 2561830 B1 | 10/2015 |
| EP | 2600798 B1 | 10/2015 |
| EP | 2626039 B1 | 10/2015 |
| EP | 2729093 B1 | 10/2015 |
| EP | 2836165 B1 | 10/2015 |
| EP | 1863545 B1 | 11/2015 |
| EP | 2303395 B1 | 11/2015 |
| EP | 2496181 B1 | 11/2015 |
| EP | 2497446 B1 | 11/2015 |
| EP | 2772228 B1 | 11/2015 |
| EP | 1482869 B1 | 12/2015 |
| EP | 1551473 B1 | 12/2015 |
| EP | 1748745 B1 | 12/2015 |
| EP | 1755459 B1 | 12/2015 |
| EP | 1922030 B1 | 12/2015 |
| EP | 1954212 B1 | 12/2015 |
| EP | 2424472 B1 | 12/2015 |
| EP | 2470120 B1 | 12/2015 |
| EP | 2542179 B1 | 12/2015 |
| EP | 1991168 B1 | 1/2016 |
| EP | 2254512 B1 | 1/2016 |
| EP | 2422748 B1 | 1/2016 |
| EP | 1754684 B1 | 2/2016 |
| EP | 1835948 B1 | 2/2016 |
| EP | 2012712 B1 | 2/2016 |
| EP | 2285318 B1 | 2/2016 |
| EP | 2731550 B1 | 2/2016 |
| EP | 2926766 B1 | 2/2016 |
| EP | 1585463 B1 | 3/2016 |
| EP | 1638621 B1 | 3/2016 |
| EP | 1804726 B1 | 3/2016 |
| EP | 1865886 B1 | 3/2016 |
| EP | 1887982 B1 | 3/2016 |
| EP | 2150205 B1 | 3/2016 |
| EP | 2278944 B1 | 3/2016 |
| EP | 2291126 B1 | 3/2016 |
| EP | 2517674 B1 | 3/2016 |
| EP | 2520253 B1 | 3/2016 |
| EP | 2526897 B1 | 3/2016 |
| EP | 2670353 B1 | 3/2016 |
| EP | 2674130 B1 | 3/2016 |
| EP | 2780042 B1 | 3/2016 |
| EP | 1420730 B1 | 4/2016 |
| EP | 1545371 B1 | 4/2016 |
| EP | 1592367 B1 | 4/2016 |
| EP | 1708649 B1 | 4/2016 |
| EP | 1871300 B1 | 4/2016 |
| EP | 2168536 B1 | 4/2016 |
| EP | 2399550 B1 | 4/2016 |
| EP | 2433591 B1 | 4/2016 |
| EP | 2478871 B1 | 4/2016 |
| EP | 2536355 B1 | 4/2016 |
| EP | 2572676 B1 | 4/2016 |
| EP | 2606852 B1 | 4/2016 |
| EP | 2621408 B1 | 4/2016 |
| EP | 2626041 B1 | 4/2016 |
| EP | 2633821 B1 | 4/2016 |
| EP | 2670354 B1 | 4/2016 |
| EP | 2702965 B1 | 4/2016 |
| EP | 2704669 B1 | 4/2016 |
| EP | 2815725 B1 | 4/2016 |
| EP | 2194933 B1 | 5/2016 |
| EP | 2237746 B1 | 5/2016 |
| EP | 2378947 B1 | 5/2016 |
| EP | 2542184 B1 | 5/2016 |
| EP | 2572684 B1 | 5/2016 |
| EP | 2582326 B1 | 5/2016 |
| EP | 2618784 B1 | 5/2016 |
| EP | 2654623 B1 | 5/2016 |
| EP | 2656816 B1 | 5/2016 |
| EP | 2680791 B1 | 5/2016 |
| EP | 2693986 B1 | 5/2016 |
| EP | 2768429 B1 | 5/2016 |
| EP | 2806805 B1 | 5/2016 |
| EP | 2866739 B1 | 5/2016 |
| EP | 2889020 B1 | 5/2016 |
| EP | 2926767 B1 | 5/2016 |
| EP | 2926840 B1 | 5/2016 |
| EP | 29249292 B1 | 5/2016 |
| EP | 1734902 B1 | 6/2016 |
| EP | 1906884 B1 | 6/2016 |
| EP | 2111800 B1 | 6/2016 |
| EP | 2160156 B1 | 6/2016 |
| EP | 2190379 B1 | 6/2016 |
| EP | 2193762 B1 | 6/2016 |
| EP | 2416739 B1 | 6/2016 |
| EP | 2453969 B1 | 6/2016 |
| EP | 2515800 B1 | 6/2016 |
| EP | 2558031 B1 | 6/2016 |
| EP | 2563236 B1 | 6/2016 |
| EP | 2572675 B1 | 6/2016 |
| EP | 2626040 B1 | 6/2016 |
| EP | 2704668 B1 | 6/2016 |
| EP | 2777611 B1 | 6/2016 |
| EP | 2815724 B1 | 6/2016 |
| EP | 2854710 B1 | 6/2016 |
| EP | 2901966 B1 | 6/2016 |
| EP | 1605866 B1 | 7/2016 |
| EP | 1933756 B1 | 7/2016 |
| EP | 2393452 B1 | 7/2016 |
| EP | 2410948 B1 | 7/2016 |
| EP | 2412397 B1 | 7/2016 |
| EP | 2724690 B1 | 7/2016 |
| EP | 2815723 B1 | 7/2016 |
| EP | 2870945 B1 | 7/2016 |
| EP | 1401358 B1 | 8/2016 |
| EP | 1915105 B1 | 8/2016 |
| EP | 1937186 B1 | 8/2016 |
| EP | 2292186 B1 | 8/2016 |
| EP | 2379012 B1 | 8/2016 |
| EP | 2385809 B1 | 8/2016 |
| EP | 2387365 B1 | 8/2016 |
| EP | 2536345 B1 | 8/2016 |
| EP | 2537490 B1 | 8/2016 |
| EP | 2549954 B1 | 8/2016 |
| EP | 2618779 B1 | 8/2016 |
| EP | 2670352 B1 | 8/2016 |
| EP | 2829235 B1 | 8/2016 |
| EP | 2853238 B1 | 8/2016 |
| EP | 2866738 B1 | 8/2016 |
| EP | 2906150 B1 | 8/2016 |
| EP | 1156755 B1 | 9/2016 |
| EP | 1492478 B1 | 9/2016 |
| EP | 1912697 B1 | 9/2016 |
| EP | 2393449 B1 | 9/2016 |
| EP | 2670356 B1 | 9/2016 |
| EP | 2793969 B1 | 9/2016 |
| EP | 2809271 B1 | 9/2016 |
| EP | 2896425 B1 | 9/2016 |
| EP | 2023858 B1 | 10/2016 |
| EP | 2112912 B1 | 10/2016 |
| EP | 2640319 B1 | 10/2016 |
| EP | 2663257 B1 | 10/2016 |
| EP | 2727612 B1 | 10/2016 |
| EP | 2760384 B1 | 10/2016 |
| EP | 2806829 B1 | 10/2016 |
| EP | 2858599 B1 | 10/2016 |
| EP | 2918250 B1 | 10/2016 |
| EP | 2934387 B1 | 10/2016 |
| EP | 1539047 B1 | 11/2016 |
| EP | 2282700 B1 | 11/2016 |
| EP | 2400926 B1 | 11/2016 |
| EP | 2467104 B1 | 11/2016 |
| EP | 2525743 B1 | 11/2016 |

(56) References Cited

FOREIGN PATENT DOCUMENTS

| | | | |
|---|---|---|---|
| EP | 2549953 B1 | 11/2016 |
| EP | 2575696 B1 | 11/2016 |
| EP | 2598045 B1 | 11/2016 |
| EP | 2670355 B1 | 11/2016 |
| EP | 2676640 B1 | 11/2016 |
| EP | 2680792 B1 | 11/2016 |
| EP | 2707053 B1 | 11/2016 |
| EP | 2717803 B1 | 11/2016 |
| EP | 2773297 B1 | 11/2016 |
| EP | 2801387 B1 | 11/2016 |
| EP | 2844192 B1 | 11/2016 |
| EP | 2849679 B1 | 11/2016 |
| EP | 2877122 B1 | 11/2016 |
| EP | 2908778 B1 | 11/2016 |
| EP | 2922500 B1 | 11/2016 |
| EP | 2922501 B1 | 11/2016 |
| EP | 2967854 B1 | 11/2016 |
| EP | 3020365 B1 | 11/2016 |
| EP | 1645244 B1 | 12/2016 |
| EP | 1667614 B1 | 12/2016 |
| EP | 1684656 B1 | 12/2016 |
| EP | 1684670 B1 | 12/2016 |
| EP | 1750592 B1 | 12/2016 |
| EP | 1883375 B1 | 12/2016 |
| EP | 2293739 B1 | 12/2016 |
| EP | 2339988 B1 | 12/2016 |
| EP | 2512375 B1 | 12/2016 |
| EP | 2754417 B1 | 12/2016 |
| EP | 2754418 B1 | 12/2016 |
| EP | 2755562 B1 | 12/2016 |
| EP | 2889019 B1 | 12/2016 |
| EP | 3010442 B1 | 12/2016 |
| EP | 1893127 B1 | 1/2017 |
| EP | 1951352 B1 | 1/2017 |
| EP | 2109419 B1 | 1/2017 |
| EP | 2185107 B1 | 1/2017 |
| EP | 2266503 B1 | 1/2017 |
| EP | 2340055 B1 | 1/2017 |
| EP | 2395941 B1 | 1/2017 |
| EP | 2400923 B1 | 1/2017 |
| EP | 2629699 B1 | 1/2017 |
| EP | 2645963 B1 | 1/2017 |
| EP | 2654622 B1 | 1/2017 |
| EP | 2706952 B1 | 1/2017 |
| EP | 2760347 B1 | 1/2017 |
| EP | 2771064 B1 | 1/2017 |
| EP | 2780077 B1 | 1/2017 |
| EP | 2809272 B1 | 1/2017 |
| EP | 2934385 B1 | 1/2017 |
| EP | 2986255 B1 | 1/2017 |
| EP | 1507493 B1 | 2/2017 |
| EP | 2563238 B1 | 2/2017 |
| EP | 2752170 B1 | 2/2017 |
| EP | 2760371 B1 | 2/2017 |
| EP | 2793709 B1 | 2/2017 |
| EP | 2793748 B1 | 2/2017 |
| EP | 2793763 B1 | 2/2017 |
| EP | 2832317 B1 | 2/2017 |
| EP | 2921135 B1 | 2/2017 |
| EP | 2967931 B1 | 2/2017 |
| EP | 2974693 B1 | 2/2017 |
| EP | 3025680 B1 | 2/2017 |
| EP | 3025681 B1 | 2/2017 |
| EP | 1845895 B1 | 3/2017 |
| EP | 2190385 B1 | 3/2017 |
| EP | 2266504 B1 | 3/2017 |
| EP | 2341871 B1 | 3/2017 |
| EP | 2379011 B1 | 3/2017 |
| EP | 2379013 B1 | 3/2017 |
| EP | 2640316 B1 | 3/2017 |
| EP | 2731552 B1 | 3/2017 |
| EP | 2756109 B1 | 3/2017 |
| EP | 2773298 B1 | 3/2017 |
| EP | 2832316 B1 | 3/2017 |
| EP | 2854718 B1 | 3/2017 |
| EP | 2881083 B1 | 3/2017 |
| EP | 2934390 B1 | 3/2017 |
| EP | 2934391 B1 | 3/2017 |
| EP | 2014239 B1 | 4/2017 |
| EP | 2111189 B1 | 4/2017 |
| EP | 2393451 B1 | 4/2017 |
| EP | 2617388 B1 | 4/2017 |
| EP | 2629700 B1 | 4/2017 |
| EP | 2832318 B1 | 4/2017 |
| EP | 2893904 B1 | 4/2017 |
| EP | 2982340 B1 | 4/2017 |
| EP | 3000436 B1 | 4/2017 |
| EP | 3001979 B1 | 4/2017 |
| EP | 3043749 B1 | 4/2017 |
| EP | 3045147 B1 | 4/2017 |
| EP | 3054893 B1 | 4/2017 |
| EP | 1855614 B1 | 5/2017 |
| EP | 2001402 B1 | 5/2017 |
| EP | 2032080 B1 | 5/2017 |
| EP | 2262451 B1 | 5/2017 |
| EP | 2470119 B1 | 5/2017 |
| EP | 2478869 B1 | 5/2017 |
| EP | 2538880 B1 | 5/2017 |
| EP | 2545850 B1 | 5/2017 |
| EP | 2600799 B1 | 5/2017 |
| EP | 2717926 B1 | 5/2017 |
| EP | 2726024 B1 | 5/2017 |
| EP | 2805678 B1 | 5/2017 |
| EP | 2809270 B1 | 5/2017 |
| EP | 2918245 B1 | 5/2017 |
| EP | 2953579 B1 | 5/2017 |
| EP | 2976043 B1 | 5/2017 |
| EP | 2979666 B1 | 5/2017 |
| EP | 3011931 B1 | 5/2017 |
| EP | 3025682 B1 | 5/2017 |
| EP | 3033135 B1 | 5/2017 |
| EP | 2351541 B1 | 6/2017 |
| EP | 2384165 B1 | 6/2017 |
| EP | 2400924 B1 | 6/2017 |
| EP | 2419041 B1 | 6/2017 |
| EP | 2419050 B1 | 6/2017 |
| EP | 2489331 B1 | 6/2017 |
| EP | 2493417 B1 | 6/2017 |
| EP | 2560585 B1 | 6/2017 |
| EP | 2611387 B1 | 6/2017 |
| EP | 2645967 B1 | 6/2017 |
| EP | 2677965 B1 | 6/2017 |
| EP | 2760349 B1 | 6/2017 |
| EP | 2826443 B1 | 6/2017 |
| EP | 2906148 B1 | 6/2017 |
| EP | 2929860 B1 | 6/2017 |
| EP | 2934669 B1 | 6/2017 |
| EP | 2967852 B1 | 6/2017 |
| EP | 1624810 B1 | 7/2017 |
| EP | 2026703 B1 | 7/2017 |
| EP | 2293718 B1 | 7/2017 |
| EP | 2339989 B1 | 7/2017 |
| EP | 2344076 B1 | 7/2017 |
| EP | 2486893 B1 | 7/2017 |
| EP | 2536356 B1 | 7/2017 |
| EP | 2548534 B1 | 7/2017 |
| EP | 2608742 B1 | 7/2017 |
| EP | 2673038 B1 | 7/2017 |
| EP | 2676638 B1 | 7/2017 |
| EP | 2825107 B1 | 7/2017 |
| EP | 2841020 B1 | 7/2017 |
| EP | 2934386 B1 | 7/2017 |
| EP | 2943151 B1 | 7/2017 |
| EP | 3058894 B1 | 7/2017 |
| EP | 3071151 B1 | 7/2017 |
| EP | 1530441 B1 | 8/2017 |
| EP | 1722716 B1 | 8/2017 |
| EP | 1971289 B1 | 8/2017 |
| EP | 2323591 B1 | 8/2017 |
| EP | 2344070 B1 | 8/2017 |
| EP | 2413842 B1 | 8/2017 |
| EP | 2427143 B1 | 8/2017 |
| EP | 2459077 B1 | 8/2017 |
| EP | 2480167 B1 | 8/2017 |

(56) References Cited

FOREIGN PATENT DOCUMENTS

| | | | |
|---|---|---|---|
| EP | 2482749 | B1 | 8/2017 |
| EP | 2568925 | B1 | 8/2017 |
| EP | 2617389 | B1 | 8/2017 |
| EP | 2713954 | B1 | 8/2017 |
| EP | 2755602 | B1 | 8/2017 |
| EP | 2800602 | B1 | 8/2017 |
| EP | 2809263 | B1 | 8/2017 |
| EP | 2830536 | B1 | 8/2017 |
| EP | 2841009 | B1 | 8/2017 |
| EP | 2844190 | B1 | 8/2017 |
| EP | 2849681 | B1 | 8/2017 |
| EP | 2858600 | B1 | 8/2017 |
| EP | 2897556 | B1 | 8/2017 |
| EP | 2934388 | B1 | 8/2017 |
| EP | 2979667 | B1 | 8/2017 |
| EP | 1799093 | B1 | 9/2017 |
| EP | 2010103 | B1 | 9/2017 |
| EP | 2114304 | B1 | 9/2017 |
| EP | 2344090 | B1 | 9/2017 |
| EP | 2398421 | B1 | 9/2017 |
| EP | 2437687 | B1 | 9/2017 |
| EP | 2453970 | B1 | 9/2017 |
| EP | 2509538 | B1 | 9/2017 |
| EP | 2713956 | B1 | 9/2017 |
| EP | 2772227 | B1 | 9/2017 |
| EP | 2787924 | B1 | 9/2017 |
| EP | 2803335 | B1 | 9/2017 |
| EP | 2811939 | B1 | 9/2017 |
| EP | 2830537 | B1 | 9/2017 |
| EP | 2865355 | B1 | 9/2017 |
| EP | 2872047 | B1 | 9/2017 |
| EP | 2934389 | B1 | 9/2017 |
| EP | 1945141 | B1 | 10/2017 |
| EP | 2317956 | B1 | 10/2017 |
| EP | 2613737 | B1 | 10/2017 |
| EP | 2620125 | B1 | 10/2017 |
| EP | 2720642 | B1 | 10/2017 |
| EP | 2741682 | B1 | 10/2017 |
| EP | 2872077 | B1 | 10/2017 |
| EP | 3021925 | B1 | 10/2017 |
| EP | 1651148 | B1 | 11/2017 |
| EP | 1913901 | B1 | 11/2017 |
| EP | 2222248 | B1 | 11/2017 |
| EP | 2296581 | B1 | 11/2017 |
| EP | 2326264 | B1 | 11/2017 |
| EP | 2427142 | B1 | 11/2017 |
| EP | 2456483 | B1 | 11/2017 |
| EP | 2493423 | B1 | 11/2017 |
| EP | 2611391 | B1 | 11/2017 |
| EP | 2618780 | B1 | 11/2017 |
| EP | 2658480 | B1 | 11/2017 |
| EP | 2710978 | B1 | 11/2017 |
| EP | 2832315 | B1 | 11/2017 |
| EP | 2954875 | B1 | 11/2017 |
| EP | 2967861 | B1 | 11/2017 |
| EP | 2982338 | B1 | 11/2017 |
| EP | 3027144 | B1 | 11/2017 |
| EP | 3043746 | B1 | 11/2017 |
| EP | 3049026 | B1 | 11/2017 |
| EP | 3068311 | B1 | 11/2017 |
| EP | 3110368 | B1 | 11/2017 |
| EP | 3110369 | B1 | 11/2017 |
| EP | 3132773 | B1 | 11/2017 |
| EP | 1667603 | B1 | 12/2017 |
| EP | 1874954 | B1 | 12/2017 |
| EP | 2427145 | B1 | 12/2017 |
| EP | 2542185 | B1 | 12/2017 |
| EP | 2723274 | B1 | 12/2017 |
| EP | 2736455 | B1 | 12/2017 |
| EP | 2736457 | B1 | 12/2017 |
| EP | 2830534 | B1 | 12/2017 |
| EP | 2830535 | B1 | 12/2017 |
| EP | 2911592 | B1 | 12/2017 |
| EP | 2916772 | B1 | 12/2017 |
| EP | 2967922 | B1 | 12/2017 |
| EP | 3009105 | B1 | 12/2017 |
| EP | 3088037 | B1 | 12/2017 |
| EP | 3115023 | B1 | 12/2017 |
| EP | 1492458 | B1 | 1/2018 |
| EP | 1768604 | B1 | 1/2018 |
| EP | 1951154 | B1 | 1/2018 |
| EP | 2091465 | B1 | 1/2018 |
| EP | 2345380 | B1 | 1/2018 |
| EP | 2456363 | B1 | 1/2018 |
| EP | 2531143 | B1 | 1/2018 |
| EP | 2621407 | B1 | 1/2018 |
| EP | 2694123 | B1 | 1/2018 |
| EP | 2774630 | B1 | 1/2018 |
| EP | 2775962 | B1 | 1/2018 |
| EP | 2874568 | B1 | 1/2018 |
| EP | 2967863 | B1 | 1/2018 |
| EP | 2967869 | B1 | 1/2018 |
| EP | 3033047 | B1 | 1/2018 |
| EP | 3037065 | B1 | 1/2018 |
| EP | 3049025 | B1 | 1/2018 |
| EP | 3052052 | B1 | 1/2018 |
| EP | 3078350 | B1 | 1/2018 |
| EP | 2197512 | B1 | 2/2018 |
| EP | 2248486 | B1 | 2/2018 |
| EP | 2344066 | B1 | 2/2018 |
| EP | 2381854 | B1 | 2/2018 |
| EP | 2667823 | B1 | 2/2018 |
| EP | 2699169 | B1 | 2/2018 |
| EP | 2714177 | B1 | 2/2018 |
| EP | 2736544 | B1 | 2/2018 |
| EP | 2846736 | B1 | 2/2018 |
| EP | 2886082 | B1 | 2/2018 |
| EP | 2886084 | B1 | 2/2018 |
| EP | 2931178 | B1 | 2/2018 |
| EP | 2934392 | B1 | 2/2018 |
| EP | 3150173 | B1 | 2/2018 |
| EP | 1959864 | B1 | 3/2018 |
| EP | 2513200 | B1 | 3/2018 |
| EP | 2608815 | B1 | 3/2018 |
| EP | 2858711 | B1 | 3/2018 |
| EP | 2938292 | B1 | 3/2018 |
| EP | 2943132 | B1 | 3/2018 |
| EP | 2983620 | B1 | 3/2018 |
| EP | 3003219 | B1 | 3/2018 |
| EP | 3005979 | B1 | 3/2018 |
| EP | 3037064 | B1 | 3/2018 |
| EP | 3046511 | B1 | 3/2018 |
| EP | 3142603 | B1 | 3/2018 |
| EP | 2209440 | B1 | 4/2018 |
| EP | 2536357 | B1 | 4/2018 |
| EP | 2605725 | B1 | 4/2018 |
| EP | 2608743 | B1 | 4/2018 |
| EP | 2709561 | B1 | 4/2018 |
| EP | 2787925 | B1 | 4/2018 |
| EP | 2789314 | B1 | 4/2018 |
| EP | 2900150 | B1 | 4/2018 |
| EP | 2908779 | B1 | 4/2018 |
| EP | 2922502 | B1 | 4/2018 |
| EP | 2964441 | B1 | 4/2018 |
| EP | 2967868 | B1 | 4/2018 |
| EP | 2979665 | B1 | 4/2018 |
| EP | 2994073 | B1 | 4/2018 |
| EP | 3095394 | B1 | 4/2018 |
| EP | 3134033 | B1 | 4/2018 |
| EP | 1945112 | B1 | 5/2018 |
| EP | 2007313 | B1 | 5/2018 |
| EP | 2316381 | B2 | 5/2018 |
| EP | 2377469 | B1 | 5/2018 |
| EP | 2531115 | B1 | 5/2018 |
| EP | 2561831 | B1 | 5/2018 |
| EP | 2605724 | B1 | 5/2018 |
| EP | 2723277 | B1 | 5/2018 |
| EP | 2741711 | B1 | 5/2018 |
| EP | 2755573 | B1 | 5/2018 |
| EP | 2819818 | B1 | 5/2018 |
| EP | 2833836 | B1 | 5/2018 |
| EP | 2886083 | B1 | 5/2018 |
| EP | 2943157 | B1 | 5/2018 |
| EP | 2948099 | B1 | 5/2018 |

(56) References Cited

FOREIGN PATENT DOCUMENTS

| | | |
|---|---|---|
| EP | 3000437 B1 | 5/2018 |
| EP | 3145448 B1 | 5/2018 |
| EP | 3154475 B1 | 5/2018 |
| EP | 2150312 B1 | 6/2018 |
| EP | 2379322 B1 | 6/2018 |
| EP | 2400925 B1 | 6/2018 |
| EP | 2552355 B1 | 6/2018 |
| EP | 2560589 B1 | 6/2018 |
| EP | 2563277 B1 | 6/2018 |
| EP | 2661305 B1 | 6/2018 |
| EP | 2736456 B1 | 6/2018 |
| EP | 2782523 B1 | 6/2018 |
| EP | 3056170 B1 | 6/2018 |
| EP | 3062745 B1 | 6/2018 |
| EP | 3130320 B1 | 6/2018 |
| EP | 3187150 B1 | 6/2018 |
| EP | 2478872 B1 | 7/2018 |
| EP | 2563278 B1 | 7/2018 |
| EP | 2616004 B1 | 7/2018 |
| EP | 2779943 B1 | 7/2018 |
| EP | 2802290 B1 | 7/2018 |
| EP | 2816980 B1 | 7/2018 |
| EP | 2938293 B1 | 7/2018 |
| EP | 3107496 B1 | 7/2018 |
| EP | 3178450 B1 | 7/2018 |
| EP | 3212097 B1 | 7/2018 |
| EP | 2536354 B1 | 8/2018 |
| EP | 2616006 B1 | 8/2018 |
| EP | 2797556 B1 | 8/2018 |
| EP | 2822473 B1 | 8/2018 |
| EP | 2854711 B1 | 8/2018 |
| EP | 2866847 B1 | 8/2018 |
| EP | 2918246 B1 | 8/2018 |
| EP | 2967845 B1 | 8/2018 |
| EP | 2999436 B1 | 8/2018 |
| EP | 3013281 B1 | 8/2018 |
| EP | 3060170 B1 | 8/2018 |
| EP | 3104811 B1 | 8/2018 |
| EP | 3143944 B1 | 8/2018 |
| EP | 3157467 B1 | 8/2018 |
| EP | 3193791 B1 | 8/2018 |
| EP | 3241526 B1 | 8/2018 |
| EP | 2114305 B1 | 9/2018 |
| EP | 2155115 B1 | 9/2018 |
| EP | 2601910 B1 | 9/2018 |
| EP | 2617390 B1 | 9/2018 |
| EP | 2734157 B1 | 9/2018 |
| EP | 2968674 B1 | 9/2018 |
| EP | 2999415 B1 | 9/2018 |
| EP | 3106130 B1 | 9/2018 |
| EP | 3151763 B1 | 9/2018 |
| EP | 3213717 B1 | 9/2018 |
| EP | 3245985 B1 | 9/2018 |
| EP | 1827256 B1 | 10/2018 |
| EP | 1850790 B1 | 10/2018 |
| EP | 2063823 B1 | 10/2018 |
| EP | 2124825 B1 | 10/2018 |
| EP | 2249746 B1 | 10/2018 |
| EP | 2254514 B1 | 10/2018 |
| EP | 2285309 B1 | 10/2018 |
| EP | 2455042 B1 | 10/2018 |
| EP | 2571561 B1 | 10/2018 |
| EP | 2616008 B1 | 10/2018 |
| EP | 2647393 B1 | 10/2018 |
| EP | 2739214 B1 | 10/2018 |
| EP | 2739247 B1 | 10/2018 |
| EP | 2776114 B1 | 10/2018 |
| EP | 2836171 B1 | 10/2018 |
| EP | 2842581 B1 | 10/2018 |
| EP | 2870946 B1 | 10/2018 |
| EP | 2923665 B1 | 10/2018 |
| EP | 2964277 B1 | 10/2018 |
| EP | 3001978 B1 | 10/2018 |
| EP | 3010562 B1 | 10/2018 |
| EP | 3072475 B1 | 10/2018 |
| EP | 3081161 B1 | 10/2018 |
| EP | 3081195 B1 | 10/2018 |
| EP | 3099345 B1 | 10/2018 |
| EP | 3120809 B1 | 10/2018 |
| EP | 3238663 B1 | 10/2018 |
| EP | 1708650 B1 | 11/2018 |
| EP | 1945143 B1 | 11/2018 |
| EP | 2205183 B1 | 11/2018 |
| EP | 2663258 B1 | 11/2018 |
| EP | 2790615 B1 | 11/2018 |
| EP | 2854709 B1 | 11/2018 |
| EP | 2898859 B1 | 11/2018 |
| EP | 2921139 B1 | 11/2018 |
| EP | 2928538 B1 | 11/2018 |
| EP | 3075354 B1 | 11/2018 |
| EP | 3082949 B1 | 11/2018 |
| EP | 3145452 B1 | 11/2018 |
| EP | 3216424 B1 | 11/2018 |
| EP | 3260084 B1 | 11/2018 |
| EP | 1858450 B1 | 12/2018 |
| EP | 2150208 B1 | 12/2018 |
| EP | 2326261 B1 | 12/2018 |
| EP | 2344075 B1 | 12/2018 |
| EP | 2370028 B1 | 12/2018 |
| EP | 2555709 B1 | 12/2018 |
| EP | 2564812 B1 | 12/2018 |
| EP | 2777618 B1 | 12/2018 |
| EP | 2814427 B1 | 12/2018 |
| EP | 2829240 B1 | 12/2018 |
| EP | 2911594 B1 | 12/2018 |
| EP | 2911729 B1 | 12/2018 |
| EP | 2954876 B1 | 12/2018 |
| EP | 2958520 B1 | 12/2018 |
| EP | 2958605 B1 | 12/2018 |
| EP | 3010446 B1 | 12/2018 |
| EP | 3064174 B1 | 12/2018 |
| EP | 3206628 B1 | 12/2018 |
| EP | 3242629 B1 | 12/2018 |
| EP | 3260085 B1 | 12/2018 |
| EP | 3266416 B1 | 12/2018 |
| EP | 3326583 B1 | 12/2018 |
| EP | 2129332 B1 | 1/2019 |
| EP | 2196159 B1 | 1/2019 |
| EP | 2370025 B1 | 1/2019 |
| EP | 2549957 B1 | 1/2019 |
| EP | 2819619 B1 | 1/2019 |
| EP | 2849680 B1 | 1/2019 |
| EP | 2856972 B1 | 1/2019 |
| EP | 2866742 B1 | 1/2019 |
| EP | 2884946 B1 | 1/2019 |
| EP | 2948102 B1 | 1/2019 |
| EP | 2979664 B1 | 1/2019 |
| EP | 3043748 B1 | 1/2019 |
| EP | 3145449 B1 | 1/2019 |
| EP | 3332743 B1 | 1/2019 |
| EP | 1895943 B1 | 2/2019 |
| EP | 2070490 B1 | 2/2019 |
| EP | 2308425 B1 | 2/2019 |
| EP | 2379009 B1 | 2/2019 |
| EP | 2575685 B1 | 2/2019 |
| EP | 2688562 B1 | 2/2019 |
| EP | 2714068 B1 | 2/2019 |
| EP | 2720641 B1 | 2/2019 |
| EP | 2760375 B1 | 2/2019 |
| EP | 2862590 B1 | 2/2019 |
| EP | 2925259 B1 | 2/2019 |
| EP | 2931179 B1 | 2/2019 |
| EP | 3005983 B1 | 2/2019 |
| EP | 3023117 B1 | 2/2019 |
| EP | 3184083 B1 | 2/2019 |
| EP | 3202333 B1 | 2/2019 |
| EP | 3261583 B1 | 2/2019 |
| EP | 3278832 B1 | 2/2019 |
| EP | 1771132 B1 | 3/2019 |
| EP | 1959866 B1 | 3/2019 |
| EP | 2120794 B1 | 3/2019 |
| EP | 2259728 B1 | 3/2019 |
| EP | 2344074 B1 | 3/2019 |
| EP | 2552356 B1 | 3/2019 |

(56) References Cited

FOREIGN PATENT DOCUMENTS

| | | | |
|---|---|---|---|
| EP | 2598044 B1 | 3/2019 |
| EP | 2659861 B1 | 3/2019 |
| EP | 2670357 B1 | 3/2019 |
| EP | 2898902 B1 | 3/2019 |
| EP | 2948098 B1 | 3/2019 |
| EP | 2948101 B1 | 3/2019 |
| EP | 2967865 B1 | 3/2019 |
| EP | 2974695 B1 | 3/2019 |
| EP | 3027243 B1 | 3/2019 |
| EP | 3145445 B1 | 3/2019 |
| EP | 3151783 B1 | 3/2019 |
| EP | 3151784 B1 | 3/2019 |
| EP | 3278768 B1 | 3/2019 |
| EP | 3320943 B1 | 3/2019 |
| EP | 1793745 B1 | 4/2019 |
| EP | 1855623 B1 | 4/2019 |
| EP | 2129333 B1 | 4/2019 |
| EP | 2149349 B1 | 4/2019 |
| EP | 2438888 B1 | 4/2019 |
| EP | 2484309 B1 | 4/2019 |
| EP | 2519268 B1 | 4/2019 |
| EP | 2528545 B1 | 4/2019 |
| EP | 2536358 B1 | 4/2019 |
| EP | 2661239 B1 | 4/2019 |
| EP | 2709563 B1 | 4/2019 |
| EP | 2736451 B1 | 4/2019 |
| EP | 2810619 B1 | 4/2019 |
| EP | 2810622 B1 | 4/2019 |
| EP | 2879589 B1 | 4/2019 |
| EP | 2921198 B1 | 4/2019 |
| EP | 2986256 B1 | 4/2019 |
| EP | 3090704 B1 | 4/2019 |
| EP | 3116445 B1 | 4/2019 |
| EP | 3141217 B1 | 4/2019 |
| EP | 3193745 B1 | 4/2019 |
| EP | 3241525 B1 | 4/2019 |
| EP | 1703870 B1 | 5/2019 |
| EP | 1708642 B1 | 5/2019 |
| EP | 2240121 B1 | 5/2019 |
| EP | 2663259 B1 | 5/2019 |
| EP | 2695586 B1 | 5/2019 |
| EP | 2726018 B1 | 5/2019 |
| EP | 2954872 B1 | 5/2019 |
| EP | 3071150 B1 | 5/2019 |
| EP | 3110370 B1 | 5/2019 |
| EP | 3111890 B1 | 5/2019 |
| EP | 3182932 B1 | 5/2019 |
| EP | 3192472 B1 | 5/2019 |
| EP | 3238661 B1 | 5/2019 |
| EP | 3284503 B1 | 5/2019 |
| EP | 3302364 B1 | 5/2019 |
| EP | 3315094 B1 | 5/2019 |
| EP | 3316818 B1 | 5/2019 |
| EP | 1624792 B1 | 6/2019 |
| EP | 1737394 B1 | 6/2019 |
| EP | 1858451 B1 | 6/2019 |
| EP | 1895944 B1 | 6/2019 |
| EP | 1968487 B1 | 6/2019 |
| EP | 2004095 B1 | 6/2019 |
| EP | 2010102 B1 | 6/2019 |
| EP | 2131788 B1 | 6/2019 |
| EP | 2560580 B1 | 6/2019 |
| EP | 2618782 B1 | 6/2019 |
| EP | 2868296 B1 | 6/2019 |
| EP | 2961358 B1 | 6/2019 |
| EP | 2967847 B1 | 6/2019 |
| EP | 2985006 B1 | 6/2019 |
| EP | 3033048 B1 | 6/2019 |
| EP | 3116446 B1 | 6/2019 |
| EP | 3119451 B1 | 6/2019 |
| EP | 3131503 B1 | 6/2019 |
| EP | 3213718 B1 | 6/2019 |
| EP | 3275390 B1 | 6/2019 |
| EP | 3300692 B1 | 6/2019 |
| EP | 3326585 B1 | 6/2019 |
| EP | 3338737 B1 | 6/2019 |
| EP | 3357457 B1 | 6/2019 |
| EP | 3372198 B1 | 6/2019 |
| EP | 1659981 B1 | 7/2019 |
| EP | 1924223 B1 | 7/2019 |
| EP | 2249745 B1 | 7/2019 |
| EP | 2296744 B1 | 7/2019 |
| EP | 2331019 B1 | 7/2019 |
| EP | 2368527 B1 | 7/2019 |
| EP | 2509542 B1 | 7/2019 |
| EP | 2555710 B1 | 7/2019 |
| EP | 2575682 B1 | 7/2019 |
| EP | 2575683 B1 | 7/2019 |
| EP | 2640431 B1 | 7/2019 |
| EP | 2641572 B1 | 7/2019 |
| EP | 2649964 B1 | 7/2019 |
| EP | 2767260 B1 | 7/2019 |
| EP | 2777615 B1 | 7/2019 |
| EP | 2838476 B1 | 7/2019 |
| EP | 2861186 B1 | 7/2019 |
| EP | 2877124 B1 | 7/2019 |
| EP | 2877132 B1 | 7/2019 |
| EP | 2921565 B1 | 7/2019 |
| EP | 2938291 B1 | 7/2019 |
| EP | 2999433 B1 | 7/2019 |
| EP | 3145450 B1 | 7/2019 |
| EP | 3254644 B1 | 7/2019 |
| EP | 3315093 B1 | 7/2019 |
| EP | 3344189 B1 | 7/2019 |
| EP | 1861043 B1 | 8/2019 |
| EP | 2303190 B1 | 8/2019 |
| EP | 2593171 B1 | 8/2019 |
| EP | 2632393 B1 | 8/2019 |
| EP | 2663355 B1 | 8/2019 |
| EP | 2665509 B1 | 8/2019 |
| EP | 2688525 B1 | 8/2019 |
| EP | 2699201 B1 | 8/2019 |
| EP | 2755564 B1 | 8/2019 |
| EP | 2769681 B1 | 8/2019 |
| EP | 2793751 B1 | 8/2019 |
| EP | 2900177 B1 | 8/2019 |
| EP | 2967536 B1 | 8/2019 |
| EP | 3050541 B1 | 8/2019 |
| EP | 3102152 B1 | 8/2019 |
| EP | 3157607 B1 | 8/2019 |
| EP | 3231392 B1 | 8/2019 |
| EP | 3284411 B1 | 8/2019 |
| EP | 3328318 B1 | 8/2019 |
| EP | 3348233 B1 | 8/2019 |
| EP | 3366262 B1 | 8/2019 |
| EP | 2368525 B1 | 9/2019 |
| EP | 2542186 B1 | 9/2019 |
| EP | 2656863 B1 | 9/2019 |
| EP | 3003221 B1 | 9/2019 |
| EP | 3003452 B1 | 9/2019 |
| EP | 3220971 B1 | 9/2019 |
| EP | 3223874 B1 | 9/2019 |
| EP | 3288495 B1 | 9/2019 |
| EP | 3311776 B1 | 9/2019 |
| EP | 3334379 B1 | 9/2019 |
| EP | 1740265 B1 | 10/2019 |
| EP | 2039756 B1 | 10/2019 |
| EP | 2456506 B1 | 10/2019 |
| EP | 2470122 B1 | 10/2019 |
| EP | 2613738 B1 | 10/2019 |
| EP | 2637607 B1 | 10/2019 |
| EP | 2674174 B1 | 10/2019 |
| EP | 2811923 B1 | 10/2019 |
| EP | 2901967 B1 | 10/2019 |
| EP | 3010431 B1 | 10/2019 |
| EP | 3019091 B1 | 10/2019 |
| EP | 3019123 B1 | 10/2019 |
| EP | 3057522 B1 | 10/2019 |
| EP | 3067075 B1 | 10/2019 |
| EP | 3146937 B1 | 10/2019 |
| EP | 3238777 B1 | 10/2019 |
| EP | 3359211 B1 | 10/2019 |
| EP | 3388026 B1 | 10/2019 |
| EP | 3432806 B1 | 10/2019 |

(56) References Cited

FOREIGN PATENT DOCUMENTS

| | | | |
|---|---|---|---|
| EP | 2043559 | B1 | 11/2019 |
| EP | 2358297 | B1 | 11/2019 |
| EP | 2358308 | B1 | 11/2019 |
| EP | 2405863 | B1 | 11/2019 |
| EP | 2701633 | B1 | 11/2019 |
| EP | 2898857 | B1 | 11/2019 |
| EP | 2967853 | B1 | 11/2019 |
| EP | 3009104 | B1 | 11/2019 |
| EP | 3021792 | B1 | 11/2019 |
| EP | 3076900 | B1 | 11/2019 |
| EP | 3111889 | B1 | 11/2019 |
| EP | 3142607 | B1 | 11/2019 |
| EP | 3167850 | B1 | 11/2019 |
| EP | 3397205 | B1 | 11/2019 |
| ER | 2647354 | B1 | 10/2015 |
| FR | 2815844 | B1 | 1/2003 |
| FR | 2826863 | B1 | 9/2003 |
| FR | 2828091 | B1 | 11/2003 |
| FR | 2847800 | B1 | 10/2005 |
| FR | 2858543 | B1 | 2/2006 |
| FR | 2828263 | B1 | 5/2007 |
| FR | 2874812 | B1 | 6/2007 |
| FR | 2874813 | B1 | 6/2007 |
| FR | 2883721 | B1 | 6/2007 |
| FR | 2894131 | B1 | 12/2008 |
| FR | 2899096 | B1 | 12/2008 |
| FR | 2910269 | B1 | 2/2009 |
| FR | 2909857 | B1 | 3/2009 |
| FR | 2906454 | B1 | 4/2009 |
| FR | 2906998 | B1 | 4/2009 |
| FR | 2913879 | B1 | 6/2009 |
| FR | 2916959 | B1 | 9/2009 |
| FR | 2892939 | B1 | 1/2010 |
| FR | 2915678 | B1 | 4/2010 |
| FR | 2930137 | B1 | 4/2010 |
| FR | 2915903 | B1 | 6/2010 |
| FR | 2916627 | B1 | 9/2010 |
| FR | 2920644 | B1 | 9/2010 |
| FR | 2932376 | B1 | 4/2011 |
| FR | 2947716 | B1 | 9/2011 |
| FR | 2945440 | B1 | 12/2012 |
| FR | 2951549 | B1 | 8/2013 |
| FR | 2964855 | B1 | 10/2013 |
| FR | 2977792 | B1 | 10/2013 |
| FR | 2980968 | B1 | 12/2013 |
| FR | 2986149 | B1 | 12/2014 |
| FR | 2997288 | B1 | 1/2015 |
| FR | 2998167 | B1 | 1/2015 |
| FR | 2996747 | B1 | 2/2015 |
| FR | 2996748 | B1 | 2/2015 |
| FR | 3004638 | B1 | 5/2015 |
| FR | 2982763 | B1 | 7/2015 |
| FR | 2991162 | B1 | 7/2015 |
| FR | 3006582 | B1 | 7/2015 |
| FR | 3001121 | B1 | 1/2016 |
| FR | 2998166 | B1 | 2/2016 |
| FR | 3021862 | B1 | 5/2016 |
| FR | 3004917 | B1 | 6/2016 |
| FR | 3006884 | B1 | 6/2016 |
| FR | 3023704 | B1 | 8/2016 |
| FR | 3008885 | B1 | 12/2016 |
| FR | 3033494 | B1 | 3/2017 |
| FR | 3057154 | B1 | 10/2018 |
| FR | 3058631 | B1 | 1/2019 |
| FR | 3058632 | B1 | 1/2019 |
| FR | 3060292 | B1 | 1/2019 |
| FR | 3063631 | B1 | 3/2019 |
| FR | 3020265 | B1 | 9/2019 |
| FR | 3072013 | B1 | 9/2019 |
| GB | 243370 | A | 8/1926 |
| GB | 2407146 | B | 4/2006 |
| GB | 2398245 | B | 3/2007 |
| GB | 2433700 | B | 12/2007 |
| GB | 2478498 | B | 7/2012 |
| GB | 2536538 | B | 7/2016 |
| GB | 2530487 | B | 12/2016 |
| GB | 2517609 | B | 5/2017 |
| GB | 2538749 | B | 8/2017 |
| GB | 2538072 | B | 11/2017 |
| GB | 2548891 | B | 7/2018 |
| IE | 2023859 | B1 | 12/2012 |
| WO | WO-2008103722 | A2 | 8/2008 |
| WO | WO-2009134701 | A2 | 11/2009 |
| WO | WO-2011137531 | A9 | 11/2011 |
| WO | WO-2013075215 | A1 | 5/2013 |
| WO | WO-2019036810 | A1 | 2/2019 |

OTHER PUBLICATIONS

"International Application Serial No. PCT/CA2018/051019, Written Opinion dated Nov. 19, 2018", 6 pgs.

"International Application Serial No. PCT/CA2018/051019, International Preliminary Report on Patentability dated Mar. 5, 2020", 8 pgs.

"European Application Serial 18849180.7 Response filed Oct. 9, 2020 to Communication pursuant to Rules 161(1) and 162 EPC dated Apr. 1, 2020", 18 pgs.

* cited by examiner

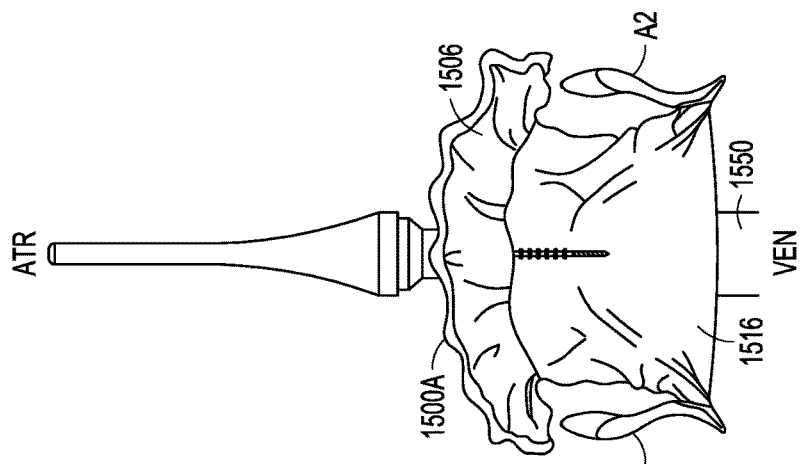

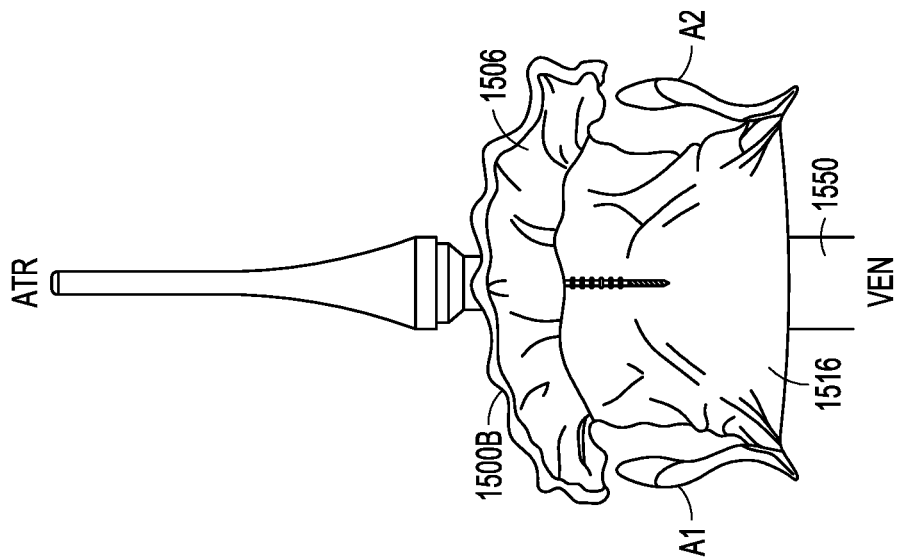
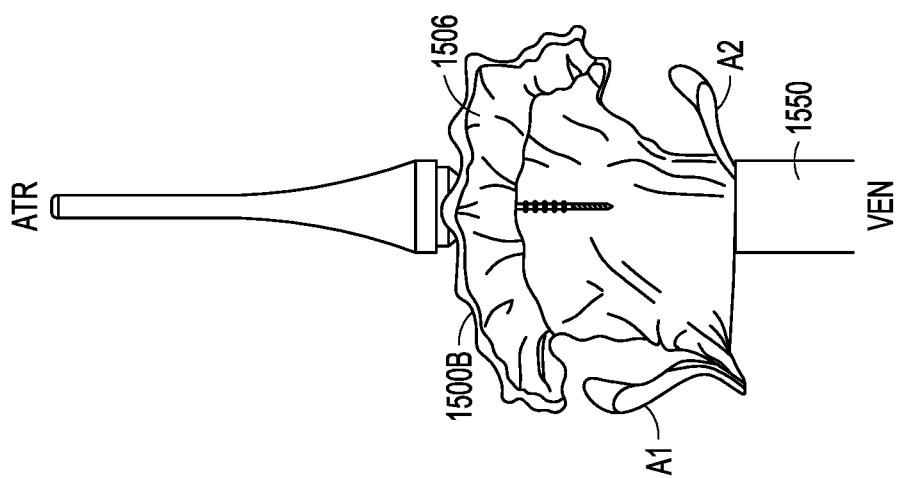
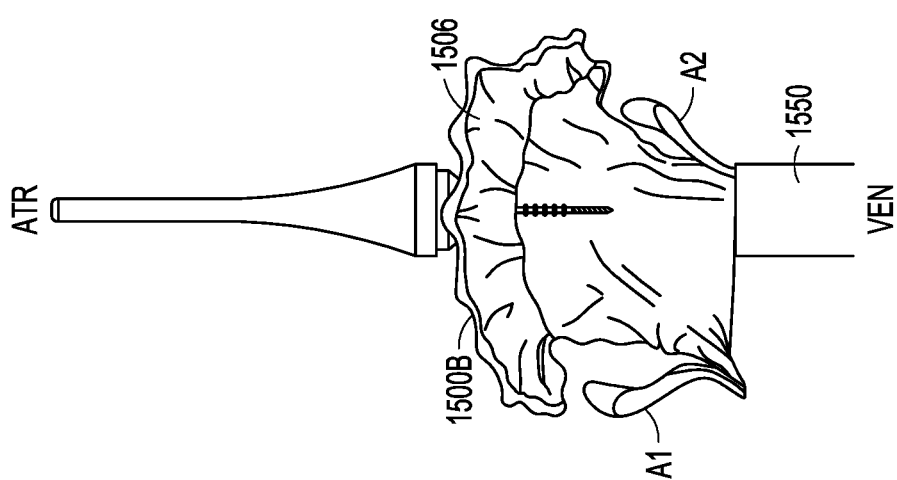

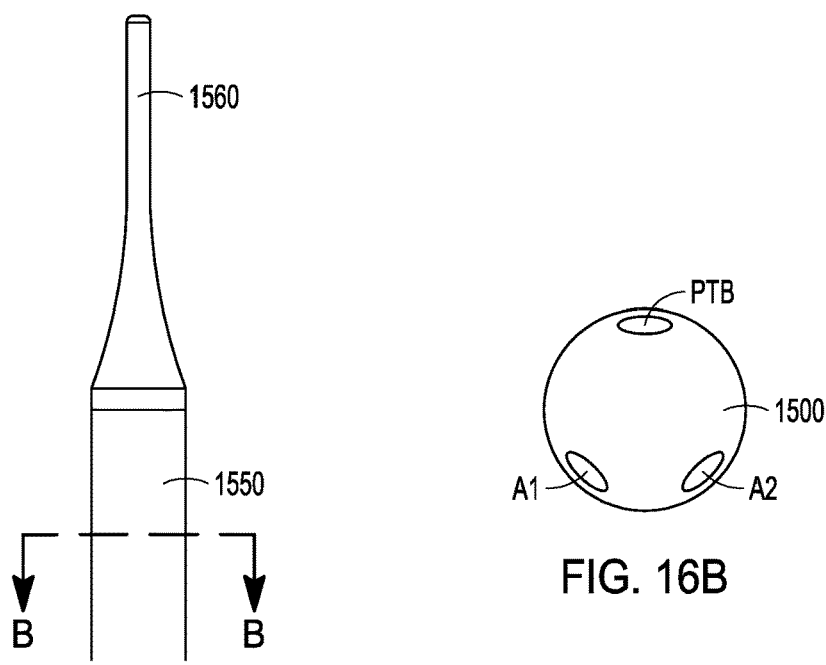
FIG. 16A
FIG. 16B
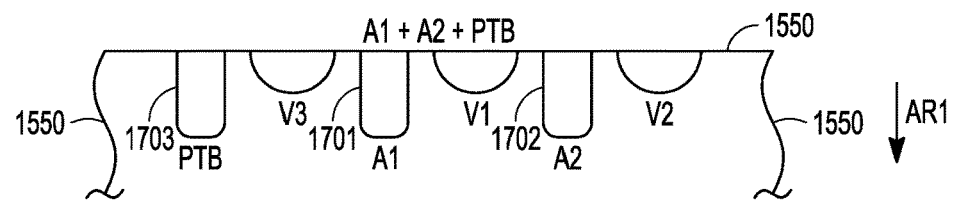
FIG. 17A
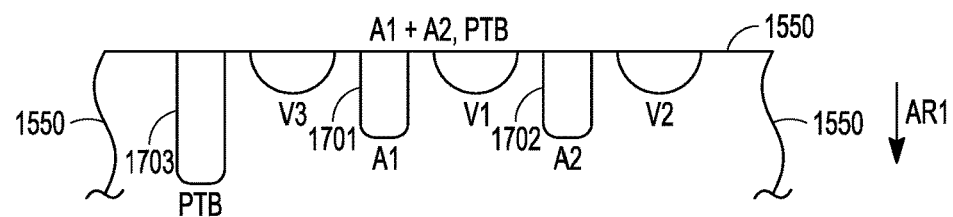
FIG. 17B
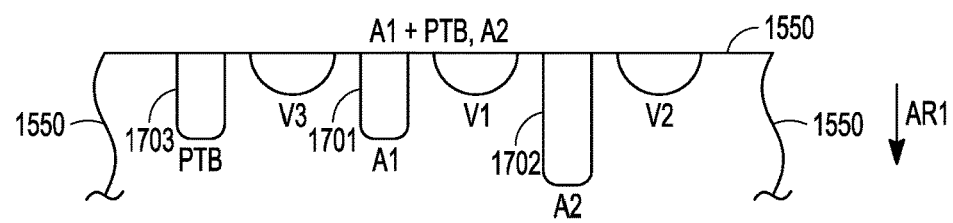
FIG. 17C

SEQUENTIALLY DEPLOYED TRANSCATHETER MITRAL VALVE PROSTHESIS

CROSS-REFERENCE

This application claims priority to U.S. Provisional Patent Application No. 62/550,368 filed Aug. 25, 2017, the entire contents of which are incorporated herein by reference.

The subject matter of the present application is related to that of U.S. patent application Ser. No. 15/628,924 filed Jun. 21, 2017, now U.S. Pat. No. 10,537,422, which is a continuation of U.S. patent application Ser. No. 15/046,371 filed Feb. 17, 2017, now U.S. Pat. No. 9,713,529, which is a continuation of U.S. patent application Ser. No. 13/679,920 filed Nov. 16, 2012, now U.S. Pat. No. 9,308,087, which is a non-provisional of, and claims the benefit of U.S. Provisional Patent Application No. 61/563,156 filed Nov. 23, 2011; the entire contents of which are incorporated herein by reference.

The subject matter of the present application is related to that of U.S. patent application Ser. No. 13/096,572 filed Apr. 28, 2011, now U.S. Pat. No. 8,579,964, the entire contents of which are incorporated herein by reference.

BACKGROUND OF THE INVENTION

1. Field of the Invention

The present invention generally relates to medical devices and methods, and more particularly relates to the treatment of valve insufficiency, such as mitral insufficiency, also referred to as mitral regurgitation. The use of prosthetic valves delivered by traditional surgical implantation methods, by a less invasive percutaneous catheter, or by minimally invasive transapical methods are one possible treatment for valvar insufficiency (also referred to as regurgitation).

The heart of vertebrate animals is divided into four chambers, and is equipped with four valves (the mitral, aortic, pulmonary and tricuspid valves) that ensure that blood pumped by the heart flows in a forward direction through the cardiovascular system. The mitral valve of a healthy heart prevents the backflow of blood from the left ventricle into the left atrium of the heart, and comprises two flexible leaflets (anterior and posterior) that close when the left ventricle contracts. The leaflets are attached to a fibrous annulus, and their free edges are tethered by subvalvular chordae tendineae to papillary muscles in the left ventricle to prevent them from prolapsing into the left atrium during the contraction of the left ventricle.

Various cardiac diseases or degenerative changes may cause dysfunction in any of these portions of the mitral valve apparatus, causing the mitral valve to become abnormally narrowed or dilated, or to allow blood to leak (i.e. regurgitate) from the left ventricle back into the left atrium. Any such impairments compromise cardiac sufficiency, and can be debilitating or life threatening.

Numerous surgical methods and devices have accordingly been developed to treat mitral valve dysfunction, including open-heart surgical techniques for replacing, repairing or re-shaping the native mitral valve apparatus, and the surgical implantation of various prosthetic devices such as annuloplasty rings to modify the anatomy of the native mitral valve. More recently, less invasive transcatheter techniques for the delivery of replacement mitral valve assemblies have been developed. In such techniques, a prosthetic valve is generally mounted in a crimped stale on the end of a flexible catheter and advanced through a blood vessel or the body of the patient until the valve reaches the implantation site. The prosthetic valve is then expanded to its functional size at the site of the defective native valve.

While these devices and methods are promising treatments for valvar insufficiency, they can be difficult to deliver, expensive to manufacture, or may not be indicated for all patients. Therefore, it would be desirable to provide improved devices and methods for the treatment of valvar insufficiency such as mitral insufficiency. At least some of these objectives will be met by the devices and methods disclosed below.

2. Description of the Background Art

By way of example, PCT international patent number PCT/US2008/054410 (published as PCT international publication no. WO2008/103722), the disclosure of which is hereby incorporated by reference, describes a transcatheter mitral valve prosthesis that comprises a resilient ring, a plurality of leaflet membranes mounted with respect to the ring so as to permit blood flow therethrough in one direction, and a plurality of tissue-engaging positioning elements movably mounted with respect to the ring and dimensioned to grip the anatomical structure of the heart valve annulus, heart valve leaflets, and/or heart wall. Each of the positioning elements defines respective proximal, intermediate, and distal tissue engaging regions cooperatively configured and dimensioned to simultaneously engage separate corresponding areas of the tissue of an anatomical structure, and may include respective first, second, and third elongate tissue-piercing elements. The valve prosthesis may also include a skirt mounted with respect to the resilient ring for sealing a periphery of the valve prosthesis against a reverse flow of blood around the valve prosthesis. In some embodiments, the skirt extends both above and below the resilient ring so that the valve prosthesis can seal against tissue both above and below the flexible ring at the valve annulus.

PCT international patent number PCT/US2009/041754 (published as PCT international publication no. WO2009/134701), the disclosure of which is hereby incorporated by reference, describes a prosthetic mitral valve assembly that comprises an anchor or outer support frame with a flared upper end and a tapered portion to fit the contours of the native mitral valve, and a tissue-based one-way valve mounted therein. The assembly is adapted to expand radially outwardly and into contact with the native heart tissue to create a pressure fit, and further includes tension members anchoring the leaflets of the valve assembly to a suitable location on the heart to function as prosthetic chordae tendineae.

Also known are prosthetic mitral valve assemblies that utilize a claw structure for attachment of the prosthesis to the heart (see, for example, U.S. patent publication no. US2007/0016286 to Hermann et al., the disclosure of which is hereby incorporated by reference), as are prosthetic mitral valve assemblies that rely on the application of axial rather than radial clamping forces to facilitate the self-positioning and self-anchoring of the prosthesis with respect to the native anatomical structure.

Also known are prosthetic valve devices which include anchoring means which engage the chordae tendinae such that the chordae tendinae are captured within the hooks of the anchoring means, engage and penetrate the valve annulus, engage and penetrate the papillary muscles on the ventricular side, and/or engage and penetrate other tissue such as the interventricular septum and the left ventricle muscle wall to fix the position of the prosthetic valve device (see, for example, U.S. patent publication no. US2006/0241745 to Solent, the disclosure of which is hereby incorporated by reference).

Also know are prosthetic valve devices which include an annular body to attach to the valve annulus as well as prosthetic valve tissue, a plurality of ventricular anchor members configured to clamp leaflet tissue and chordae between adjacent anchor members, and a plurality of atrial anchor members (see, for example, U.S. Pat. No. 9,125,738 to Figulla et al., the disclosure of which is hereby incorporated by reference). The positioning of the valve prosthesis with a catheter can be made in a procedure such that the anchor members are released from a first end of the catheter and then anchored and supported behind the natural valve leaflets and/or between the chordae. Then, the valve prosthesis including the annular body may be completely released such that the annular body can come to rest with its center approximately at the annulus of the valve to be replaced.

Another method which has been proposed as a treatment of mitral valve regurgitation is the surgical bow tie method, which recently has been adapted into a minimally invasive catheter based treatment where an implant is used to clip the valve leaflets together. This procedure is more fully disclosed in the scientific and patent literature, such as in U.S. Pat. No. 6,629,534 to St. Goar et al., the entire contents of which are incorporated herein by reference.

Other relevant publications include U.S. patent publication no. 2011/0015731 to Carpentier et al., WO2011/137531 to Lane et al., and 2013/075215 to Lane et al. While some of these devices and methods are promising, there still is a need for improved devices and methods that will further allow more accurate positioning of a prosthetic valve and that will also more securely anchor the valve in place. At least some of these objectives will be met by the exemplary embodiments disclosed herein.

SUMMARY OF THE INVENTION

The present invention generally relates to medical devices and methods, and more particularly prosthetic valves used to treat mitral regurgitation. While the present disclosure focuses on the use of a prosthetic valve for treating mitral regurgitation, this is not intended to be limiting. The prosthetic valves disclosed herein may also be used to treat other body valves including other heart valves or venous valves. Exemplary heart valves include the aortic valve, the tricuspid valve, or the pulmonary valve.

In a first aspect of the present invention, a method of delivering an implantable prosthetic valve to a patient's heart which has a mitral valve with an anterior leaflet and a posterior leaflet, comprises providing a prosthetic valve, wherein the prosthetic valve comprises an expandable frame having a first end, a second end opposite the first end, a first anterior tab on an anterior portion of the expandable frame, a posterior tab on a posterior portion of the expandable frame, and a ventricular skirt adjacent the first end of the expandable frame. The prosthetic valve has an expanded configuration for engaging the heart and a collapsed configuration. The prosthetic valve is delivered in the collapsed configuration to the patient's heart adjacent the mitral valve, and the first anterior tab is expanded radially outward such that a tip portion of the first anterior tab engages a first fibrous trigone on a first side of the anterior leaflet of the mitral valve. The anterior chordae tendineae adjacent the anterior leaflet are disposed between the first anterior tab and an outer anterior surface of the ventricular skirt. In other words, the first anterior tab advances under (toward the ventricle) and behind the anterior chordae tendinae adjacent the anterior leaflet. After radially expanding the first anterior tab, the posterior tab is radially expanded outward such that the posterior leaflet of the mitral valve and adjacent posterior chordae tendinae are disposed between the posterior tab and an outer posterior surface of the ventricular skirt. In other words, the posterior tab advances under (toward the ventricle) and behind the posterior chordae tendinae adjacent the posterior leaflet. After radially expanding the posterior tab, the ventricular skirt is radially expanded outward thereby engaging the anterior and posterior leaflets. The anterior leaflet and the adjacent anterior chordae tendinae are captured between the first anterior tab and the outer anterior surface of the ventricular skirt. The posterior leaflet and the adjacent posterior chordae tendinae are captured between the posterior tab and the posterior outer surface of the ventricular skirt.

In another aspect of the present invention, a method of delivering an implantable prosthetic valve to a patient's heart having a mitral valve with an anterior leaflet and a posterior leaflet, comprises providing a prosthetic valve, wherein the prosthetic valve comprises an expandable frame having a first end, a second end opposite the first end, a first anterior tab on an anterior portion of the expandable frame, a posterior tab on a posterior portion of the expandable frame, and a ventricular skirt adjacent the first end of the expandable frame. The prosthetic valve has an expanded configuration for engaging the heart and a collapsed configuration. The prosthetic valve is delivered in the collapsed configuration to the patient's heart adjacent the mitral valve. The first anterior tab is expanded radially outward such that a tip portion of the first anterior tab engages a first fibrous trigone on a first side of the anterior leaflet of the mitral valve. In other words, the first anterior tab advances under (toward the ventricle) and behind the anterior chordae tendinae adjacent the anterior leaflet. The anterior leaflet and adjacent anterior chordae tendineae are disposed between the first anterior tab and an outer anterior surface of the ventricular skirt. After radially expanding the first anterior tab, the ventricular skirt is radially expanded outward thereby engaging the anterior leaflet such that the anterior leaflet and the adjacent anterior chordae tendinae are captured between the first anterior tab and the outer anterior surface of the ventricular skirt. After radially expanding the ventricular skirt, the posterior tab is radially expanded outward such that the posterior leaflet of the mitral valve and adjacent posterior chordae tendineae are disposed and captured between the posterior tab and an outer posterior surface of the ventricular skirt. In other words, the posterior tab advances under (toward the ventricle) and behind the posterior chordae tendinae adjacent the posterior leaflet.

The method may further comprise providing a delivery catheter, wherein the prosthetic valve is releasably coupled thereto. Delivering the prosthetic valve may comprise transapical delivery of the prosthetic valve from a region outside the heart to the left ventricle of the heart, or the prosthetic valve may be delivered transseptally from the right atrium to the left atrium of the heart. Delivering the prosthetic valve may comprise positioning the prosthetic valve across the mitral valve so that the first end of the expandable frame is inferior to a portion of the mitral valve and the second end of the expandable frame is superior to a portion of the mitral valve.

Expanding the first anterior tab may comprise retracting a constraining sheath from the first anterior tab so that the first anterior tab is free to self-expand radially outward. The prosthetic valve may further comprise a second anterior tab on the anterior portion of the expandable frame, and the method may further comprise expanding the second anterior tab radially outward such that a tip portion of the second anterior tab engages a second fibrous trigone on a second side of the anterior leaflet opposite the first side of the anterior leaflet, in other words, second first anterior tab advances under (toward the ventricle) and behind the anterior chordae tendinae adjacent the anterior leaflet. The anterior leaflet and adjacent anterior chordae tendineae may be disposed between the second anterior tab and an outer surface of the ventricular skirt. The second anterior tab may expand radially outward concurrently with expansion of the first anterior tab. Prior to engaging the first fibrous trigone or the second fibrous trigone with the respective first or second anterior tab, and prior to disposing the anterior leaflet and the adjacent chordae tendineae between the first or second anterior tab and the outer surface of the ventricular skirt, the method may comprise partially expanding the first or the second anterior tab radially outward such that the first or the second anterior tab is transverse to a longitudinal axis of the prosthetic valve. Expanding the second anterior tab may comprise retracting a constraining sheath from the second anterior tab so that the second anterior tab is free to self-expand radially outward. The partial expansion may advance the tab under (toward the ventricle) the adjacent chordae tendinae and, in some cases, further behind the chordae tendinae.

In some embodiments, prior to disposing the posterior leaflet of the mitral valve and the adjacent posterior chordae tendineae between the posterior tab and the outer posterior surface of the ventricular skirt, the method may comprise partially expanding the posterior tab radially outward such that the posterior tab is transverse to a longitudinal axis of the prosthetic valve. After the anterior leaflet and the adjacent anterior chordae tendineae are disposed between the first anterior tab and the outer anterior surface of the ventricular skirt, the method may comprise partially expanding the posterior tab radially outward such that the posterior tab is transverse to a longitudinal axis of the prosthetic valve, and wherein the posterior tab is partially expanded without disposing the posterior leaflet of the mitral valve and the adjacent posterior chordae tendinae between the posterior tab and the outer posterior surface of the ventricular skirt.

Radially expanding the ventricular skirt may comprise retracting a constraining sheath from the ventricular skirt so that the ventricular skirt is free to self-expand radially outward. The ventricular skirt may comprise a plurality of barbs, and expanding the ventricular skirt may comprise anchoring the plurality of barbs into heart tissue. The prosthetic valve may further comprise a plurality of commissures, and expanding the ventricular skirt may displace the anterior and posterior mitral valve leaflets radially outward thereby preventing interference between the commissures and both of the anterior and posterior leaflets. Expanding the ventricular skirt may displace the anterior and posterior valve leaflets radially outward without contacting an inner wall of the left ventricle, and without obstructing the left ventricular outflow tract. Expanding the ventricular skirt may expand the ventricular skirt asymmetrically such that an anterior portion of the ventricular skirt is substantially flat, and a posterior portion of the ventricular skirt is cylindrically shaped.

The method may further comprise reducing or eliminating mitral regurgitation. In some embodiments, the prosthetic valve may carry a therapeutic agent, and the method may further comprise eluting the therapeutic agent from the prosthetic valve into adjacent tissue. The prosthetic valve may also comprise an alignment element. A second fibrous trigone is disposed on a second side of the anterior leaflet opposite the first side of the anterior leaflet, and the method may further comprise aligning the alignment element with an aortic root and disposing the alignment element between the first and second fibrous trigones. Aligning the alignment element may comprise rotating the prosthetic valve.

The prosthetic valve may further comprise a plurality of commissures with a covering disposed thereover whereby a plurality of prosthetic valve leaflets are formed, and the method may further comprise releasing the plurality of prosthetic valve leaflets from a delivery catheter. The plurality of prosthetic valve leaflets may form a tricuspid valve that has an open configuration and a closed configuration. The plurality of prosthetic valve leaflets may be disposed away from one another in the open configuration thereby permitting antegrade blood flow therethrough, and the plurality of prosthetic valve leaflets may engage one another in the closed configuration thereby substantially preventing retrograde blood flow therethrough.

The prosthetic valve may further comprise an atrial skirt, and the method may further comprise expanding the atrial skirt radially outward so as to lie over a superior surface of the mitral valve, and engaging the atrial skirt against the superior surface of the mitral valve. Expanding the atrial skirt may comprise retracting a constraining sheath from the atrial skirt so that the atrial skirt is free to self-expand radially outward. The prosthetic valve may be moved upstream or downstream relative to the mitral valve to ensure that the atrial skirt engages the superior surface of the mitral valve. Engaging the atrial skirt against the superior surface may seal the atrial skirt against the superior surface of the mitral valve to prevent or substantially prevent blood flow therebetween.

The prosthetic valve may further comprise an annular region, and the method may further comprise expanding the annular region radially outward so as to cover an annulus of the minal valve. Expanding the annular region may comprise retracting a constraining sheath from the annular region so that the annular region is free to self-expand radially outward. Expanding the annular region may comprise asymmetrically expanding the annular region such that an anterior portion of the annular region is substantially flat, and a posterior portion of the annular region is cylindrically shaped.

In another aspect of the present invention, a sequentially deployed prosthetic cardiac valve comprises a self-expanding frame having a first end, a second end opposite the first end, an atrial region near the second end, and a ventricular region near the first end. The self-expanding frame has an expanded configuration and a collapsed configuration. The expanded configuration is adapted to engage heart tissue, and the collapsed configuration is adapted to be delivered to a patient's heart. The prosthetic valve also includes a self-expanding atrial skirt disposed in the atrial region, a self-expanding ventricular skirt disposed in the ventricular region and a self-expanding annular region disposed between the atrial region and the ventricular region. A first self-expanding anterior tab is disposed on an anterior portion of the self-expanding frame in the ventricular region. A self-expanding posterior tab is disposed on a posterior portion of the self-expanding frame in the ventricular region.

A portion of the first self-expanding anterior tab and a portion of the self-expanding posterior tab partially self-expand radially outward when a constraint is removed therefrom. The first anterior tab fully self-expands radially outward before the posterior tab fully self-expands radially outward when the constraint is removed therefrom. The posterior tab fully self-expands radially outward before ventricular skirt self-expands when the constraint is removed therefrom, and the ventricular skirt fully expands last.

In another aspect of the present invention, a sequentially deployed prosthetic cardiac valve comprises a self-expanding frame having a first end, a second end opposite the first end, an atrial region near the second end, and a ventricular region near the first end. The self-expanding frame has an expanded configuration and a collapsed configuration. The expanded configuration is adapted to engage heart tissue, and the collapsed configuration is adapted to be delivered to a patient's heart. The prosthetic cardiac valve also comprises a self-expanding atrial skirt disposed in the atrial region, a self-expanding ventricular skirt disposed in the ventricular region, and a self-expanding annular region disposed between the atrial region and the ventricular region. A first self-expanding anterior tab is disposed on an anterior portion of the self-expanding frame in the ventricular region. A self-expanding posterior tab is disposed on a posterior portion of the self-expanding frame in the ventricular region. A portion of the first self-expanding anterior tab and a portion of the self-expanding posterior tab partially self-expand radially outward when a constraint is removed therefrom. The first anterior tab self-expands radially outward before the ventricular skirt self-expands radially outward when the constraint is removed therefrom. The ventricular skirt self-expands radially outward before the posterior tab finishes self-expanding, and the posterior tab finishes self-expanding after the ventricular skirt self-expands.

At least a portion of the atrial skirt may be covered with tissue or a synthetic material. The atrial skirt may have a collapsed configuration and an expanded configuration. The collapsed configuration may be adapted for delivery to a patient's heart, and the expanded configuration may be radially expanded relative to the collapsed configuration and may be adapted to lie over a superior surface of the patient's native mitral valve, thereby anchoring the atrial skirt against a portion of the left atrium. The atrial skirt may comprise one or more radiopaque markers and may comprise a plurality of axially oriented struts connected together with a connector element thereby forming interconnected struts into a series of peaks and valleys. After self-expansion of the atrial skirt, the atrial skirt may form a flanged region adjacent the second end of the self-expanding frame. Also after self-expansion, the atrial skirt may have an asymmetrically D-shaped cross-section having a substantially flat anterior portion, and a cylindrically shaped posterior portion. The prosthetic valve may further comprise an alignment element coupled to an anterior portion of the atrial skirt, and the alignment element may be aligned with an aortic root of a patient's heart and may be disposed between two fibrous trigones of an anterior leaflet of the patient's mitral valve.

At least a portion of the annular region may be covered with tissue or a synthetic material. The annular region may have a collapsed configuration and an expanded configuration. The collapsed configuration may be adapted for delivery to the patient's heart, and the expanded configuration may be radially expanded relative to the collapsed configuration and may be adapted to cover an annulus of a patient's native mitral valve. After self-expanding, the annular region may have an asymmetrically D-shaped cross-section having a substantially flat anterior portion, and a cylindrically shaped posterior portion. The annular region may comprise a plurality of axially oriented struts connected together with a connector element, and the plurality of interconnected struts may form a series of peaks and valleys. One or more of the plurality of axially oriented struts may comprise one or more suture holes extending therethrough, and the suture holes may be sized to receive a suture.

At least a portion of the ventricular skirt may be covered with tissue or a synthetic material. After self-expanding, the ventricular skirt may comprise an asymmetrically D-shaped cross-section having a substantially flat anterior portion, and a cylindrically shaped posterior portion. The ventricular skirt may have a collapsed configuration and an expanded configuration. The collapsed configuration may be adapted for delivery to the patient's heart, and the expanded configuration may be radially expanded relative to the collapsed configuration and may be adapted to displace native mitral valve leaflets radially outward.

The first anterior tab may have a tip portion adapted to engage a first fibrous trigone on a first side of an anterior leaflet of a patient's mitral valve, and the first anterior tab may also be adapted to capture the anterior leaflet and adjacent chordae tendineae between the first anterior tab and an outer anterior surface of the ventricular skirt. The prosthetic cardiac valve may further comprise a second self-expanding anterior tab disposed on the anterior portion of the self-expanding frame in the ventricular region. The second anterior tab may have a tip portion adapted to engage a second fibrous trigone on a second side of the anterior leaflet of the patient's mitral valve opposite the first side of the anterior leaflet. The second anterior tab may be adapted to capture the anterior leaflet and adjacent chordae tendineae between the second anterior tab and the outer surface of the ventricular skirt. The first or the second anterior tabs may have a cover disposed thereover that increases the contact area between the tab and the cardiac tissue. The cover may include a fabric disposed over a polymer tab that is coupled to the first or second tab. The posterior tab may be adapted to being anchored over a posterior leaflet of the patient's mitral valve, such that the posterior tab is seated between the posterior leaflet and a ventricular wall of a patient's heart. The posterior tab may comprise a plurality of struts, and adjacent struts may be coupled together to form a plurality of expandable hinged joints. Upon radial expansion of the posterior tab, the plurality of struts may move away from one another thereby opening the hinged joints forming an elongate horizontal section which allows engagement and anchoring of the posterior tab with the sub-annular region between the posterior leaflet and the ventricular wall. Thus, the elongate horizontal section contacts a larger region of the sub-annular region as compared with a posterior tab that only has a tapered tip formed from a single hinge between struts. The ventricular skirt may further comprise a plurality of barbs coupled thereto. The plurality of barbs may be adapted to anchor the ventricular skirt into heart tissue. The ventricular skirt may also comprise a plurality of struts connected together with a connector element, and the plurality of interconnected struts may form a series of peaks and valleys. One or more of the struts may comprise one or more suture holes extending therethrough, the suture holes sized to receive a suture.

The prosthetic cardiac valve may further comprise a plurality of prosthetic valve leaflets. Each of the leaflets may have a first end and a free end, and the first end may be coupled with the self-expanding frame and the free end may be opposite of the first end. The prosthetic valve leaflets may have an open configuration in which the free ends of the prosthetic valve leaflets are disposed away from one another to allow antegrade blood flow therepast. The prosthetic valve leaflets may have a closed configuration in which the free ends of the prosthetic valve leaflets engage one another and substantially prevent retrograde blood flow therepast. The plurality of prosthetic valve leaflets may form a tricuspid valve. At least a portion of one or more prosthetic valve leaflets may comprise tissue or a synthetic material. One or more of the prosthetic valve leaflets may comprise a commissure post having a commissure tab, and the commissure tab may be adapted to be releasably engaged with a delivery device. The prosthetic cardiac valve may carry a therapeutic agent that is adapted to being eluted therefrom.

In still another aspect of the present invention, a delivery system for delivering a prosthetic cardiac valve to a patient's heart having a mitral valve with an anterior leaflet and a posterior leaflet, comprises a prosthetic cardiac valve, an inner guidewire shaft having a lumen extending therethrough, where the lumen is sized to slidably receive a guidewire, and a distal tissue penetrating tip coupled to a distal portion of the inner guidewire shaft. The distal tip is adapted to pass through and expand tissue in the heart, and a continuous flared region couples the inner guidewire shaft with the distal tip. The continuous flared region is configured to support the prosthetic cardiac valve thereby reducing or eliminating unwanted bending of the prosthetic cardiac valve. The delivery system also comprises a hub shaft concentrically disposed over the inner guidewire shaft. The prosthetic cardiac valve is releasably coupled to a distal portion of the hub shaft. A bell shaft is slidably and concentrically disposed over the hub shaft, and an outer sheath is slidably and concentrically disposed over the bell shaft. The prosthetic cardiac valve is housed in the outer sheath in a radially collapsed configuration. The delivery system also has a handle near a proximal end of the delivery system. The handle comprises an actuator mechanism adapted to advance and retract the bell shaft and the sheath. Proximal retraction of the outer sheath relative to the bell shaft may remove a constraint from the prosthetic cardiac valve thereby allowing the prosthetic cardiac valve to self-expand into engagement with the patient's mitral valve. The prosthetic cardiac valve may comprise a plurality of commissure posts, and the commissure posts may be releasably coupled with a distal portion of the hub shaft. Proximal retraction of the bell shaft relative to the hub shaft allows the commissure posts to uncouple from the hub shaft. The actuator mechanism may comprise a rotatable wheel.

Another aspect of the present invention provides an implantable prosthetic valve, a method of delivering the implantable prosthetic valve to a patient's heart, and/or a system for delivering the implantable prosthetic valve. The patient's heart has a mitral valve with an anterior leaflet and a posterior leaflet. The prosthetic valve may be provided. The prosthetic valve may comprise an expandable frame having a first end, a second end opposite the first end, a first anterior tab on an anterior portion of the expandable frame, a posterior tab on a posterior portion of the expandable frame, and a ventricular skirt adjacent the first end of the expandable frame. The prosthetic valve may have an expanded configuration for engaging the heart and a collapsed configuration. The prosthetic valve may be delivered in the collapsed configuration to the patient's heart adjacent the mitral valve. The first anterior tab may be expanded radially outward such that a tip portion of the first anterior tab engages a first fibrous trigone on a first side of the anterior leaflet of the mitral valve. The anterior leaflet and adjacent anterior chordae tendinae may be disposed between the first anterior tab and an outer anterior surface of the ventricular skirt. Concurrently with expanding the first anterior tab, the posterior tab may be radially expanded outward such that the posterior leaflet of the mitral valve and adjacent posterior chordae tendinae are disposed between the posterior tab and an outer posterior surface of the ventricular skirt. The ventricular skirt may be radially expanded outward thereby engaging the anterior and posterior leaflets. The anterior leaflet and the adjacent anterior chordae tendinae may be captured between the first anterior tab and the outer anterior surface of the ventricular skirt. The posterior leaflet and the adjacent posterior chordae tendinae may be captured between the posterior tab and the posterior outer surface of the ventricular skirt.

The prosthetic valve may further comprise a second anterior tab on the anterior portion of the expandable frame, and the second anterior tab may be expanded radially outward such that a tip portion of the second anterior tab engages a second fibrous trigone on a second side of the anterior leaflet opposite the first side of the anterior leaflet. The anterior leaflet and adjacent anterior chordae tendinae may be disposed between the second anterior tab and an outer surface of the ventricular skirt. The first and second anterior tabs and the posterior tab may each extend from a base proximal to the annular region to a free end arranged at an axial position along the frame in the ventricular region. The axial position of the free end of the tabs, and therefore the length of each of the tabs, may vary in different embodiments and the lengths of the tabs may differ from one another. The varying axial position of the free ends of the tabs may enable the deployment sequence of the tabs to be controlled as the sheath is retracted. For example, the second anterior tab may be longer than the first anterior tab and the posterior tab, such that the free end of the second anterior tab is axially positioned further from the annular region than the free ends of the first anterior tab and the posterior tab. In this case, the second anterior tab may be radially expanded outward after the first anterior tab and the posterior tab are radially expanded outward. In other examples, the lengths and axial position of the free end of the tabs may be controlled such that the second anterior tab is radially expanded outward before the first anterior tab and the posterior tab are radially expanded outward, or concurrently with the first anterior tab and the posterior tab being radially expanded outward. The ventricular skirt may be radially expanded outward before the second anterior tab is radially expanded outward, after the second anterior tab is radially expanded outward, or concurrently with the second anterior tab being radially expanded outward.

To radially expand the second anterior tab outward, a constraining sheath may be retracted from the second anterior tab so that the second anterior tab is free to radially self-expand outward.

Prior to the anterior leaflet and the adjacent anterior chordae tendineae being disposed between the second anterior tab and the outer anterior surface of the ventricular skirt, the second anterior tab may be partially expanded radially outward such that the first anterior tab is transverse to a longitudinal axis of the prosthetic valve. The second anterior tab may be partially expanded radially outward by partially retracting the constraining sheath from the second anterior tab so that the second anterior tab is partially free to self-expand radially outward.

Prior to the anterior leaflet and the adjacent anterior chordae tendineae being disposed between the first anterior tab and the outer anterior surface of the ventricular skirt, the first anterior tab may be partially expanded radially outward such that the first anterior tab is transverse to a longitudinal axis of the prosthetic valve. The first anterior tab may be partially expanded radially outward by partially retracting the constraining sheath from the first anterior tab so that the first anterior tab is partially free to self-expand radially outward.

Prior to disposing the posterior leaflet of the mitral valve and the adjacent posterior chordae tendineae between the posterior tab and the outer posterior surface of the ventricular skirt, the posterior tab may be partially expanded radially outward such that the posterior tab is transverse to a longitudinal axis of the posterior valve. The posterior tab may be partially expanded radially outward by partially retracting the constraining sheath from the posterior tab so that the posterior tab is partially free to self-expand radially outward.

The first anterior tab may be expanded by retracting the constraining sheath from the first anterior tab so that the first anterior tab is free to self-expand radially outward. The posterior tab may be expanded by retracting the constraining sheath from the posterior tab so that the posterior tab is free to self-expand radially outward.

The ventricular skirt may be radially expanded outward before the first anterior tab and posterior tab are radially expanded outward, after the first anterior tab and posterior tab are radially expanded outward, or concurrently with the first anterior tab and posterior tab being radially expanded outward.

The ventricular skirt may be radially expanded by retracting the constraining sheath from the ventricular skirt so that the ventricular skirt is free to self-expand radially outward. The ventricular skirt may be radially expanded in any order, for example, before any combination of the anterior and posterior tabs, concurrently with at least any one of the anterior and posterior tabs, between at least any two of the anterior and posterior tabs, or after any combination of the anterior and posterior tabs.

A delivery catheter which the prosthetic valve is releasably coupled thereto may be further provided.

The prosthetic valve may be delivered transapically from a region outside the heart to the left ventricle of the heart. Alternatively, the prosthetic valve may be delivered transseptally from the right atrium to the left atrium of the body.

To deliver the prosthetic valve, the prosthetic valve may be positioned across the mitral valve so that the first end of the expandable frame is inferior to a portion of the mitral valve and the second end of the expandable frame is superior to a position of the mitral valve.

The ventricular skirt may comprise a plurality of barbs, and in expanding the ventricular skirt, the plurality of barbs may be anchored into heart tissue.

The prosthetic valve may further comprise a plurality of commissures, and in expanding the ventricular skirt, the anterior and posterior mitral valve leaflets may be displaced radially outward thereby preventing interference between the commissures and both of the anterior and posterior leaflets. Expanding the ventricular skirt may displace the anterior and posterior valve leaflets radially outward without contacting an inner wall of the left ventricle, and without obstructing a left ventricular outflow tract, in radially expanding the ventricular skirt, the ventricular skirt may be expanded asymmetrically such that an anterior portion of the ventricular skirt is substantially flat, and a posterior portion of the ventricular skirt is cylindrically shaped.

Mitral regurgitation may be reduced or eliminated, such as by the implanted prosthetic valve.

The prosthetic valve may carry a therapeutic agent, and the therapeutic agent may be eluted from the prosthetic valve into adjacent tissue.

The prosthetic valve may comprise an alignment element, and a second fibrous trigone may be disposed on a second side of the anterior leaflet opposite the first side of the anterior leaflet. The alignment element may be aligned with an aortic root and the alignment element may be disposed between the first and second fibrous trigones. To align the alignment element, the prosthetic valve may be rotated.

The prosthetic valve may further comprise a plurality of commissures with a covering disposed thereover whereby a plurality of prosthetic valve leaflets are formed. The plurality of prosthetic valve leaflets may be released from a delivery catheter. The plurality of prosthetic valve leaflets may form a tricuspid valve, the tricuspid valve having an open configuration and a closed configuration. The plurality of prosthetic valve leaflets may be disposed away from one another in the open configuration thereby permitting antegrade blood flow therethrough. The plurality of prosthetic valve leaflets may engage one another in the closed configuration thereby substantially preventing retrograde blood flow therethrough.

The prosthetic valve may further comprise an atrial skirt. The atrial skirt may be expanded radially outward so as to lie over a superior surface of the mitral valve, and the atrial skirt may be engaged against the superior surface of the mitral valve. The atrial skirt may be expanded by retracting the constraining sheath from the atrial skirt so that the atrial skirt is free to self-expand radially outward. The prosthetic valve may be moved upstream or downstream relative to the mitral valve to ensure that the atrial skirt engages the superior surface of the mitral valve. The atrial skirt may be engaged against the superior surface to seal the atrial skirt against the superior surface of the mitral valve to prevent or substantially prevent blood flow therebetween.

The prosthetic valve may further comprise an annular region. The annular region may be expanded radially outward so as to cover an annulus of the mitred valve. To expand the annular region, a constraining sheath may be retracted from the annular region so that the annular region is free to self-expand radially outward. To expand the annular region, the annular region may be asymmetrically expanded such that an anterior portion of the annular region is substantially flat, and a posterior portion of the annular region is cylindrically shaped.

Another aspect of the present invention provides an implantable prosthetic valve, a method of delivering m implantable prosthetic valve to a patient's heart, and/or a system for delivering the implantable prosthetic valve. The patient's heart has a mitral valve with an anterior leaflet and a posterior leaflet. The prosthetic valve may be provided. The prosthetic valve may comprise an expandable frame having a first end, a second end opposite the first end, a first anterior tab on an anterior portion of the expandable frame, a posterior tab on a posterior portion of the expandable frame, and a ventricular skirt adjacent the first end of the expandable frame. The prosthetic valve may have an expanded configuration for engaging the heart and a collapsed configuration. The prosthetic valve may be delivered in the collapsed configuration to the patient's heart adjacent the mitral valve. The first anterior tab may be expanded radially outward such that a tip portion of the first anterior tab engages a first fibrous trigone on a first side of the anterior leaflet of the mitral valve. The anterior leaflet and adjacent anterior chordae tendinae may be disposed between the first anterior tab and an outer anterior surface of the ventricular skirt. After radially expanding the first anterior tab, the posterior tab may he radially expanded outward such that the posterior leaflet of the mitral valve and adjacent posterior chordae tendinae are disposed between the posterior tab and an outer posterior surface of the ventricular skirt. The ventricular skirt may be radially expanded outward thereby engaging the anterior and posterior leaflets. The anterior leaflet and the adjacent anterior chordae tendinae may be captured between the first anterior tab and the outer anterior surface of the ventricular skirt. The posterior leaflet and the adjacent posterior chordae tendinae may be captured between the posterior tab and the posterior outer surface of the ventricular skirt.

The prosthetic valve may further comprise a second anterior tab on the anterior portion of the expandable frame, and the second anterior tab may be expanded radially outward such that a tip portion of the second anterior tab engages a second fibrous trigone on a second side of the anterior leaflet opposite the first side of the anterior leaflet. The anterior leaflet and adjacent anterior chordae tendinae may be disposed between the second anterior tab and an outer surface of the ventricular skirt. The second anterior tab may be radially expanded outward after the first anterior tab is radially expanded outward and before the posterior tab is radially expanded outward, before the first anterior tab and the posterior tab are radially expanded outward, or after the first anterior tab and the posterior tab are radially expanded outward. The ventricular skirt may be radially expanded outward before the second anterior tab is radially expanded outward, after the second anterior tab is radially expanded outward, or concurrently with the second anterior tab being radially expanded outward.

To radially expand the second anterior tab outward, a constraining sheath may be retracted from the second anterior tab so that the second anterior tab is free to radially self-expand outward.

Prior to the anterior leaflet and the adjacent anterior chordae tendineae being disposed between the second anterior tab and the outer anterior surface of the ventricular skirt, the second anterior tab may be partially expanded radially outward such that the first anterior tab is transverse to a longitudinal axis of the prosthetic valve. The second anterior tab may be partially expanded radially outward by partially retracting the constraining sheath from the second anterior tab so that the second anterior tab is partially free to self-expand radially outward.

Prior to the anterior leaflet and the adjacent anterior chordae tendineae being disposed between the first anterior tab and the outer anterior surface of the ventricular skirt, the first anterior tab may be partially expanded radially outward such that the first anterior tab is transverse to a longitudinal axis of the prosthetic valve. The first anterior tab may be partially expanded radially outward by partially retracting the constraining sheath from the first anterior tab so that the first anterior tab is partially free to self-expand radially outward.

Prior to disposing the posterior leaflet of the mitral valve and the adjacent posterior chordae tendineae between the posterior tab and the posterior outer surface of the ventricular skirt, the posterior tab may be partially expanded radially outward such that the posterior tab is transverse to a longitudinal axis of the posterior valve. The posterior tab may be partially expanded radially outward by partially retracting the constraining sheath from the posterior tab so that the posterior tab is partially free to self-expand radially outward.

The first anterior tab may be expanded by retracting the constraining sheath from the first anterior tab so that the first anterior tab is free to self-expand radially outward. The posterior tab may be expanded by retracting the constraining sheath from the posterior tab so that the posterior tab is free to self-expand radially outward.

The ventricular skirt may be radially expanded outward before the first anterior tab and posterior tab are radially expanded outward, after the first anterior tab and posterior tab are radially expanded outward, or after the first anterior tab is radially expanded after and before the posterior tab is radially expanded outward.

The ventricular skirt may be expanded radially expanded outward concurrently with the first anterior tab or concurrently with the posterior tab. The ventricular skirt may be radially expanded by retracting the constraining sheath from the ventricular skirt so that the ventricular skirt is free to self-expand radially outward. The ventricular skirt may be radially expanded in any order, for example, before any combination of the anterior and posterior tabs, concurrently with at least any one of the anterior and posterior tabs between at least any two of the anterior and posterior tabs, or after any combination of the anterior and posterior tabs.

A delivery catheter which the prosthetic valve is releaseably coupled thereto may be further provided.

The prosthetic valve may be delivered transapically from a region outside the heart to the left ventricle of the heart. Alternatively, the prosthetic valve may be delivered transseptally from the right atrium to the left atrium of the body.

To deliver the prosthetic valve, the prosthetic valve may be positioned across the mitral valve so that the first end of the expandable frame is inferior to a portion of the mitral valve and the second end of the expandable frame is superior to a position of the mitral valve.

The ventricular skirt may comprise a plurality of barbs, and in expanding the ventricular skirt, the plurality of barbs may be anchored into heart tissue.

The prosthetic valve may further comprise a plurality of commissures, and in expanding the ventricular skirt, the anterior and posterior mitral valve leaflets may be displaced radially outward thereby preventing interference between the commissures and both of the anterior and posterior leaflets. Expanding the ventricular skirt may displace the anterior and posterior valve leaflets radially outward without contacting an inner wall of the left ventricle, and without obstructing a left ventricular outflow tract, in radially expanding the ventricular skirt, the ventricular skirt may be expanded asymmetrically such that an anterior portion of the ventricular skirt is substantially flat, and a posterior portion of the ventricular skirt is cylindrically shaped.

Mitral regurgitation may be reduced or eliminated, such as by the implanted prosthetic valve.

The prosthetic valve may catty a therapeutic agent, and the therapeutic agent may be eluted from the prosthetic valve into adjacent tissue.

The prosthetic valve may comprise an alignment element, and a second fibrous trigone may be disposed on a second side of the anterior leaflet opposite the first side of the anterior leaflet. The alignment element may be aligned with an aortic root and the alignment element may be disposed between the first and second fibrous trigones. To align the alignment element, the prosthetic valve may be rotated.

The prosthetic valve may further comprise a plurality of commissures with a covering disposed thereover whereby a plurality of prosthetic valve leaflets are formed. The plurality of prosthetic valve leaflets may be released from a delivery catheter. The plurality of prosthetic valve leaflets may form a tricuspid valve, the tricuspid valve having an open configuration and a closed configuration. The plurality of prosthetic valve leaflets may be disposed away from one another in the open configuration thereby permitting antegrade blood flow therethrough. The plurality of prosthetic valve leaflets may engage one another in the closed configuration thereby substantially preventing retrograde blood flow therethrough.

The prosthetic valve may further comprise an atrial skirt. The atrial skirt may be expanded radially outward so as to lie over a superior surface of the mitral valve, and the atrial skirt may be engaged against the superior surface of the mitral valve. The atrial skirt may be expanded by retracting the constraining sheath from the atrial skirt so that the atrial skirt is free to self-expand radially outward. The prosthetic valve may be moved upstream or downstream relative to the mitral valve to ensure that the atrial skirt engages the superior surface of the mitral valve. The atrial skirt may be engaged against the superior surface to seal the atrial skirt against the superior surface of the mitral valve to prevent or substantially prevent blood flow therebetween.

The prosthetic valve may further comprise an annular region. The annular region may be expanded radially outward so as to cover an annulus of the mitral valve. To expand the annular region, a constraining sheath may be retracted from the annular region so that the annular region is free to self-expand radially outward. To expand the annular region, the annular region may be asymmetrically expanded such that an anterior portion of the annular region is substantially flat, and a posterior portion of the annular region is cylindrically shaped.

Another aspect of the present invention provides an implantable prosthetic valve, a method of delivering the implantable prosthetic valve to a patient's heart, and/or a system for delivering the implantable prosthetic valve. The patient's heart having a mitral valve with an anterior leaflet and a posterior leaflet. The prosthetic valve may be provided. The prosthetic valve may comprise an expandable frame having a first end, a second end opposite the first end, a first anterior tab on an anterior portion of the expandable frame, a posterior tab on a posterior portion of the expandable frame, and a ventricular skirt adjacent the first end of the expandable frame. The prosthetic valve may have an expanded configuration for engaging the heart and a collapsed configuration. The prosthetic valve may be delivered in the collapsed configuration to the patient's heart adjacent the mitral valve. The first anterior tab may be expanded radially outward such that a tip portion of the first anterior tab engages a first fibrous trigone on a first side of the anterior leaflet of the mitral valve. The anterior leaflet and adjacent anterior chordae tendinae may be disposed between the first anterior tab and an outer anterior surface of the ventricular skirt. Prior to radially expanding the first anterior tab, the posterior tab may be radially expanded outward such that the posterior leaflet of the mitral valve and adjacent posterior chordae tendinae are disposed between the posterior tab and an outer posterior surface of the ventricular skirt. The ventricular skirt may be radially expanded outward thereby engaging the anterior and posterior leaflets. The anterior leaflet and the adjacent anterior chordae tendinae may be captured between the first anterior tab and the outer anterior surface of the ventricular skirt. The posterior leaflet and the adjacent posterior chordae tendinae may be captured between the posterior tab and the posterior outer surface of the ventricular skirt.

The prosthetic valve may further comprise a second anterior tab on the anterior portion of the expandable frame. The second anterior tab may be expanded radially outward such that a tip portion of the second anterior tab engages a second fibrous trigone on a second side of the anterior leaflet opposite the first side of the anterior leaflet. The anterior leaflet and adjacent anterior chordae tendinae may be disposed between the second anterior tab and an outer surface of the ventricular skirt. The second anterior tab may be radially expanded outward after the first anterior tab and the posterior tab are radially expanded outward, before the first anterior tab and the posterior tab are radially expanded outward, or before the first anterior tab is radially expanded outward and after the posterior tab is radially expanded outward. The ventricular skirt may be radially expanded outward before the second anterior tab is radially expanded outward, after the second anterior tab is radially expanded outward, or concurrently with the second anterior tab being radially expanded outward.

To radially expand the second anterior tab outward, a constraining sheath may be retracted from the second anterior tab so that the second anterior tab is free to radially self-expand outward.

Prior to the anterior leaflet and the adjacent anterior chordae tendineae being disposed between the second anterior tab and the outer anterior surface of the ventricular skirt, the second anterior tab may be partially expanded radially outward such that the first anterior tab is transverse to a longitudinal axis of the prosthetic valve. The second anterior tab may be partially expanded radially outward by partially retracting the constraining sheath from the second anterior tab so that the second anterior tab is partially free to self-expand radially outward.

Prior to the anterior leaflet and the adjacent anterior chordae tendineae being disposed between the first anterior tab and the outer anterior surface of the ventricular skirt, the first anterior tab may be partially expanded radially outward such that the first anterior tab is transverse to a longitudinal axis of the prosthetic valve. The first anterior tab may be partially expanded radially outward by partially retracting the constraining sheath from the first anterior tab so that the first anterior tab is partially free to self-expand radially outward.

Prior to disposing the posterior leaflet of the mitral valve and the adjacent posterior chordae tendineae between the posterior tab and the outer posterior surface of the ventricular skirt, the posterior tab may be partially expanded radially outward such that the posterior tab is transverse to a longitudinal axis of the posterior valve. The posterior tab may be partially expanded radially outward by partially retracting the constraining sheath from the posterior tab so that the posterior tab is partially free to self-expand radially outward.

The first anterior tab may be expanded by retracting the constraining sheath from the first anterior tab so that the first anterior tab is free to self-expand radially outward. The posterior tab may be expanded by retracting the constraining sheath from the posterior tab so that the posterior tab is free to self-expand radially outward.

The ventricular skirt may be radially expanded outward before the first anterior tab and posterior tab are radially expanded outward, after the first anterior tab and posterior tab are radially expanded outward, or concurrently with the first anterior tab and posterior tab being radially expanded outward.

The ventricular skirt may be radially expanded by retracting the constraining sheath from the ventricular skirt so that the ventricular skirt is free to self-expand radially outward. The ventricular skirt may be radially expanded in any order, for example, before any combination of the anterior and posterior tabs, concurrently with at least any one of the anterior and posterior tabs, between at least any two of the anterior and posterior tabs, or after any combination of the anterior and posterior tabs.

A delivery catheter which the prosthetic valve is releaseably coupled thereto may be further provided.

The prosthetic valve may be delivered transapically from a region outside the heart to the left ventricle of the heart. Alternatively, the prosthetic valve may be delivered transseptally from the right atrium to the left atrium of the body.

To deliver the prosthetic valve, the prosthetic valve may be positioned across the mitral valve so that the first end of the expandable frame is inferior to a portion of the mitral valve and the second end of the expandable frame is superior to a position of the mitral valve.

The ventricular skirt may comprise a plurality of barbs, and in expanding the ventricular skirt, the plurality of barbs may be anchored into heart tissue.

The prosthetic valve may further comprise a plurality of commissures, and in expanding the ventricular skirt, the anterior and posterior mitral valve leaflets may be displaced radially outward thereby preventing interference between the commissures and both of the anterior and posterior leaflets. Expanding the ventricular skirt may displace the anterior and posterior valve leaflets radially outward without contacting an inner wall of the left ventricle, and without obstructing a left ventricular outflow tract. In radially expanding the ventricular skirt, the ventricular skirt may be expanded asymmetrically such that an anterior portion of the ventricular skirt is substantially flat, and a posterior portion of the ventricular skirt is cylindrically shaped.

Mitral regurgitation may be reduced or eliminated, such as by the implanted prosthetic valve.

The prosthetic valve may carry a therapeutic agent, and tale therapeutic agent may be eluted from the prosthetic valve into adjacent tissue.

The prosthetic valve may comprise an alignment element, and a second fibrous trigone may be disposed on a second side of the anterior leaflet opposite the first side of the anterior leaflet. The alignment element may be aligned with an aortic root and the alignment element may be disposed between the first and second fibrous trigones. To align the alignment element, the prosthetic valve may be rotated.

The prosthetic valve may further comprise a plurality of commissures with a covering disposed thereover whereby a plurality of prosthetic valve leaflets are formed. The plurality of prosthetic valve leaflets may be released from a delivery catheter. The plurality of prosthetic valve leaflets may form a tricuspid valve, the tricuspid valve having an open configuration and a closed configuration. The plurality of prosthetic valve leaflets may be disposed away from one another in the open configuration thereby permitting antegrade blood flow therethrough. The plurality of prosthetic valve leaflets may engage one another in the closed configuration thereby substantially preventing retrograde blood flow therethrough.

The prosthetic valve may further comprise an atrial skirt. The atrial skirt may be expanded radially outward so as to lie over a superior surface of the mitral valve, and the atrial skirt may be engaged against the superior surface of the mitral valve. The atrial skirt may be expanded by retracting the constraining sheath from the atrial skirt so that the atrial skirt is free to self-expand radially outward. The prosthetic valve may be moved upstream or downstream relative to the mitral valve to ensure that the atrial skirt engages the superior surface of the mitral valve. The atrial skirt may be engaged against the superior surface to seal the atrial skirt against the superior surface of the mitral valve to prevent or substantially prevent blood flow therebetween.

The prosthetic valve may further comprise an annular region. The annular region may be expanded radially outward so as to cover an annulus of the mitral valve. To expand the annular region, a constraining sheath may be retracted from the annular region so that the annular region is free to self-expand radially outward. To expand the annular region, the annular region may be asymmetrically expanded such that an anterior portion of the annular region is substantially flat, and a posterior portion of the annular region is cylindrically shaped.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will he obtained by reference to the following detailed description that sets forth illustrative embodiments, in which the principles of the invention are utilized, and the accompanying drawings of which:

FIGS. 15A-15E schematically illustrate an exemplary method of deploying a prosthetic cardiac valve whereby the first and second anterior tabs are concurrently deployed, according to many embodiments.

FIGS. 15F-15L schematically illustrate an exemplary method of deploying a prosthetic cardiac valve whereby the first anterior tab is deployed before the second anterior tab, according to many embodiments.

FIG. 16A shows a prosthetic cardiac valve held within a constraining sheath, according to many embodiments.

FIG. 16B schematically illustrates a cross-section of the prosthetic cardiac calve of FIG. 16A taken along line B-B of FIG. 16B.

FIGS. 17A-17M schematically illustrate variations of different sequences for fully deploying a first anterior tab, a second anterior tab, and a posterior tab of a prosthetic cardiac valve, according to many embodiments.

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

Figure 1:
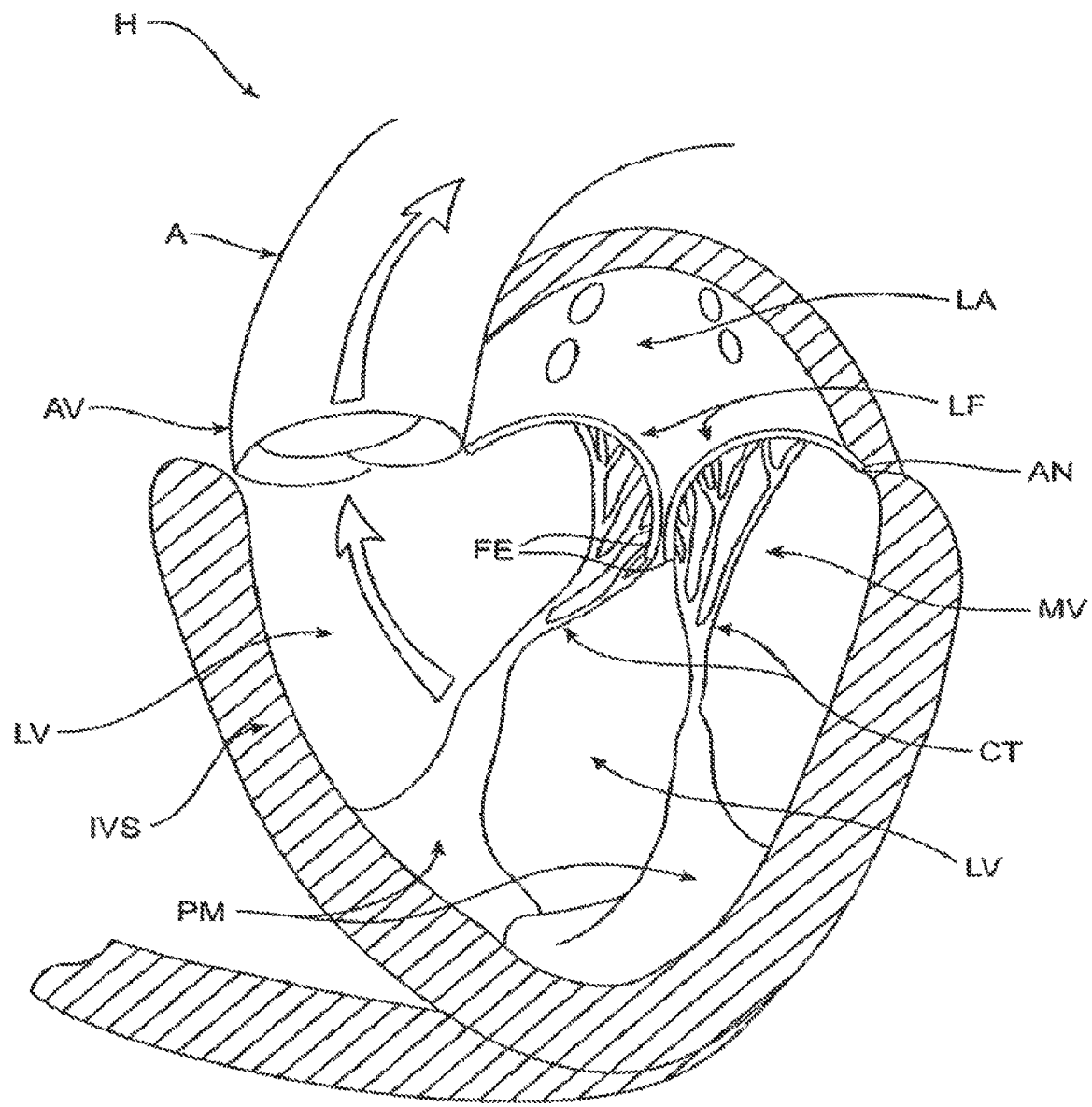
FIG. 1 is a schematic illustration of the left ventricle of a heart showing blood flow during systole with arrows.

Cardiac Anatomy. The left ventricle LV of a normal heart H in systole is illustrated in FIG. 1. The left ventricle LV is contracting and blood flows outwardly through the aortic valve AV, a tricuspid valve in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (also referred to herein as the chordae) which include a plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2:
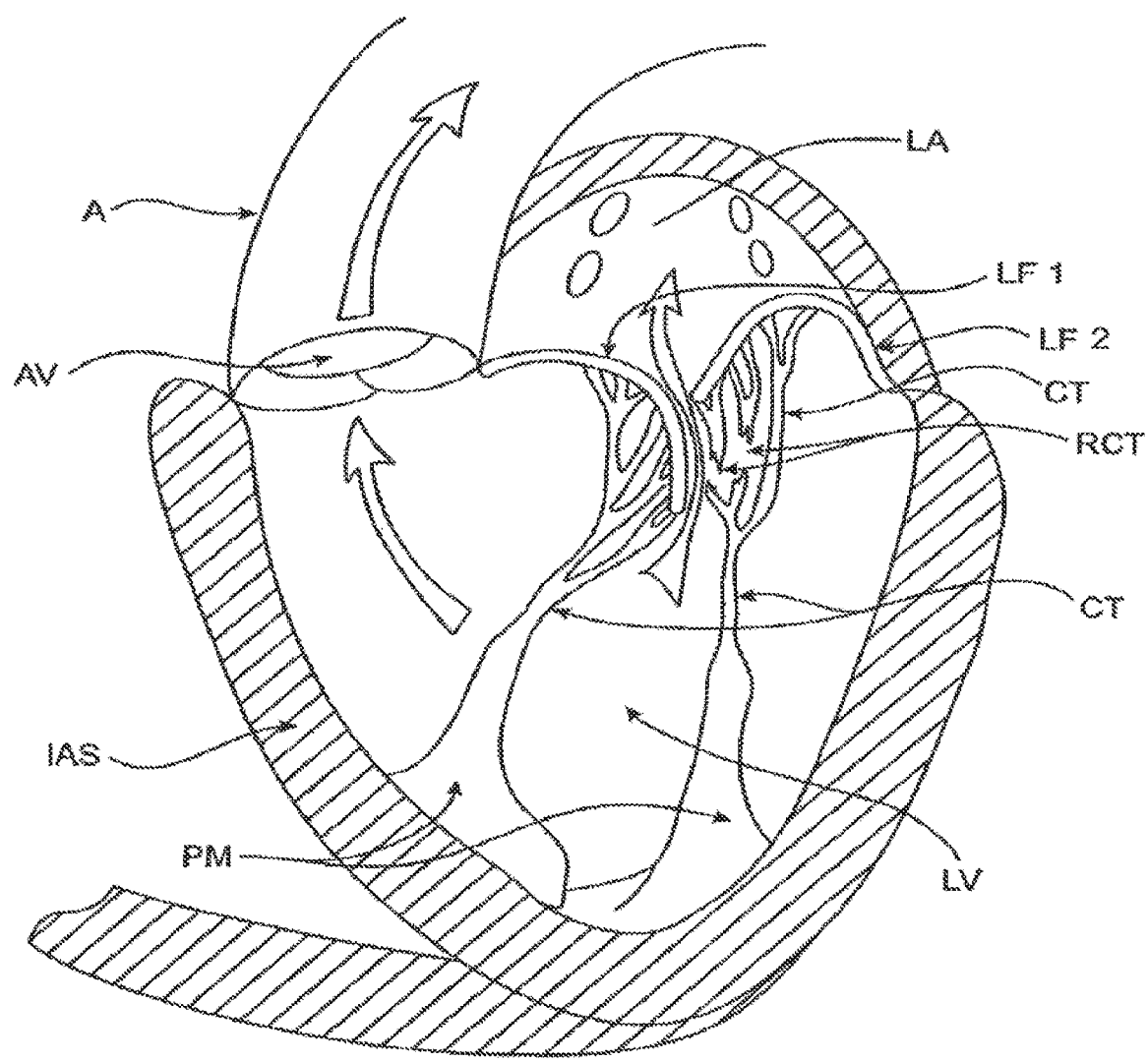
FIG. 2 is a schematic illustration of the left ventricle of a heart having prolapsed leaflets in the mitral valve.
Figure 3:
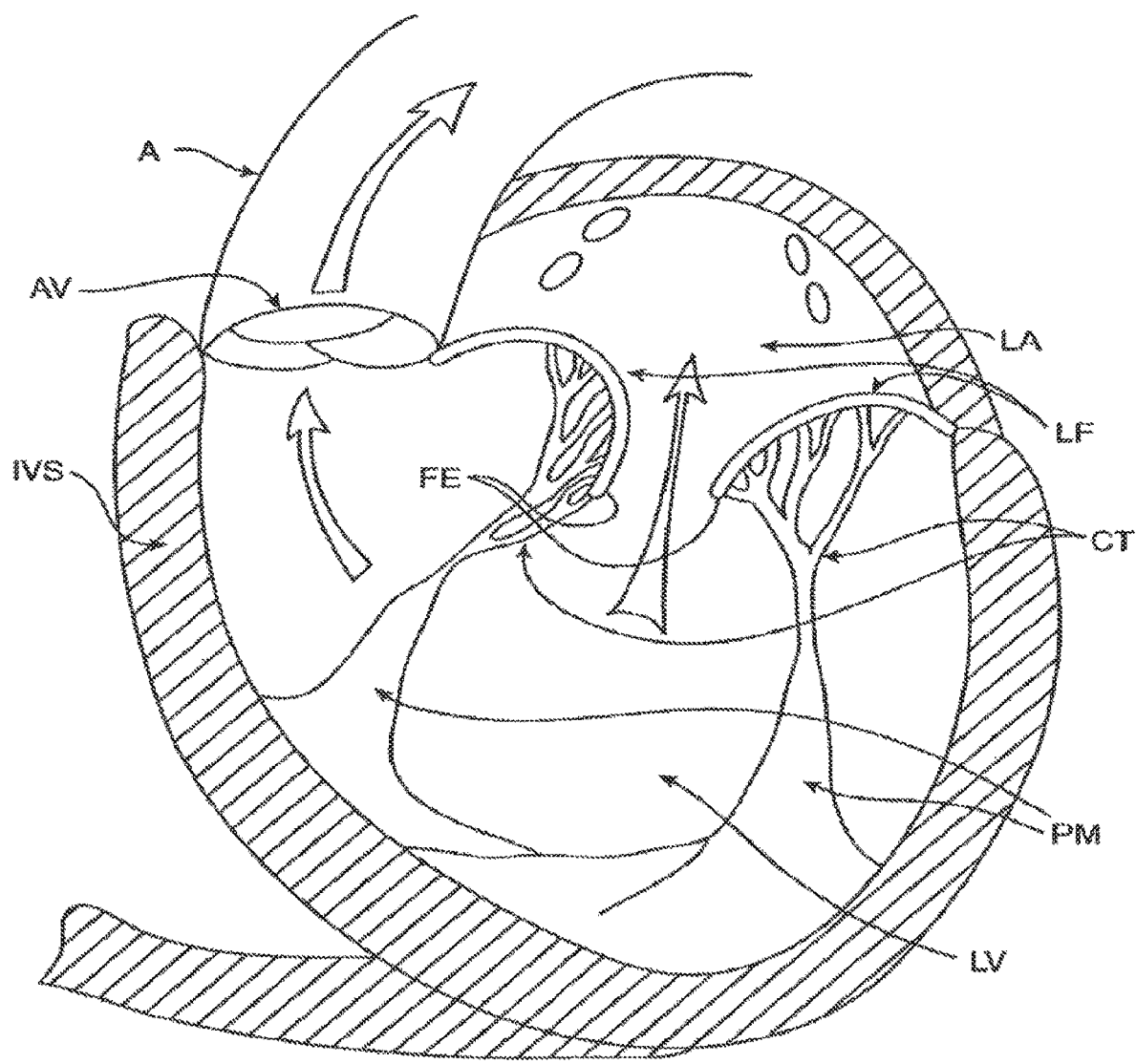
FIG. 3 is a schematic illustration of a heart in a patient suffering from cardiomyopathy where the heart is dilated and the leaflets do not meet.
Figure 4:
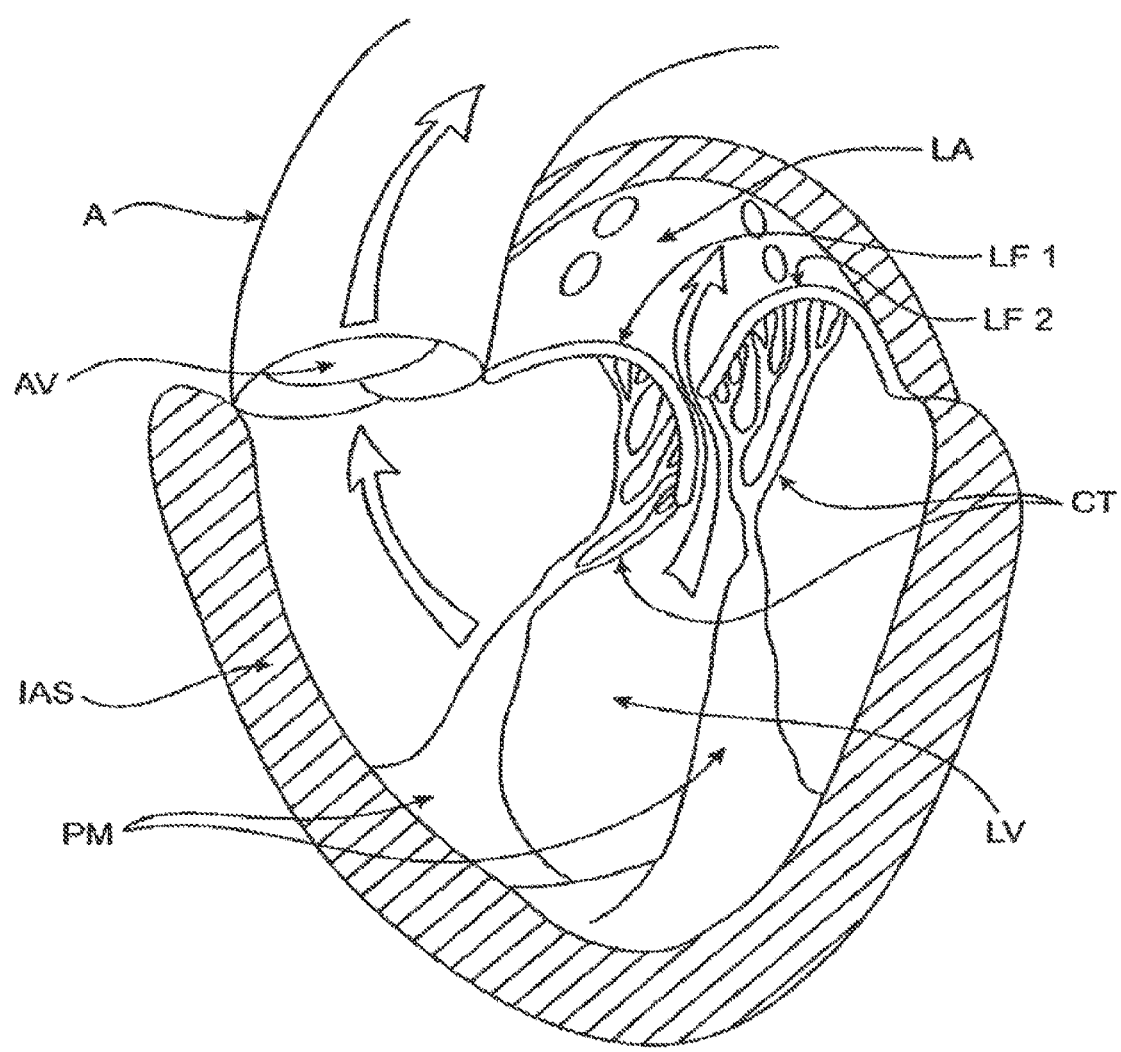
FIG. 4 illustrates mitral valve regurgitation in the left ventricle of a heart having impaired papillary muscles.

Referring now to FIGS. 2-4, a number of structural defects in the heart can cause mitral valve regurgitation. Ruptured chordae RCT, as shown in FIG. 2, can cause a valve leaflet LF2 to prolapse since inadequate tension is transmitted to the leaflet via the chordae. While the other leaflet LF1 maintains a normal profile, the two valve leaflets do not properly meet and leakage from the left ventricle LV into the left atrium LA will occur, as shown by the arrow.

Figure 3A:
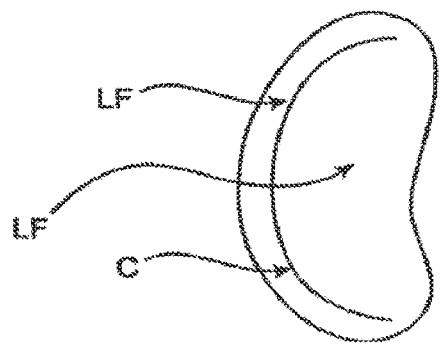
FIG. 3A shows normal closure of the valve leaflets.
Figure 3B:
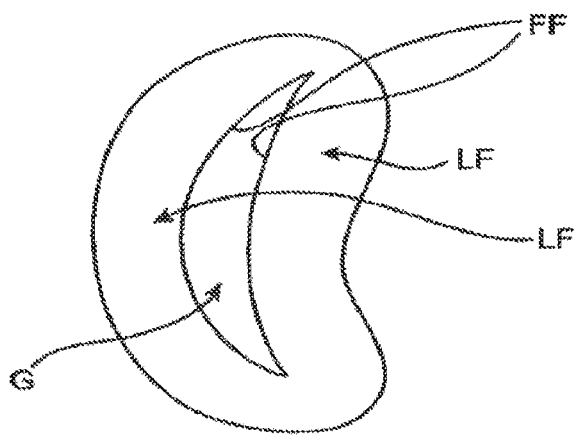
FIG. 3B shows abnormal closure of the valve leaflets.

Regurgitation also occurs in the patients suffering from cardiomyopathy where the heart is dilated and the increased size prevents the valve leaflets LF from meeting properly, as shown in FIG. 3. The enlargement of the heart causes the mitral annulus to become enlarged, making it impossible for the free edges FE to meet during systole. The free edges of the anterior and posterior leaflets normally meet along a line of coaptation C as shown in FIG. 3A, but a significant gap G can be left in patients suffering from cardiomyopathy, as shown in FIG. 3B.

Mitral valve regurgitation can also occur in patients who have suffered ischemic heart disease where the functioning of the papillary muscles PM is impaired, as illustrated in FIG. 4. As the left ventricle LV contracts during systole, the papillary muscles PM do not contract sufficiently to effect proper closure. The leaflets LF1 and LF2 then prolapse, as illustrated. Leakage again occurs from the left ventricle LV to the left atrium LA, as shown by the arrow.

Figure 5A:
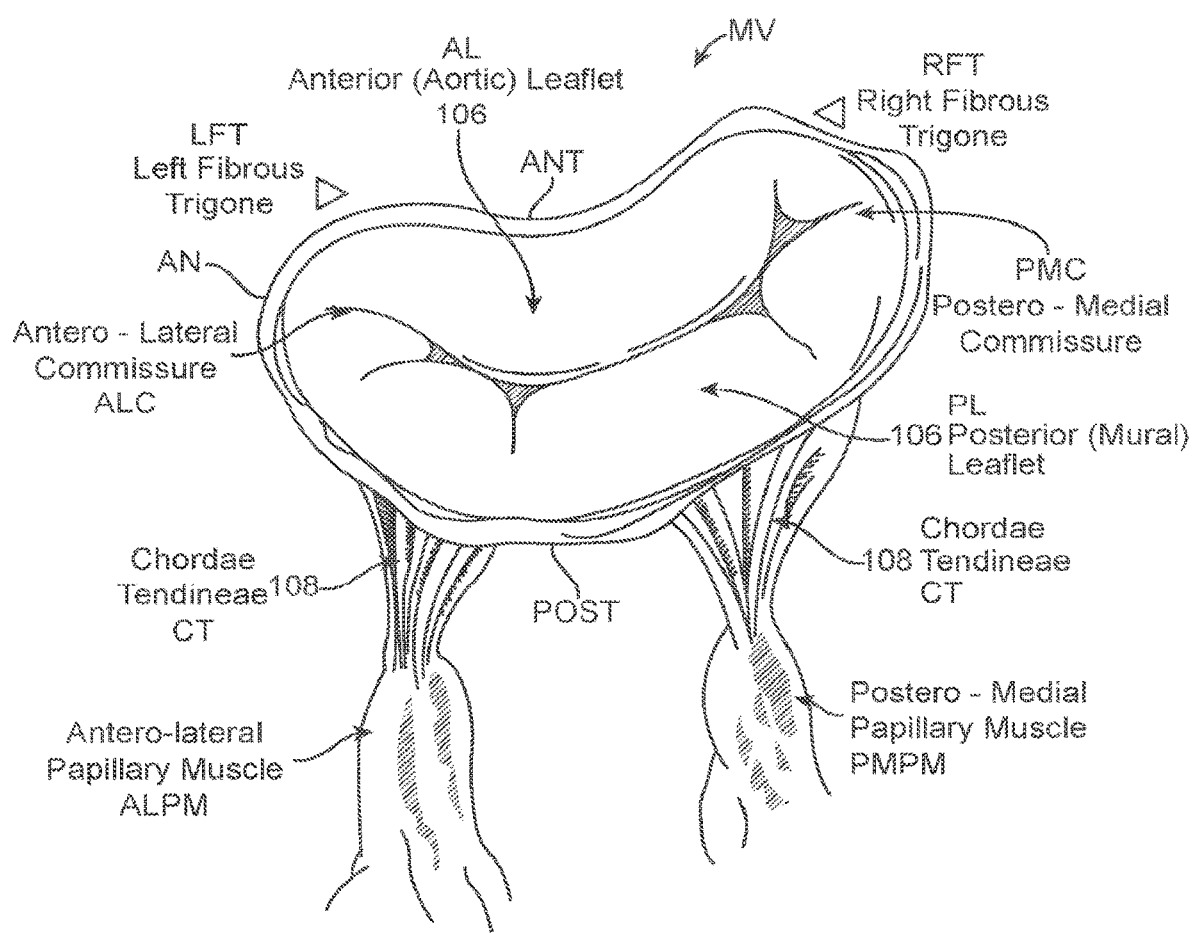
FIGS. 5A-5B illustrate anatomy of the mitral valve.
Figure 5B:
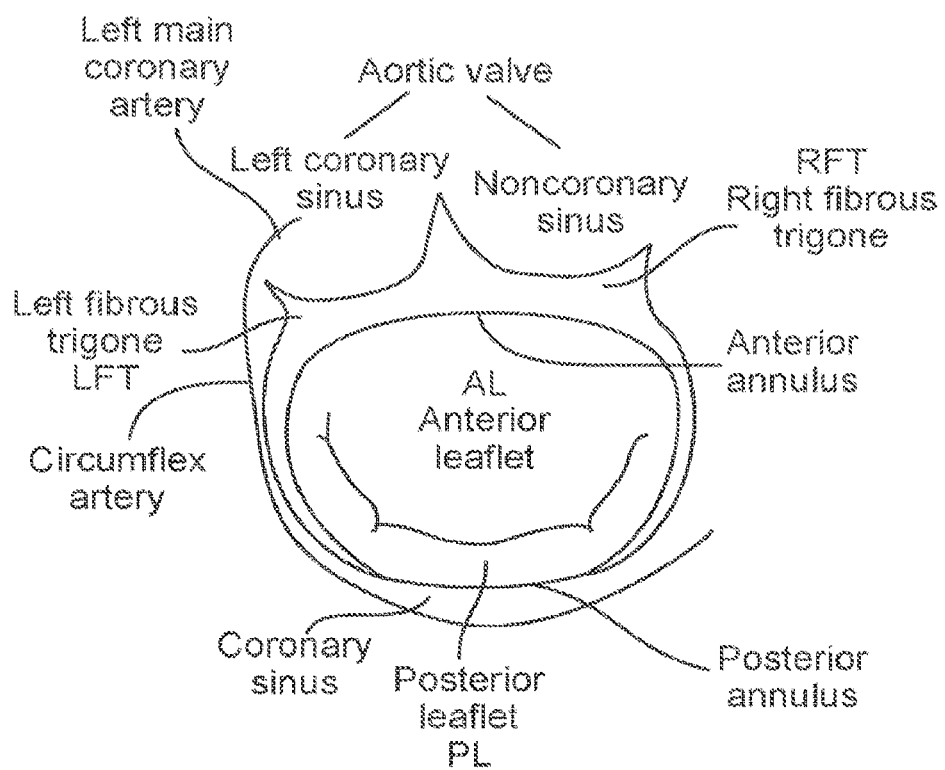

FIG. 5A more clearly illustrates the anatomy of a mitral valve MV which is a bicuspid valve having an anterior side ANT and a posterior side POST. The valve includes an anterior (aortic) leaflet AL and a posterior (mural) leaflet PL. Chordae tendineae CT couple the valve leaflets AL, PL with the antero-lateral papillary muscle ALPM and the posteromedial papillary muscle PMPM. The valve leaflets AL, PL join one another along a line referred to as the antero-lateral commissure ALC and the posterior-medial commissure PMC. The annulus AN circumscribes the valve leaflets, and two regions adjacent an anterior portion of the annulus, on opposite sides of the anterior leaflet are referred to as the left fibrous trigone LFT and also the right fibrous trigone RFT. These areas are indicted generally by the solid triangles. FIG. 5B more clearly illustrates the left and right fibrous trigones, LFT, RFT.

While various surgical techniques as well as implantable devices have been proposed and appear to be promising treatments for mitral regurgitation, surgical approaches can require a lengthy recovery period, and implantable devices have varying clinical results. Therefore, there still is a need for improved devices and methods for treating mitral regurgitation. While the embodiments disclosed herein are directed to an implantable prosthetic mitral valve for treating mitral regurgitation, one of skill in the art will appreciate that this is not intended to be limiting, and the device and methods disclosed herein may also be used to treat other cardiac valves such as the tricuspid valve, aortic valve, pulmonary valve, etc., as well as other valves in the body such as venous valves.

Prosthetic Valve. Prosthetic valves have been surgically implanted in the heart as a treatment for mitral regurgitation. Some of these valves have been valves harvested from animals such as porcine valves, and others have been prosthetic mechanical valves with or without a tissue covering. More recently, minimally invasive catheter technology has been used to deliver prosthetic valves to the heart. These valves typically include an anchor for securing the valve to the patient's heart, and a valve mechanism, either a mechanical valve, a valve with animal tissue, or combinations thereof. The prosthetic valve once implanted, takes over for the malfunctioning native valve, thereby reducing or eliminating valvar insufficiency. While some of these valves appear promising, there still is a need for improved valves. Positioning and anchoring the prosthetic valve in the native anatomy remains a challenge. The following specification discloses exemplary embodiments of a prosthetic valve, a delivery system for the prosthetic valve, and methods of delivering the valve that overcome some of the challenges associated with existing prosthetic valves.

Figure 6:
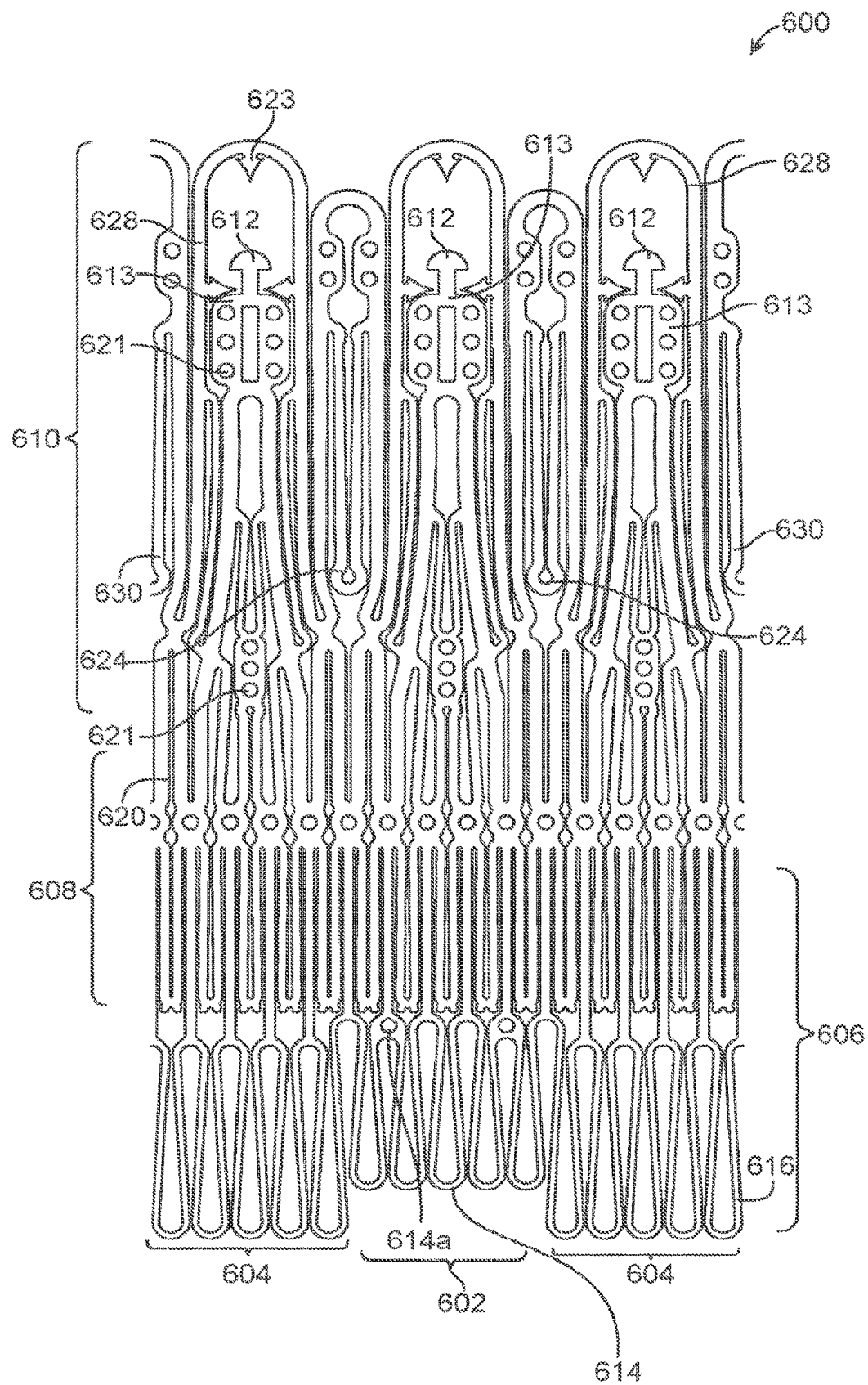
FIG. 6 illustrates an exemplary embodiment of an uncovered frame in a prosthetic cardiac valve, with the frame flattened out and unrolled.

FIG. 6 illustrates an exemplary embodiment of a prosthetic cardiac valve in the collapsed configuration. Coverings from the frame (e.g. fabric or tissue) has been removed to permit observation of the underlying frame 600. The frame has been unrolled and flattened out. The prosthetic valve frame 600 has an atrial region 606, an annular region 608, and a ventricular region 610. The frame 600 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using superelastic nitinol or other self-expanding materials. Shape memory alloys that spring open above a transition temperature may also be used, and expandable members may also be used to expand the frame when plastic deformation (e.g. balloon expansion) is required to open the frame.

Atrial region 606 has a skirt 616 which includes a plurality of interconnected struts that form a series of peaks and valleys. In this region, the struts are skewed relative to one another and thus the resulting cell pattern has an enlarged end and the opposite end tapers to a smaller end. In preferred embodiments, the anterior portion of the atrial skirt does not have a flanged region like the posterior portion, thus the anterior portion 602 of the atrial region may have shorter struts than the posterior region 604. Thus the peaks and valleys in the anterior portion are axially offset from those in the remaining posterior portion of the atrial region. This may be advantageous as it prevents the struts in the anterior portion of the atrial skirt from protruding upwards potentially impinging against the left atrium and causing perforations. Additionally, the shortened struts and offset peaks and valleys form an alignment element 614 that can assist the physician with visualization of delivery of the prosthetic valve to the mitral valve and also with alignment of the prosthetic valve prior to expansion of the prosthetic valve. Optional radiopaque markers 614a are disposed on either side of the offset peaks and valleys and further help with visualization during implantation of the valve. The atrial region preferably self-expands to either a cylindrical shape, or it may have a D-shaped cross-section where the anterior portion 602 is substantially flat, and the posterior portion 604 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 608 with connecting struts which are preferably linear and substantially parallel to the longitudinal axis of the frame.

The annular region 608 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and expanded against the mitral valve annulus. Connector struts join the annular region with the ventricular region 610.

The ventricular region 610 also includes a plurality of interconnected struts that form peaks and valleys. Additionally, the struts in the ventricular region form the leaflet commissures 613 which are covered with fabric, pericardial tissue, or other materials to form the prosthetic valve leaflets. Holes in the commissures allow suture to be attached thereto. Struts in the ventricular region also form a ventricular skirt 628 which expands outward to engage the anterior and posterior mitral valve leaflets, and struts in the ventricular region also form the anterior tabs 624 and the posterior tab 630. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below.

By controlling strut length or axial position of the anterior or posterior tabs along the frame, the sequence of the deployment of the tabs may be controlled. Thus in this exemplary embodiment, because the length of the struts in the anterior tabs and posterior tabs 624, 630 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward. Further retraction of the constraining sheath then allows the remainder of the posterior tab to finish its radial expansion, and finally the ventricular skirt will radially expand outward. While strut lengths and axial position of the posterior tab and the ventricular skirt are similar, internal struts connect the ventricular skirt with the commissures, and this delays expansion of the ventricular skirt slightly, thus the posterior tab finishes expansion before the ventricular skirt. Using this sequence of deploying the prosthetic valve may allow the valve to more accurately be delivered and also more securely anchored into position. For example, either the anterior tab(s) or the posterior tab(s) may be more easily visualized than the other in at least some cases, and the more easily visualized tab may be configured to deploy first as a guide to orient the frame during implantation. In at least some cases, the Inventors have found that the posterior tab is easier to visualize using ultrasound and/or fluoroscopy. The sequence of tab deployment may be customized to the individual patient and their anatomy in some cases and the customization may be based on pre-screen imaging data for the individual patient. The tabs that are projected to be more easily visualized, such as by using ultrasound and/or fluoroscopy, may be configured to deploy first. The initially deployed tabs can allow for intermediate movement of the imaging source, e.g., the C-arm controlling the ultrasound or X-ray device for fluoroscopy, so as to provide verification of the initial tab placements. If needed, the prosthetic valve may be repositioned and/or reoriented with the initial tab(s) deployed (and the remaining tab(s) yet to be deployed) based on the imaging or visualization. To further improve the visibility of the tabs, the length and/or curvature of one or more of the tabs may be customized for the individual patient and their anatomy. The length and/or curvature of the one or more tabs may be customized to provide an optimum fit for the individual patient's anatomy, such as the deployment area behind the valve leaflet(s) and/or the chordae tendinae.

Suture holes 621 are disposed along the struts of the annular region as well as the ventricular region to allow attachment of a cover such as pericardium or a polymer such as Dacron or ePTFE. The suture holes may also be disposed along any other part of the frame. Barbs 623 are disposed along the ventricular skirt 628 to help anchor the prosthetic valve to adjacent tissue. Commissure tabs or tabs 612 are disposed on the tips of the commissures 613 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc. may be adjusted in order to provide the prosthesis with the desired mechanical properties such as stiffness, radial crush strength, commissure deflection, etc. Therefore, the illustrated geometry is not intended to be limiting.

The frame may be formed by electrical discharge machining (EDM), laser cutting, photochemical etching, or other techniques known in the art. Hypodermic tubing or flat sheets may be used to form the frame. Once the frame has been cut and formed into a cylinder (if required), it may be radially expanded into a desired geometry and heat treated using known processes to set the shape. Thus, the prosthetic valve may be loaded onto a delivery catheter in a collapsed configuration and constrained in the collapsed configuration with a constraining sheath. Removal of the constraining sheath will allow the prosthesis to self-expand into its unbiased pre-set shape. In other embodiments, an expandable member such as a balloon may be used to radially expand the prosthesis into its preferred expanded configuration.

Figure 7:
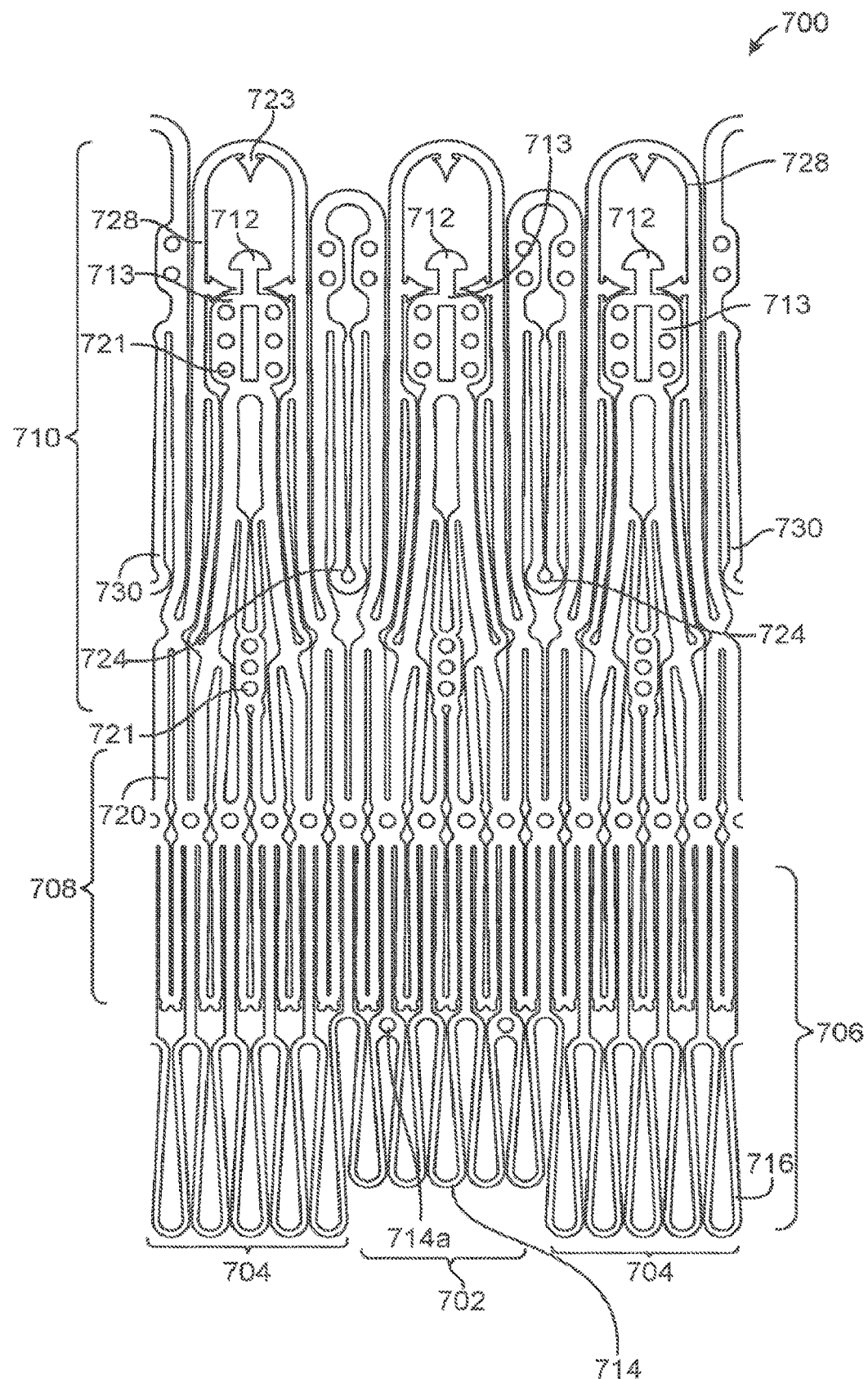
FIG. 7 illustrates another exemplary embodiment of an uncovered frame in a prosthetic cardiac valve, with the frame flattened out and unrolled.

FIG. 7 illustrates another exemplary embodiment of a prosthetic cardiac valve in the collapsed configuration, and similar to the previous embodiment with the major difference being the strut lengths in the anterior tabs, posterior tab, and ventricular skirt. Varying the strut lengths allow the sequence of expansion of the anterior and posterior tabs and ventricular skirt to be controlled. Coverings from the frame (e.g. fabric or tissue) has been removed to permit observation of the underlying frame 700. The frame has been unrolled and flattened out. The prosthetic valve frame 700 has an atrial region 706, an annular region 708, and a ventricular region 710. The frame 700 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using superelastic nitinol or other self-expanding materials. Shape memory alloys that spring open above a transition temperature may also be used, and expandable members may also be used to expand the frame when plastic deformation (e.g. balloon expansion) is required to open the frame.

Atrial region 706 has a skirt 716 which includes a plurality of interconnected struts that form a series of peaks and valleys. In this region, the struts are skewed relative to one another and thus the resulting cell pattern has an enlarged end and the opposite end tapers to a smaller end. An anterior portion 702 of the atrial region has shorter struts than the posterior region 704. Thus the peaks and valleys in the anterior portion are axially offset from those in the remaining posterior portion of the atrial region. This allows creation of an alignment element 714 to help the physician deliver the prosthetic valve to the mitral valve and align the prosthetic valve prior to expansion of the prosthetic valve. Other aspects of the atrial region 706 are similar to those of the atrial region 606 in FIG. 6. Optional radiopaque markers 714*a* are disposed on either side of the offset peaks and valleys and help with visualization during implantation of the valve. The atrial region preferably self-expands to either a cylindrical shape, or it may have a D-shaped cross-section where the anterior portion 702 is substantially flat, and the posterior portion 704 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 708 with connecting struts which are preferably linear and substantially parallel to the longitudinal axis of the frame.

The annular region 708 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and against the mitral valve annulus. Connector struts join the annular region with the ventricular region 710.

The ventricular region 710 also includes a plurality of interconnected struts that form peaks and valleys. Additionally, the struts in the ventricular region form the leaflet commissures 713 which are covered with fabric, pericardial tissue, or other materials to form the prosthetic valve leaflets. Holes in the commissures allow suture to be attached thereto. Struts in the ventricular region also form a ventricular skirt 728 which expands outward to engage the anterior and posterior mitral valve leaflets, and struts in the ventricular region also form the anterior tabs 724 and the posterior tab 730. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similar captures the posterior mitral valve leaflet between an inner surface of the posterior tab and an outer surface of the ventricular skirt, along with any adjacent chordae tendineae. This will be described in more detail below.

By controlling strut length or axial position of the anterior or posterior tabs along the frame, deployment of the tabs may be controlled. Thus in this exemplary embodiment, because the length of the struts in the anterior tabs and posterior tabs 724, 730 as well as their relative position along the frame are the same as one another, when a constraining sheath is retracted away from the tabs, the anterior and posterior tabs will partially spring outward together. As the constraining sheath is further retracted, the remainder of the anterior tabs will self-expand radially outward because they are the shortest relative to the struts in the ventricular skirt and the posterior tab. Further retraction of the constraining sheath then allows the ventricular skirt to radially expand, and finally further retraction of the sheath allows the remainder of the posterior tab to finish it's radial expansion. Using this sequence of deploying the prosthetic valve may allow the valve to more accurately be delivered and also more securely anchored into position.

Suture holes 721 are disposed along the struts of the annular region as well as the ventricular region to allow attachment of a cover such as pericardium or a polymer such as Dacron or ePTFE. The suture holes may also be disposed along any other part of the frame. Barbs 723 are disposed along the ventricular skirt 728 to help anchor the prosthetic valve to adjacent tissue. Commissure tabs or tabs 712 are disposed on the tips of the commissures 713 and may be used to releasably couple the commissures with a delivery system as will be described below. This allows the frame to expand first, and then the commissures may be released from the delivery system afterwards. One of skill in the art will appreciate that a number of strut geometries may be used, and additionally that strut dimensions such as length, width, thickness, etc., may be adjusted in order to provide the prosthesis with the desired mechanical properties such as stiffness, radial crush strength, commissure deflection, etc. Therefore, the illustrated geometry is not intended to be limiting. The frame may be formed similarly as described above with respect to FIG. 6.

Figure 8:
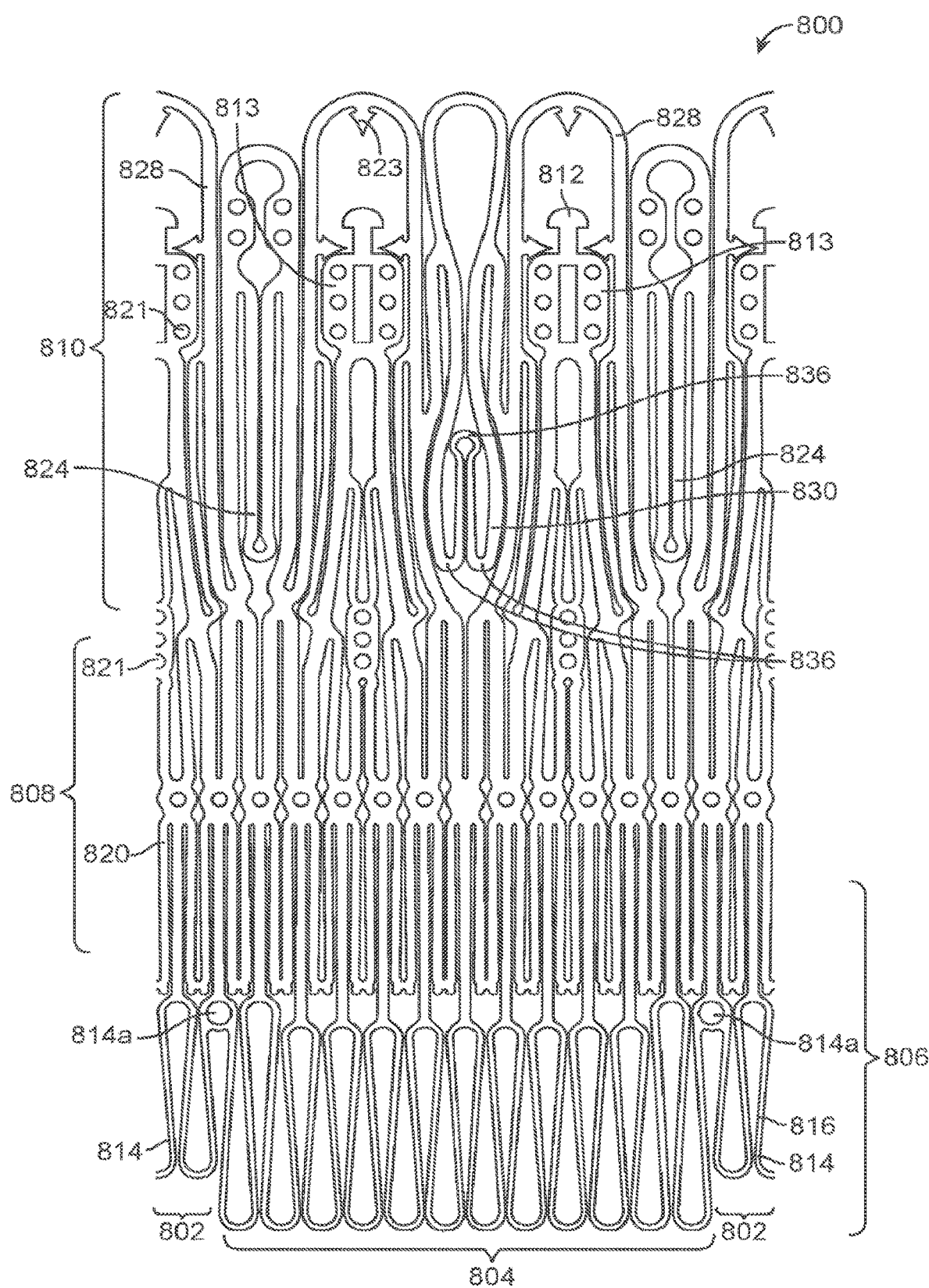
FIG. 8 illustrates still another exemplary embodiment of an uncovered frame in a prosthetic cardiac valve, with the frame flattened out and unrolled.

FIG. 8 illustrates another exemplary embodiment of a prosthetic cardiac valve in the collapsed configuration, and is similar to the previous embodiments, with the major difference being that the posterior tab is designed to expand to form an elongate horizontal section which allows engagement and anchoring of the posterior tab with the sub-annular region between the posterior leaflet and the ventricular wall. Thus, the elongate horizontal section contacts a larger region of the sub-annular region as compared with a posterior tab that only has a tapered tip formed from a single hinge between struts. This provides enhanced anchoring of the prosthetic valve. In this exemplary embodiment, the anterior tabs will completely self-expand first, followed by the posterior tab and then the ventricular skirt. However, in some situations external factors such as the delivery system, anatomy, etc. may alter the sequence of expansion, and therefore this is not intended to be limiting. Coverings from the frame (e.g. fabric or tissue) have been removed to permit observation of the underlying frame 800. The frame has been unrolled and flattened out. The prosthetic valve frame 800 has an atrial region 806, an annular region 808, and a ventricular region 810. The frame 800 is formed from a plurality of interconnected struts that form a series of peaks and valleys which can expand and contract relative to one another thereby permitting the frame to be loaded onto a delivery catheter in a collapsed configuration, and then radially expanded at a target treatment site for implantation. Preferred embodiments are self-expanding and may be fabricated using superelastic nitinol or other self-expanding materials. Shape memory alloys that spring open above a transition temperature may also be used, and expandable members may also be used to expand the frame when plastic deformation (e.g. balloon expansion) is required to open the frame.

Atrial region 806 has a skirt 816 which includes a plurality of interconnected struts that form a series of peaks and valleys. In this region, the struts are skewed relative to one another and thus the resulting cell pattern has an enlarged end and the opposite end tapers to a smaller end. An anterior portion 802 of the atrial region has shorter struts than the posterior region 804. Thus the peaks and valleys in the anterior portion are axially offset from those in the remaining posterior portion of the atrial region. This allows creation of an alignment element 814 to help the physician deliver the prosthetic valve to the mitral valve and align the prosthetic valve prior to expansion of the prosthetic valve. Other aspects of the atrial region 806 are similar to those of the atrial region 606 in FIG. 6. Optional radiopaque markers 814a are disposed on either side of the offset peaks and valleys and help with visualization during implantation of the valve. The atrial region preferably self-expands to either a cylindrical shape, or it may have a D-shaped cross-section where the anterior portion 802 is substantially flat, and the posterior portion 804 is cylindrically shaped. This allows the atrial skirt to conform to the anatomy of the native mitral valve, thereby preventing obstruction of the left ventricular outflow tract. Additionally, the atrial skirt may also be formed so that upon expansion, the skirt flares outward and forms a flange that can rest against a superior surface of the mitral valve. The flanged region is preferably along the posterior portion of the atrial skirt, and the anterior portion of the atrial skirt remains flangeless. Or, the flange may extend entirely around the atrial skirt. The atrial region is connected to the adjacent annular region 808 with connecting struts which are preferably linear and substantially parallel to the longitudinal axis of the frame.

The annular region 808 is also comprised of a plurality of axially oriented and interconnected struts that form peaks and valleys that allow radial expansion. The struts are preferably parallel with one another and parallel with the longitudinal axis of the frame. The annular region may also be self-expanding and expand into a cylindrical shape, or more preferably the annular region may expand to have a D-shaped cross-section as described above with respect to the atrial region. Thus, the annular region may similarly have a flat anterior portion, and a cylindrically shaped posterior portion. Upon delivery, the annular region is aligned with and against the mitral valve annulus. Connector struts join the annular region with the ventricular region 810.

The ventricular region 810 also includes a plurality of interconnected struts that form peaks and valleys. Additionally, the struts in the ventricular region form the leaflet commissures 813 which are covered with fabric, pericardial tissue, or other materials to form the prosthetic valve leaflets. Holes in the commissures allow suture to be attached thereto. Struts in the ventricular region also form a ventricular skirt 828 which expands outward to engage the anterior and posterior mitral valve leaflets, and struts in the ventricular region also form the anterior tabs 824 and the posterior tab 830. The anterior tabs are designed to capture the anterior mitral valve leaflet between an inner surface of the anterior tab and outer surface of the ventricular skirt. Any adjacent chordae tendineae may also be captured therebetween. Also, the tip of the anterior tab engages the fibrous trigone on an anterior portion of the mitral valve, one on the left and one on the right side. The posterior tab similarly captures the posterior mitral valve leaflet between an inner surface of the posterior tab and an outer surface of the ventricular skirt, along with any adjacent chordae tendineae. This will be described in more detail below. The posterior tab is similar to the posterior tabs described above in FIGS. 6-7, except that in this embodiment, the posterior tab comprises four interconnected struts as opposed to two interconnected struts. Thus, in this embodiment the plurality of interconnected struts form three hinged regions 836 along the tab. Upon expansion of the posterior tab, the hinged regions will also expand, thereby forming an elongate horizontal section which allows engagement and anchoring of the posterior tab with the sub-annular region between the posterior leaflet and the ventricular wall. This may help position and anchor the prosthetic valve better than posterior tabs which only have a smaller footprint or a single tapered tip for engagement with the posterior portion of the mitral valve. The posterior tab in this embodiment, may be substituted with any of the other posterior tabs described in this specification.

By controlling strut length or axial position of the anterior or posterior tabs along the frame, deployment of the tabs may be controlled. Thus in this exemplary embodiment, because the length of the struts in the anterior tabs and posterior tabs 824, 830 as well as their relative position along the frame are the same as one another, when a constraining sheath is retracted away from the tabs, the anterior and posterior tabs will partially spring outward together. As the constrainimg sheath is further retracted, the remainder of the anterior tabs will self-expand radially outward because they are the shortest relative to the struts in the ventricular skirt and the posterior tab. Further retraction of the constraining sheath then allows the remainder of the posterior tab to finish self-expanding, followed by self-expansion of the ventricular skirt. Using this sequence of deploying the prosthetic valve may allow the valve to more accurately be delivered and also more securely anchored into position.

Suture holes 821 are disposed along the struts of the annular region as well as the ventricular region to allow attachment of a cover such as pericardium or a polymer such as Dacron or ePTFE. The suture holes may also be disposed along any other part of the frame. Barbs 823 are disposed along the ventricular skirt 828 to help anchor the prosthetic valve to adjacent tissue. Commissure tabs or tabs 812 are disposed on the tips of the commissures 813 and may be used to releasably couple the commissures with a delivery system as will be described below. This allows the frame to expand first, and then the commissures may be released from the delivery system afterwards. One of skill in the art will appreciate that a number of strut geometries may be used, and additionally strut dimensions such as length, width, thickness, etc. may be adjusted in order to provide the prosthesis with the desired mechanical properties such as stiffness, radial crush strength, commissure deflection, etc. Therefore, the illustrated geometry is not intended to be limiting. The frame may be formed similarly as described above.

Figure 9A:
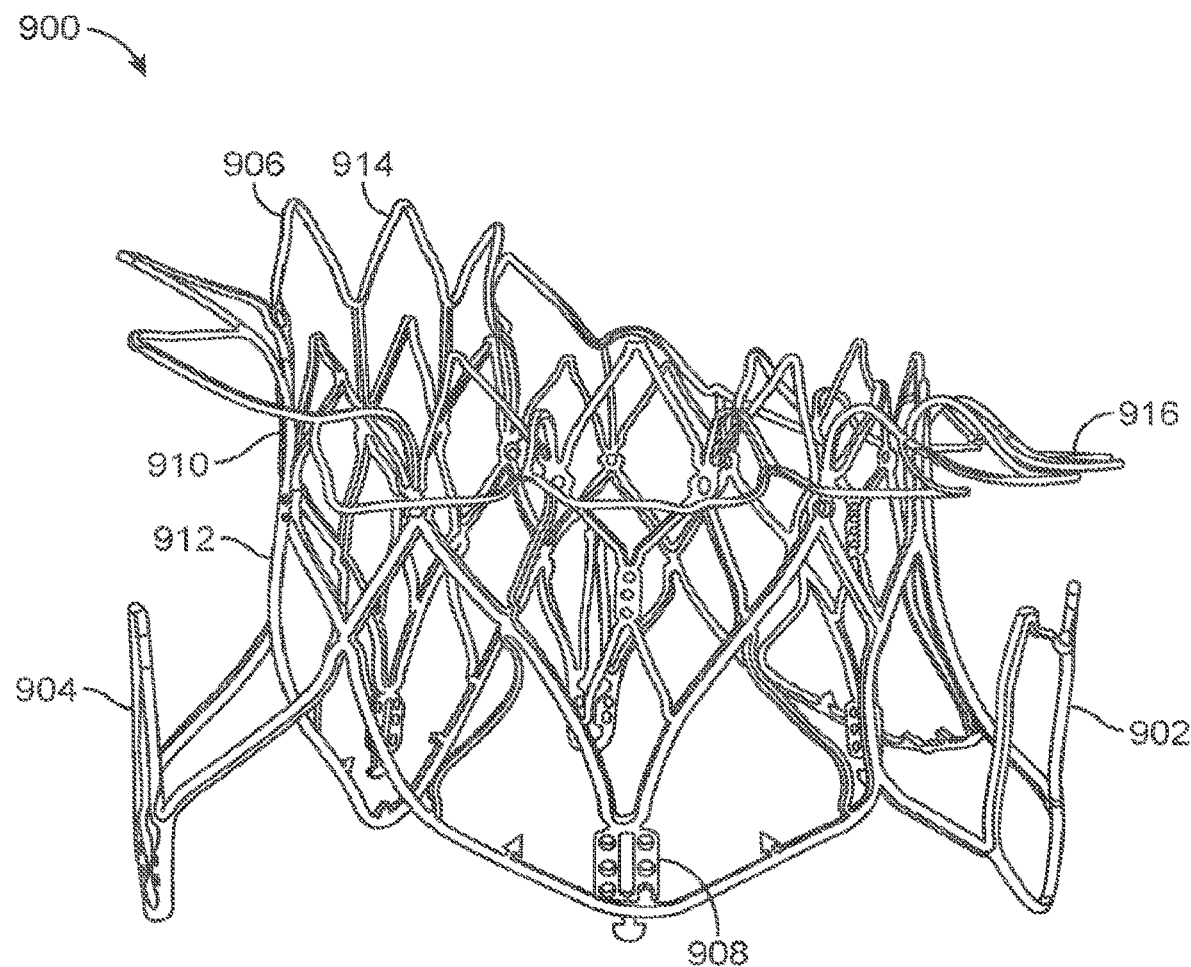
FIG. 9A illustrates a perspective view of an uncovered frame in a prosthetic cardiac valve after it has expanded.
Figure 9B:
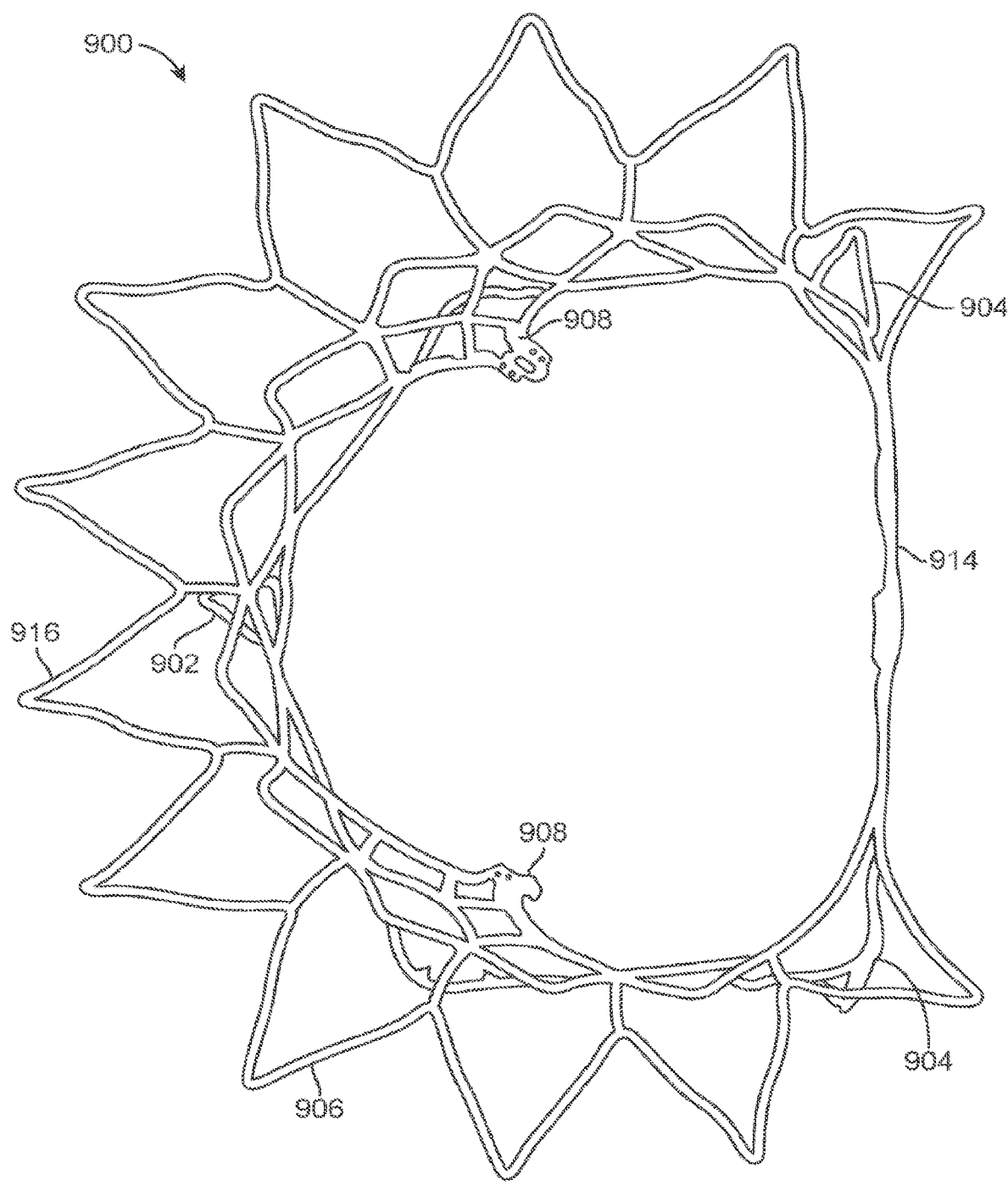
FIG. 9B illustrates a top view of the embodiment in FIG. 9A.

FIG. 9A illustrates the frame 900 of a prosthetic cardiac valve after it has expanded. Any of the frame embodiments described above may take this form as each of the above frames have similar geometry but they expand in different order. The frame includes the atrial skirt 906 with anterior portion 914 and posterior portion 916. A flanged region is formed around the posterior portion and the anterior portion remains flangeless. Additionally, the anterior portion is generally flat, while the posterior portion is cylindrically shaped, thereby forming a D-shaped cross-section which accommodates the mitral valve anatomy. FIG. 9B is a top view of the embodiment in FIG. 9A and more clearly illustrates the D-shaped cross-section.

The frame also includes the annular region 910 and ventricular skirt 912. Anterior tabs 904 (only one visible in this view) is fully expanded such that a space exists between the inner surface of the anterior tab and an outer surface of the ventricular skirt. This allows the anterior leaflet and adjacent chordae to be captured therebetween. Similarly, the posterior tab 902 is also fully deployed, with a similar space between the inner surface of the posterior tab 902 and an outer surface of the ventricular skirt. This allows the posterior leaflet and adjacent chordae tendineae to be captured therebetween. The commissure posts 908 are also visible and are disposed in the inner channel formed by the frame. The commissure posts are used to form the prosthetic mitral valve leaflets. The overall shape of the expanded frame is D-shaped, with the anterior portion flat and the posterior portion cylindrically shaped.

Figure 10:
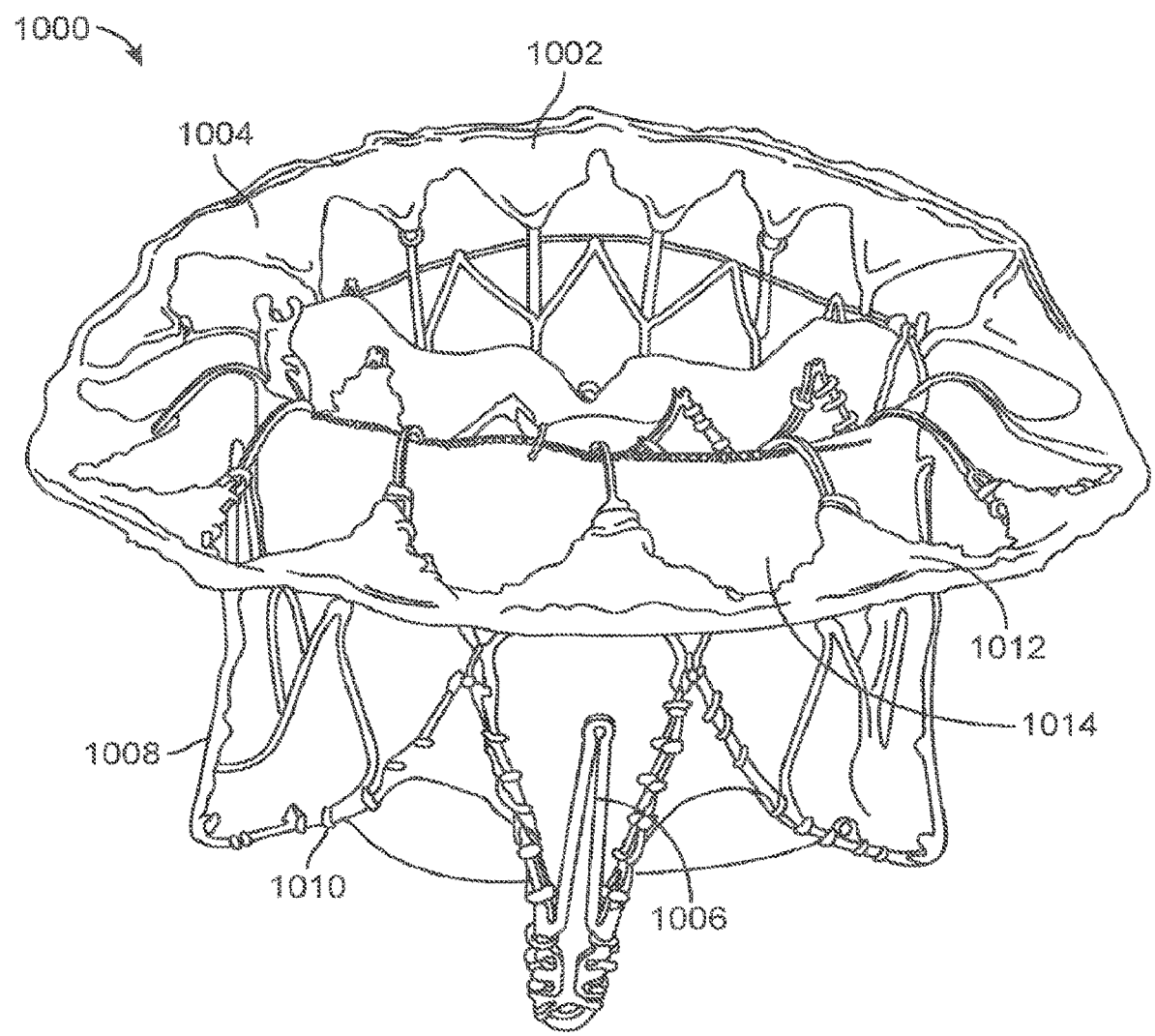
FIG. 10 illustrates the frame of FIG. 9A with the covering thereby forming a prosthetic cardiac valve.

FIG. 10 illustrates the expanded frame covered with a cover 1002 such as pericardial tissue or a polymer such as PTFE or a fabric like Dacron attached to the frame, thereby forming the prosthetic cardiac valve 1000. The atrial skirt may be entirely covered by a material, or in preferred embodiments, the covering is only disposed between adjacent struts 1012 in adjacent cells in the flanged portion of the atrial skirt. The area 1014 between adjacent struts within the same cell remain uncovered. This allows blood flow to remain substantially uninterrupted while the prosthetic valve is being implanted. Suture 1010 may be used to attach the cover to the frame. In this view, only the posterior tab 1006 is visible on the posterior portion of the prosthetic valve along with ventricular skirt 1008 and atrial skirt 1004.

Delivery System. FIGS. 11A-11D illustrate an exemplary embodiment of a delivery system that may be used to deliver any of the prosthetic cardiac valves disclosed in this specification. While the delivery system is designed to preferably deliver the prosthetic cardiac valve transapically, one of skill in the art will appreciate that it may also be modified so that the prosthetic valve may be delivered via a catheter transluminally, such using a transseptal route. One of skill in the art will appreciate that using a transseptal route may require the relative motion of the various shafts to be modified in order to accommodate the position of the delivery system relative to the mitral valve.

Figure 11A:
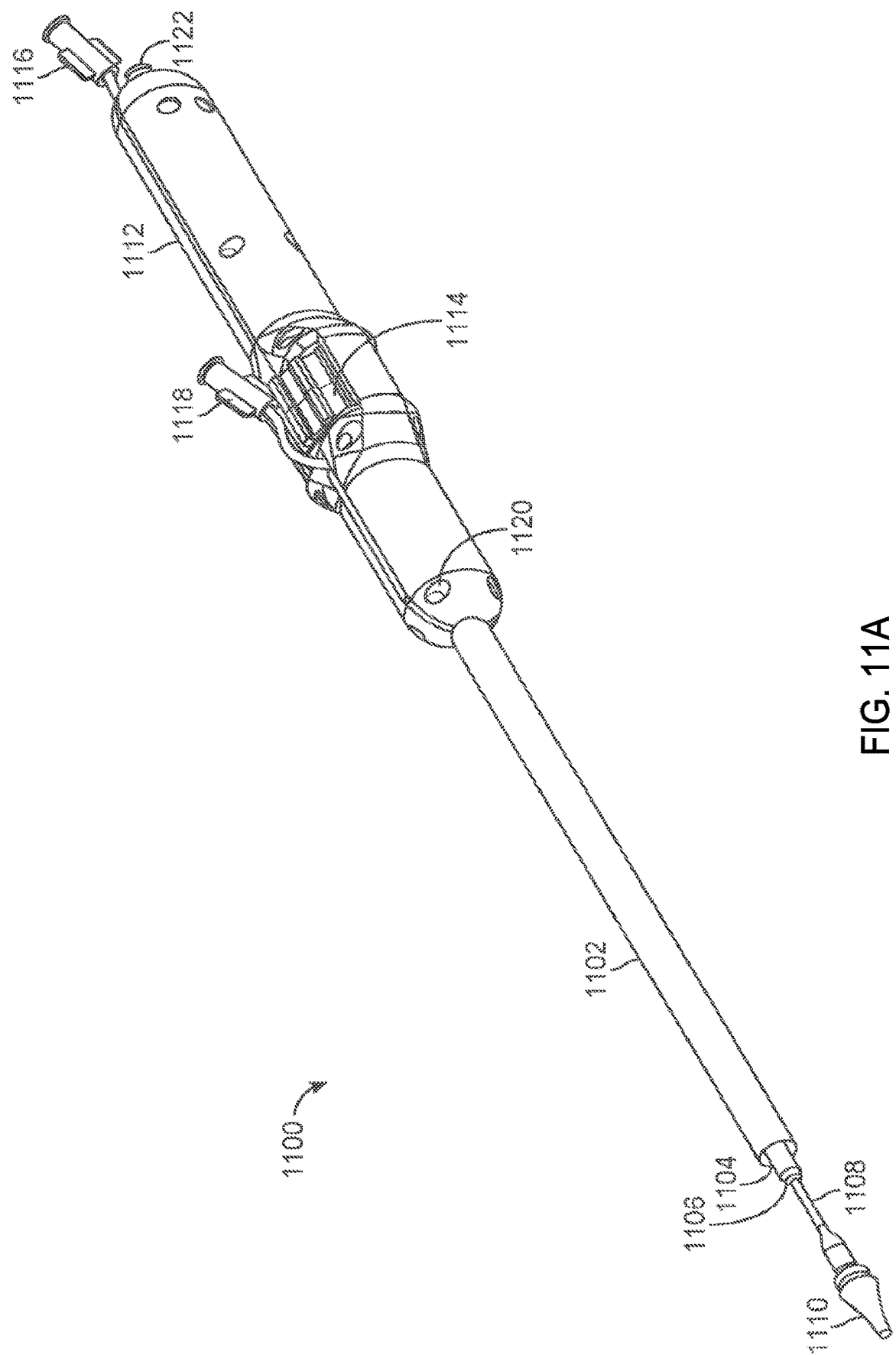
FIGS. 11A-11D illustrate an exemplary embodiment of a delivery system used to transapically deliver a prosthetic cardiac valve.
Figure 11B:
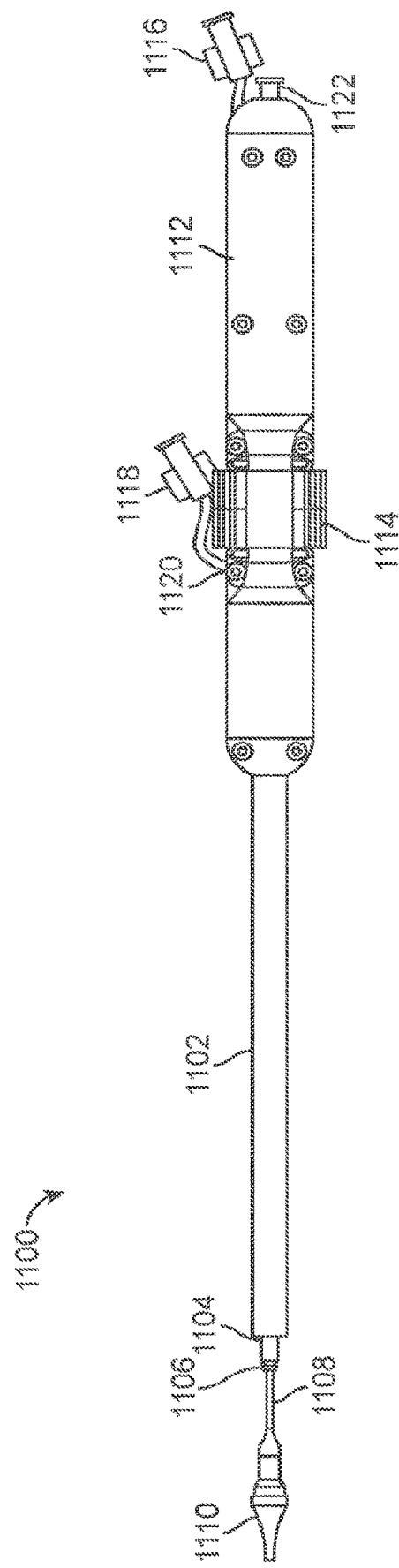

FIG. 11A illustrates a perspective view of delivery system 1100. The delivery system 1100 includes a handle 1112 near a proximal end of the delivery system and a distal tissue penetrating tip 1110. Four elongate shafts are included in the delivery system and include an outer sheath catheter shaft 1102, a bell catheter shaft 1104 which is slidably disposed in the outer sheath catheter shaft 1102, a hub catheter shaft 1106 which remains stationary relative to the other shafts, but the bell catheter shaft slides relative to the hub shaft, and finally an inner guidewire catheter shaft 1108 which is also fixed relative to the other shafts and has a lumen sized to receive a guidewire which passes therethrough and exits the distal tissue penetrating tip. An actuator mechanism 1114 is used to control movement of the various shafts as will be explained in greater detail below, and flush lines 1116, 1118 with luer connectors are used to flush the annular regions between adjacent shafts. Flush line 1118 is used to flush the annular space between the outer sheath catheter shaft 1102 and the bell catheter shaft 1104. Flush line 1116 is used to flush the annular space between the bell catheter 1104 and the hub catheter 1106. The inner guidewire catheter shaft 1108 is stationary relative to the hub catheter 1106 therefore the annular space may be sealed with an o-ring or other material. Luer connector 1122 allows flushing of the guidewire lumen and a hemostatic valve such as a Tuohy-Borst may be coupled to the luer connector to allow a guidewire to be advanced through the guidewire catheter shaft while maintaining hemostasis. Screws 1120 keep the handle housing coupled together. FIG. 11B illustrates a side view of the delivery system 1100.

Figure 11C:
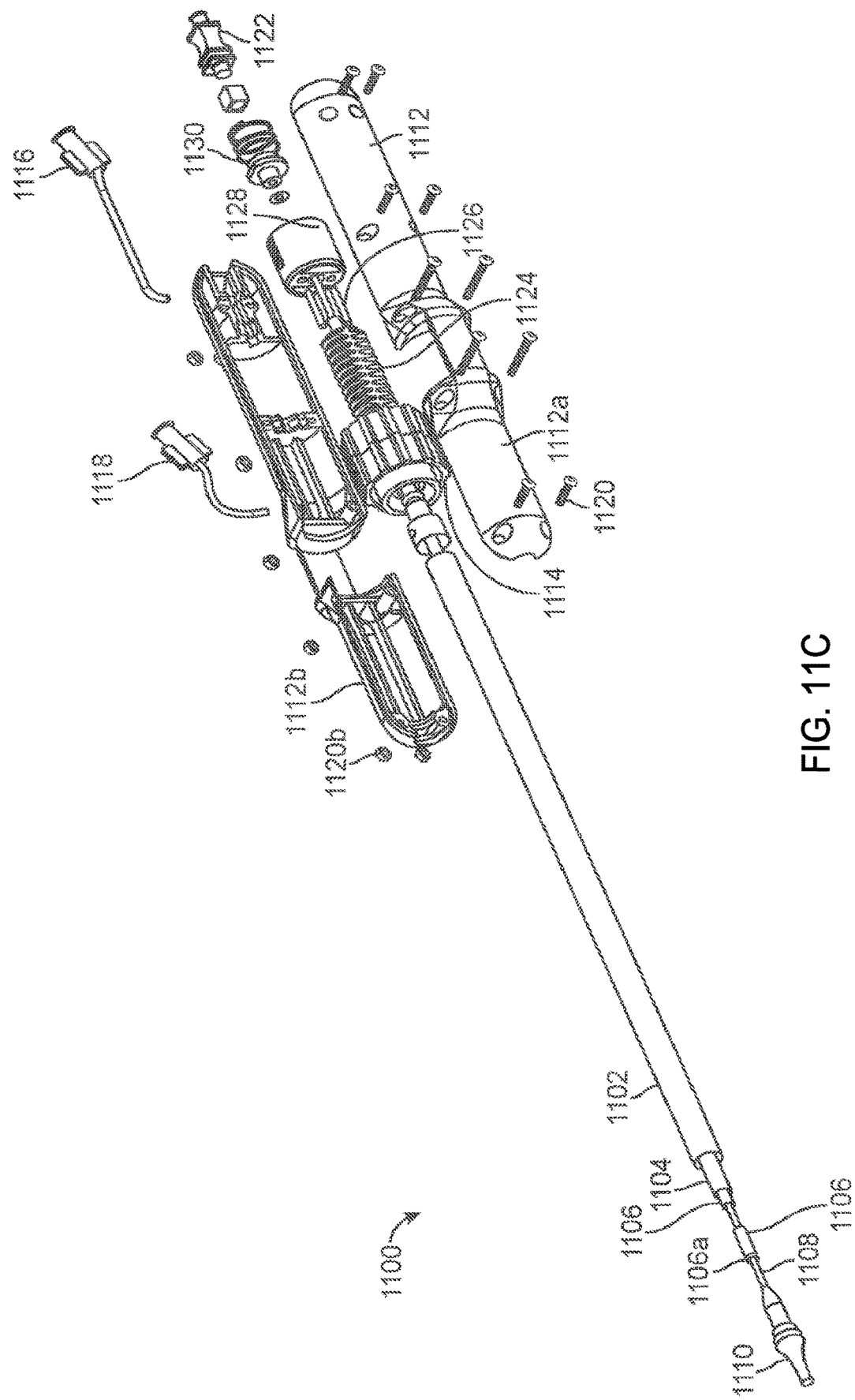

FIG. 11C is a partial exploded view of the delivery system 1100 and more clearly illustrates the components in the handle 1112 and how they interact. The handle 1112 includes a housing having two halves 1112a, 1112b which hold all the components. The handle is preferably held together with screws 1120 and nuts 1120b, although it may also be sealed using other techniques such as a press fit, snap fit, adhesive bonding, ultrasonic welding, etc. Rotation of actuator wheel 1114 is translated into linear motion of threaded insert 1124. The outer sheath catheter shaft 1102 is coupled to the threaded insert 1124, therefore rotation of actuator wheel 1114 in one direction will advance the sheath catheter shaft 1102, and rotation in the opposite direction will retract the sheath catheter shaft 1102. Further rotation of actuator wheel 1114 retracts threaded insert 1124 enough to bump into pins 1126 which are coupled to insert 1128, thereby also moving insert 1128. The bell catheter shaft 1106 is coupled to insert 1128, therefore further rotation of the actuator wheel 1114 will move the outer shaft 1102 and also move the bell catheter shaft 1106. Rotation of the actuator wheel in the opposite direction advances the sheath and threaded insert 1124 disengages from pins 1126. Spring 1130 returns insert 1128 to its unbiased position, thereby returning the bell catheter shaft to its unbiased position.

Any of the prosthetic cardiac valves disclosed herein may be carried by delivery system 1100. The atrial skirt, annular skirt, anterior tabs, posterior tab and ventricular skirt are loaded over the bell catheter shaft and disposed under the outer sheath catheter shaft 1102. The ventricular skirt is loaded proximally so that it is closest to the handle 1112 and the atrial skirt is loaded most distally so it is closest to the tip 1110. Therefore, retraction of outer sheath catheter shaft 1102 plays a significant part in controlling deployment of the prosthetic cardiac valve. The atrial skirt therefore expands first when the outer sheath catheter is retracted. The prosthetic valve commissures may be coupled with a hub 1106a on the distal portion of hub catheter 1106 and then the bell catheter shaft is disposed thereover, thereby releasably engaging the commissures with the delivery catheter. Once other portions of the prosthetic cardiac valve have expanded, the commissures may be released.

Figure 11D:
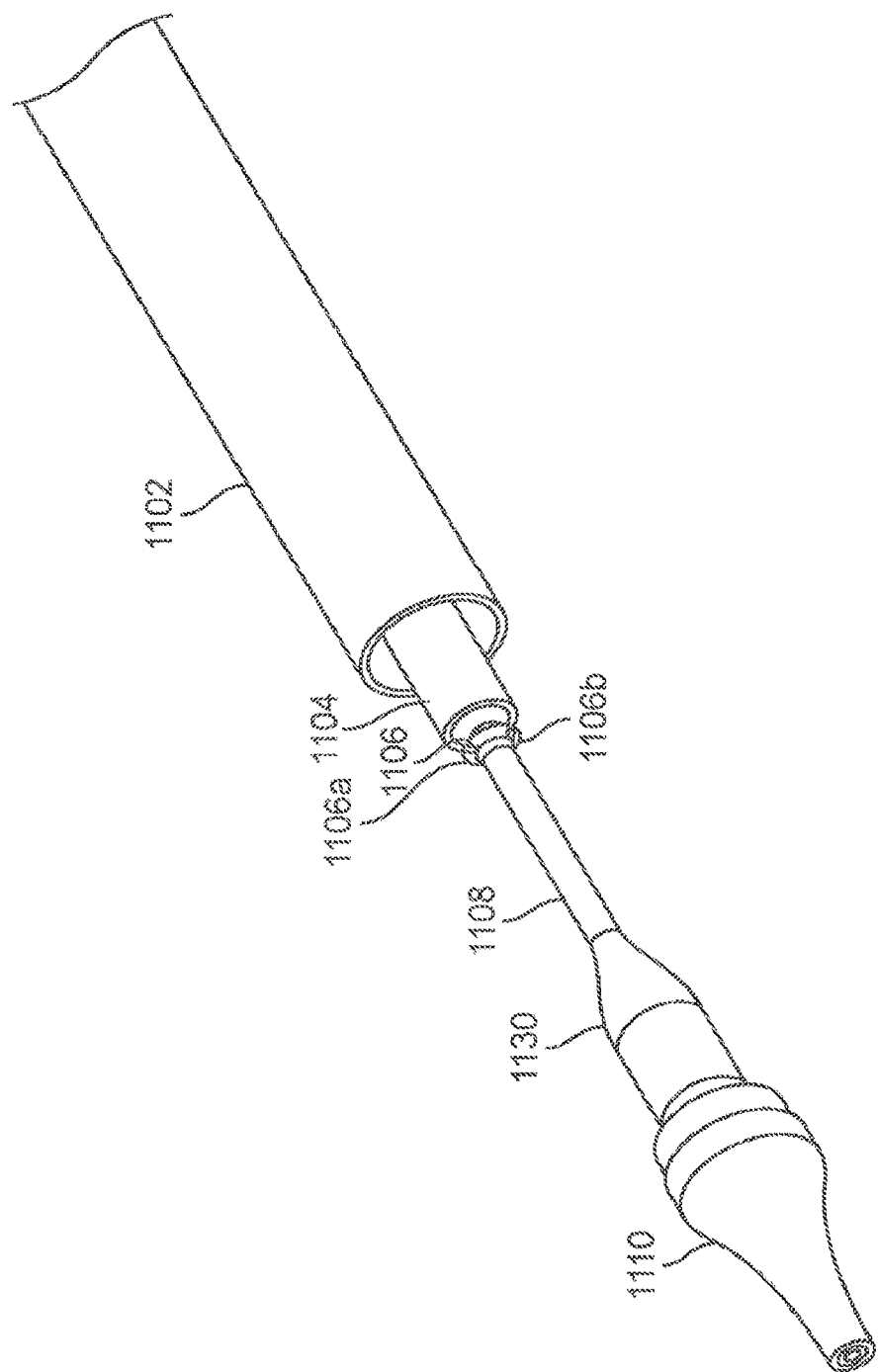

FIG. 11D highlights the distal portion of the delivery system 1100. Outer sheath catheter shaft 1102 advances and retracts relative to bell catheter shaft 1104 which is slidably disposed in the outer sheath catheter shaft 1102. Hub catheter shaft 1106 is shown slidably disposed in bell catheter shaft 1104 and with bell catheter shaft 1104 retracted so as to expose the hub 1106a having slots 1106b that hold the prosthetic valve commissures. Inner guidewire catheter shaft 1108 is the innermost shaft and has a tapered conical section 1130 which provides a smooth transition for the prosthetic valve and prevents unwanted bending or buckling of the prosthetic cardiac valve frame. Tissue penetrating tip 1110 is adapted to penetrate tissue, especially in a cardiac transapical procedure.

Delivery Method. A number of methods may be used to deliver a prosthetic cardiac valve to the heart. Exemplary methods of delivering a prosthetic mitral valve may include a transluminal delivery route which may also be a transseptal technique which crosses the septum between the right and left sides of the heart, or in more preferred embodiments, a transapical route may be used such as illustrated in FIGS. 12A-12L. The delivery device previously described above may be used to deliver any of the embodiments of prosthetic valves described herein, or other delivery devices and other prosthetic valves may also be used, such as those disclosed in U.S. patent application Ser. No. 13/096,572, previously incorporated herein by reference. However, in this preferred exemplary embodiment, the prosthetic cardiac valve of FIG. 6 is used so that the anterior tabs deploy first, followed by the posterior tab, and then the ventricular skirt.

Figure 12A:
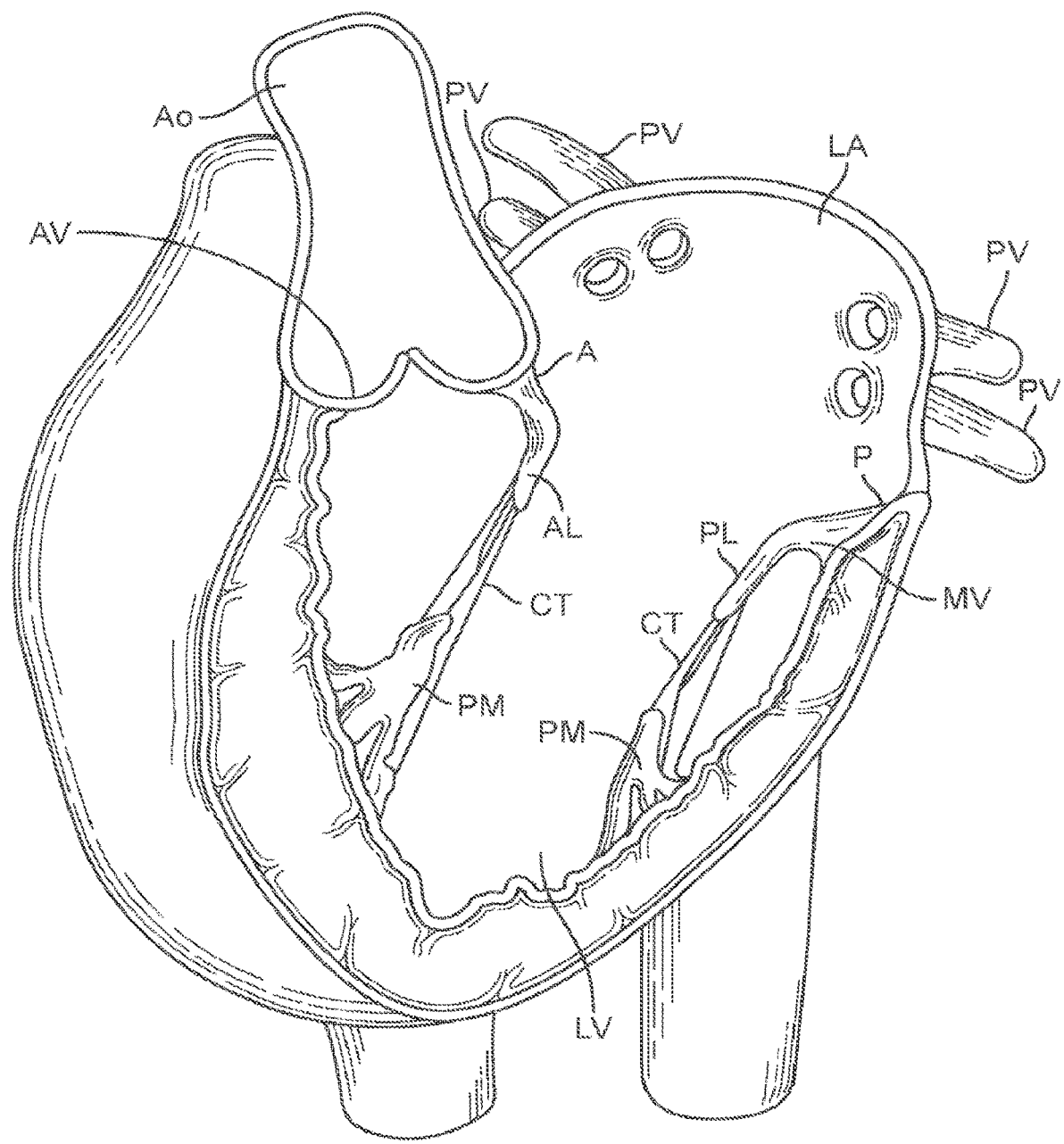
FIGS. 12A-12L illustrate an exemplary method of implanting a prosthetic cardiac valve.

FIG. 12A illustrates the basic anatomy of the left side of a patient's heart including the left atrium LA and left ventricle LV. Pulmonary veins PV return blood from the lungs to the left atrium and the blood is then pumped from the left atrium into the left ventricle across the mitral valve MV. The mitral valve includes an anterior leaflet AL on an anterior side A of the valve and a posterior leaflet PL on a posterior side P of the valve. The leaflets are attached to chordae tendineae CT which are subsequently secured to the heart walls with papillary muscles PM. The blood is then pumped out of the left ventricle into the aorta Ao with the aortic valve AV preventing regurgitation.

Figure 12B:
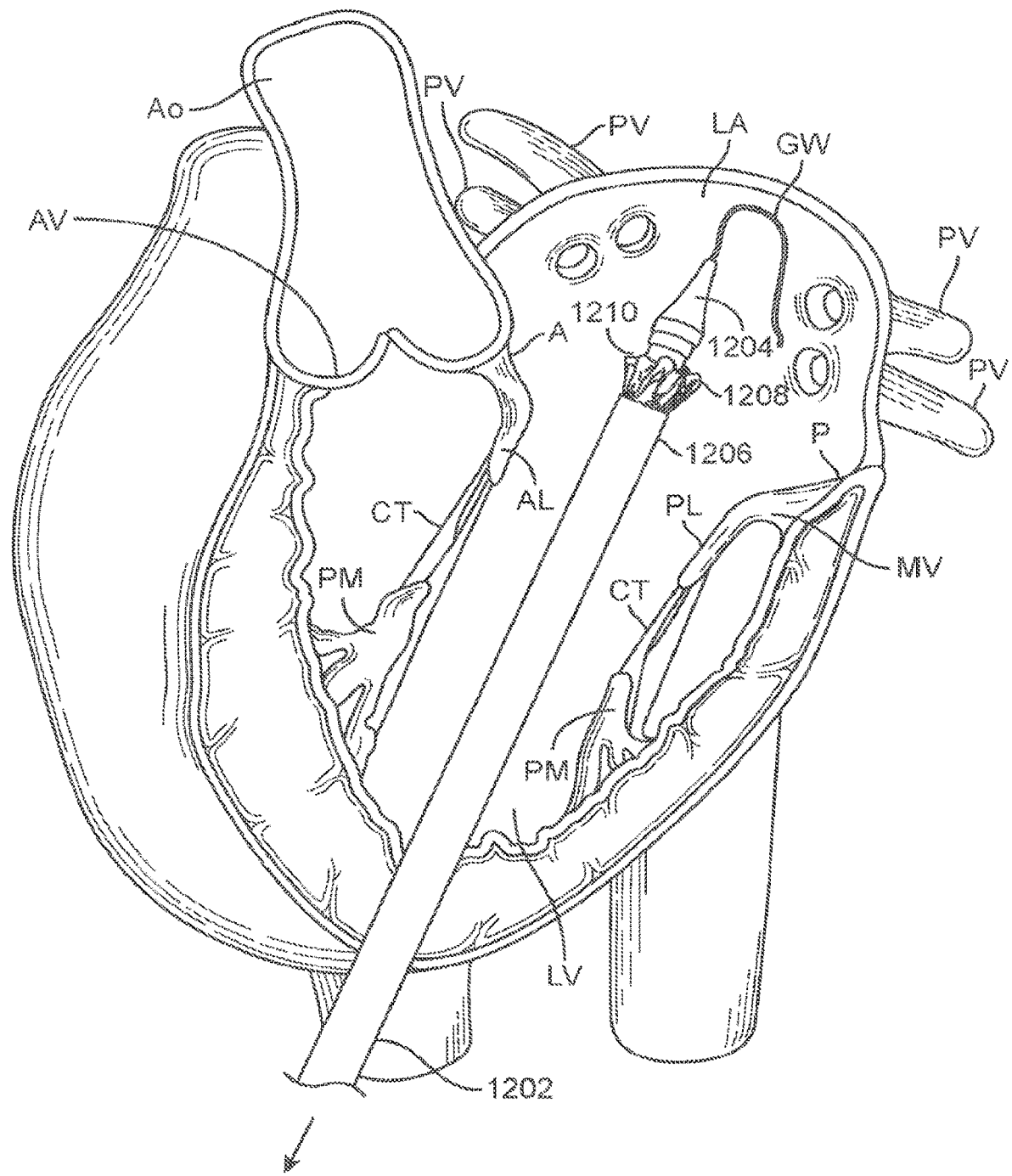
Figure 12C:
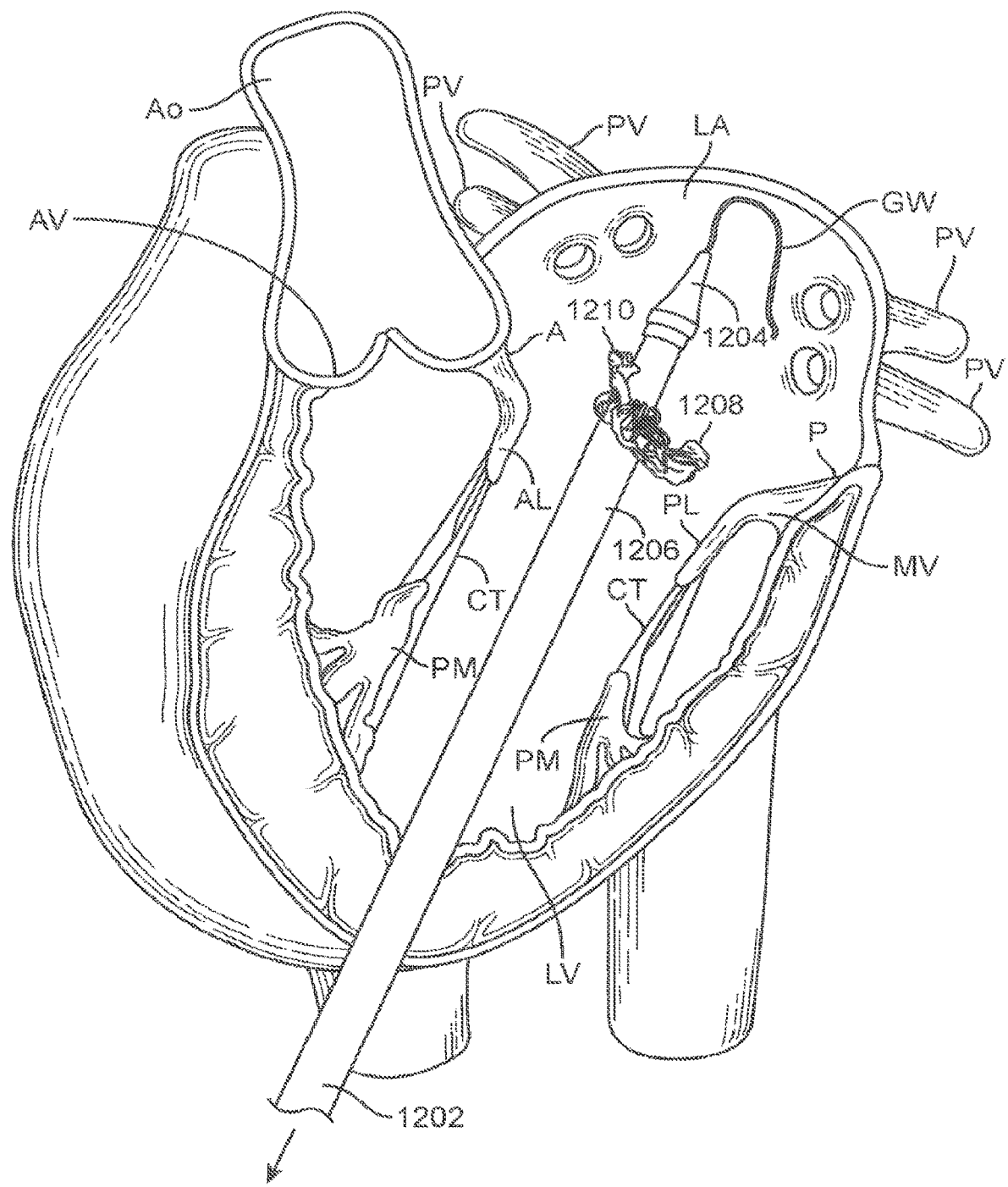
Figure 12D:
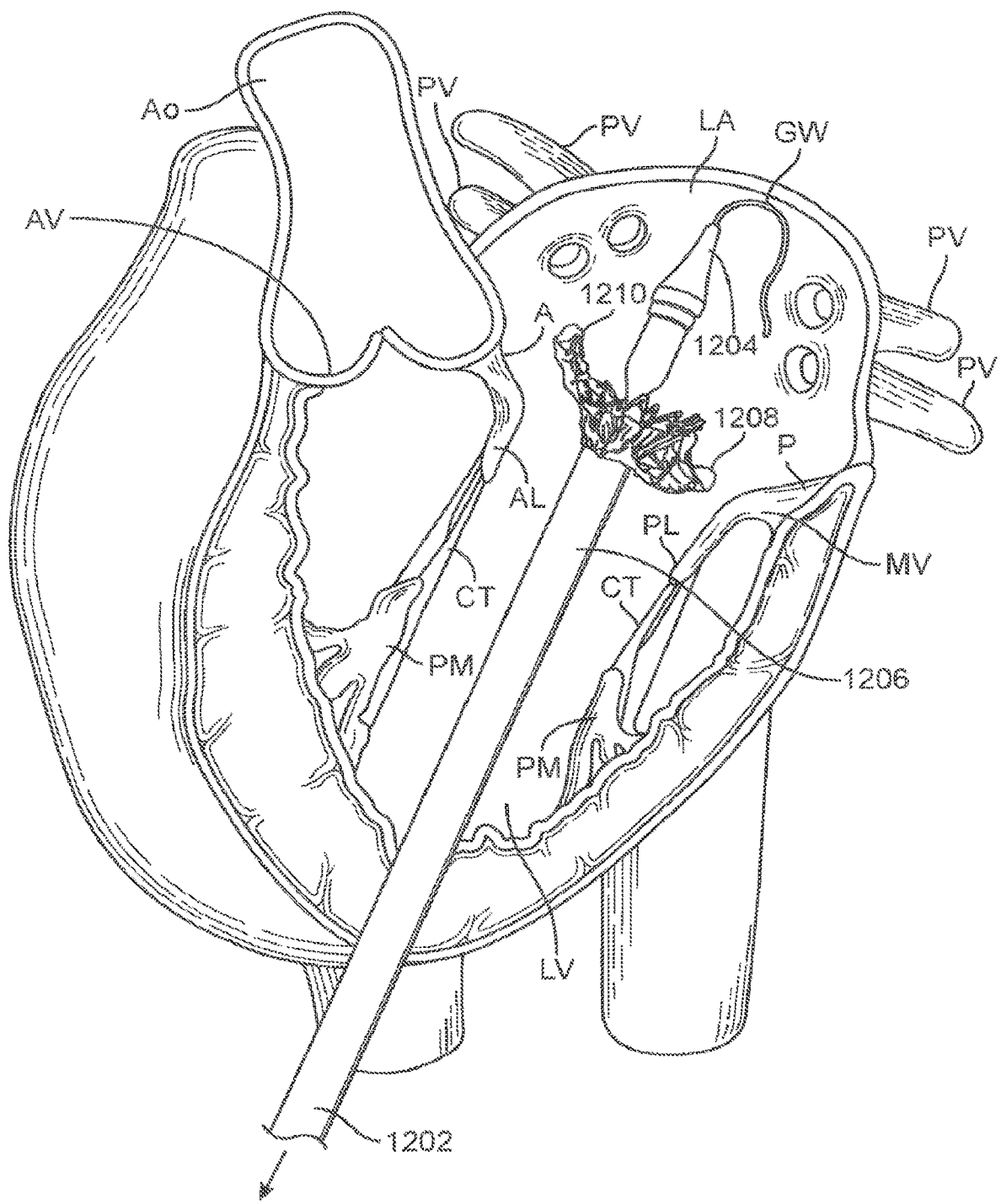

FIG. 12B illustrates transapical delivery of a delivery system 1202 through the apex of the heart into the left atrium LA via the left ventricle LV. The delivery system 1202 may be advanced over a guidewire GW into the left atrium, and a tissue penetrating tip 1204 helps the delivery system pass through the apex of the heart by dilating the tissue and forming a larger channel for the remainder of the delivery system to pass through. The delivery catheter carries prosthetic cardiac valve 1208. Once the distal portion of the delivery system has been advanced into the left atrium, the outer sheath 1206 may be retracted proximally (e.g. toward the operator) thereby removing the constraint from the atrial portion of the prosthetic valve 1208. This allows the atrial skirt 1210 to self-expand radially outward. In FIG. 12C, as the outer sheath is further retracted, the atrial skirt continues to self-expand and peek out, until it fully deploys as seen in FIG. 12D. The atrial skirt may have a cylindrical shape or it may be D-shaped as discussed above with a flat anterior portion and a cylindrical posterior portion so as to avoid interfering with the aortic valve and other aspects of the left ventricular outflow tract. The prosthesis may be oriented and properly positioned by rotating the prosthesis and visualizing the alignment element previously described. Also, the prosthetic cardiac valve may be advanced upstream or downstream to properly position the atrial skirt. In preferred embodiments, the atrial skirt forms a flange that rests against a superior surface of the mitral valve and this anchors the prosthetic valve and prevents it from unwanted movement downstream into the left ventricle.

Figure 12E:
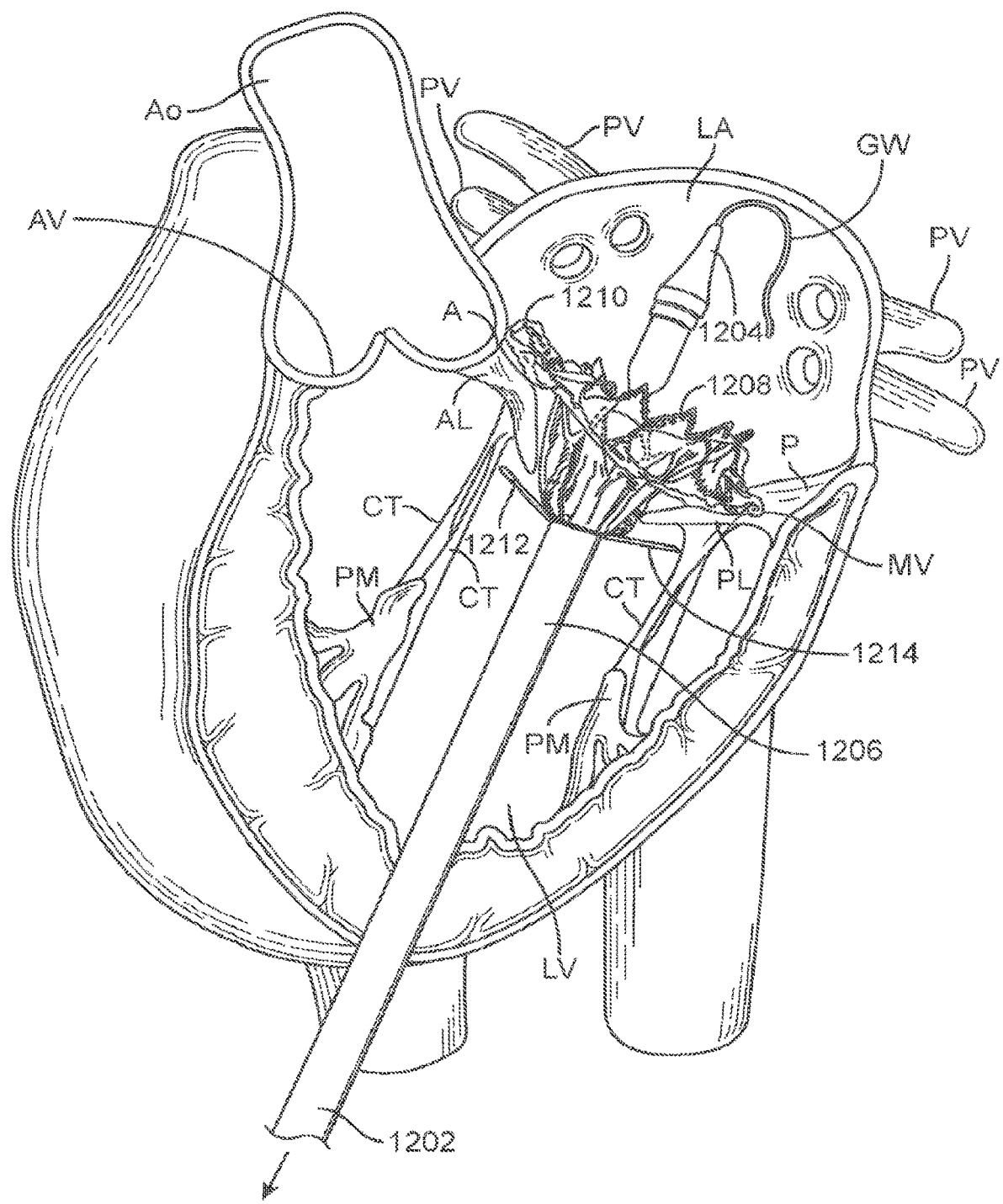
Figure 12F:
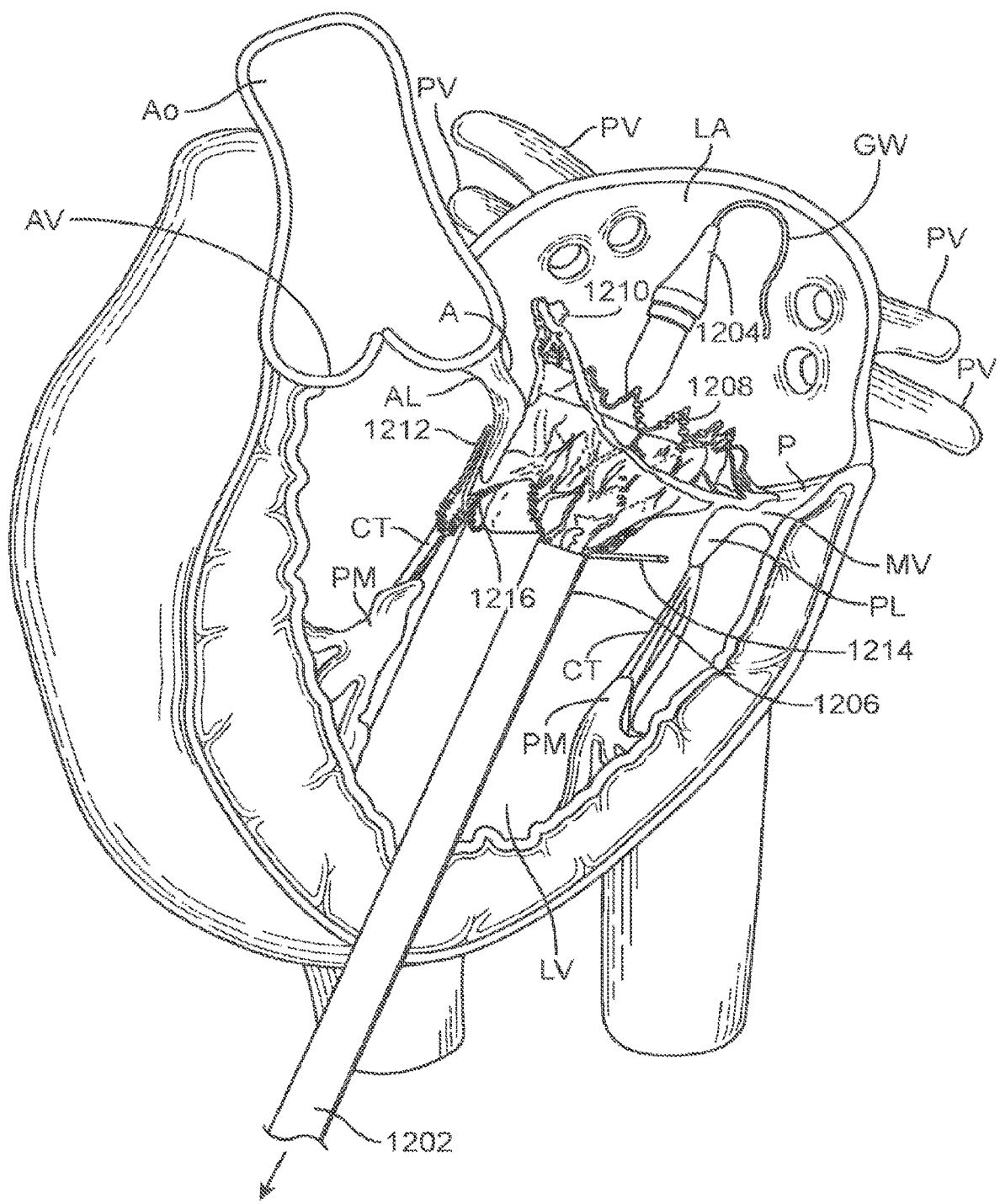

As the outer sheath 1206 continues to be proximally retracted, the annular region of the prosthetic cardiac valve self-expands within the valve annulus. The annular region also preferably has the D-shaped geometry, although it may also be cylindrical or have other geometries to match the native anatomy. In FIG. 12E, retraction of sheath 1206 eventually allows both the anterior 1212 and posterior 1214 tabs to partially self-expand outward preferably without engaging the anterior or posterior leaflets or the chordae tendineae. In this embodiment, further retraction of the outer sheath 1206 then allows both the anterior tabs 1212 (only one visible in this view) to complete their self-expansion so that the anterior leaflet is captured between an inner surface of each of the anterior tabs and an outer surface of the ventricular skirt 1216, as illustrated in FIG. 12F. The posterior tab 1214 remains partially open, but has not completed its expansion yet. Additionally, the tips of the anterior tabs also anchor into the left and right fibrous trigones of the mitral valve, as will be illustrated in greater detail below.

Figure 12G:
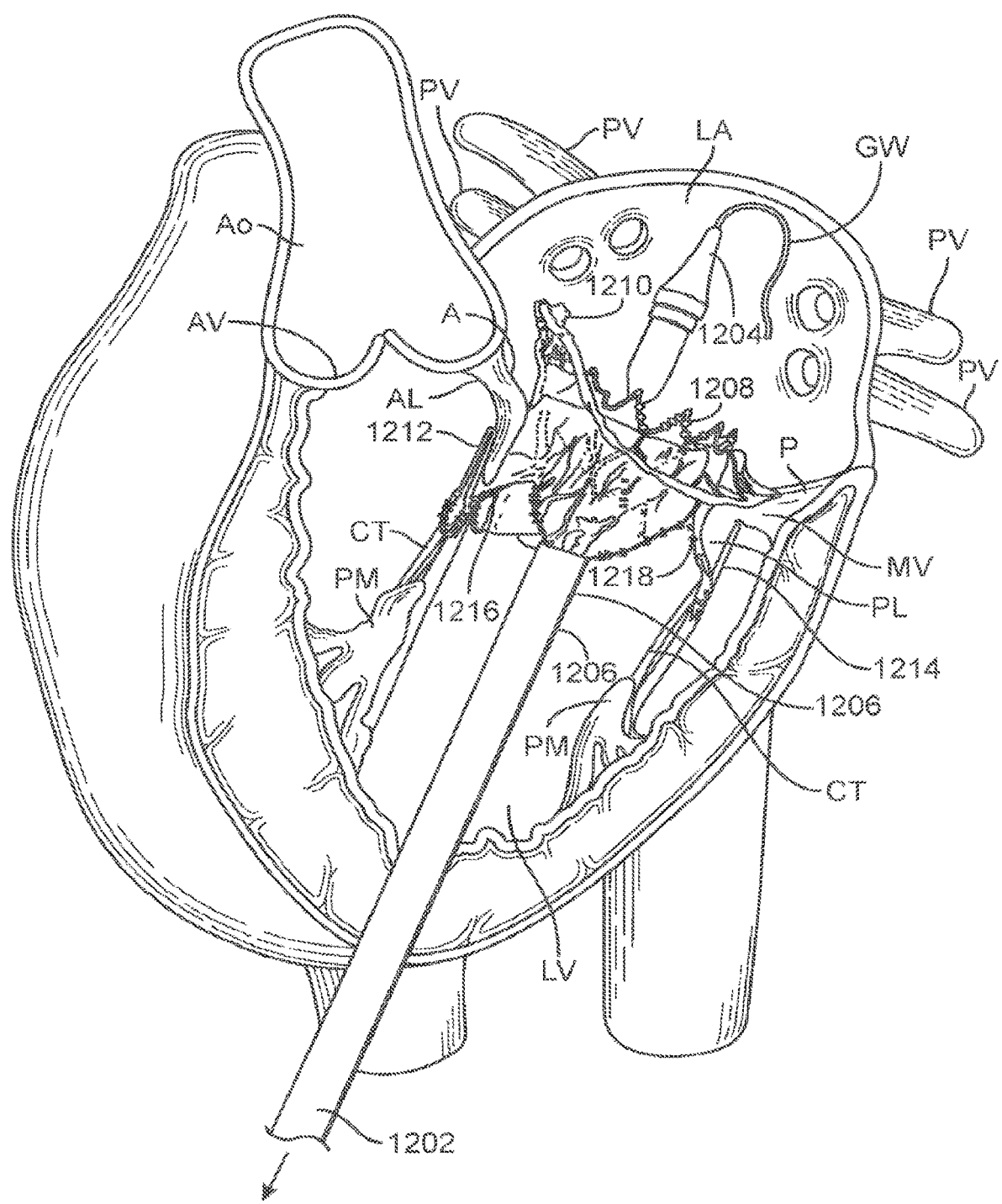
Figure 12H:
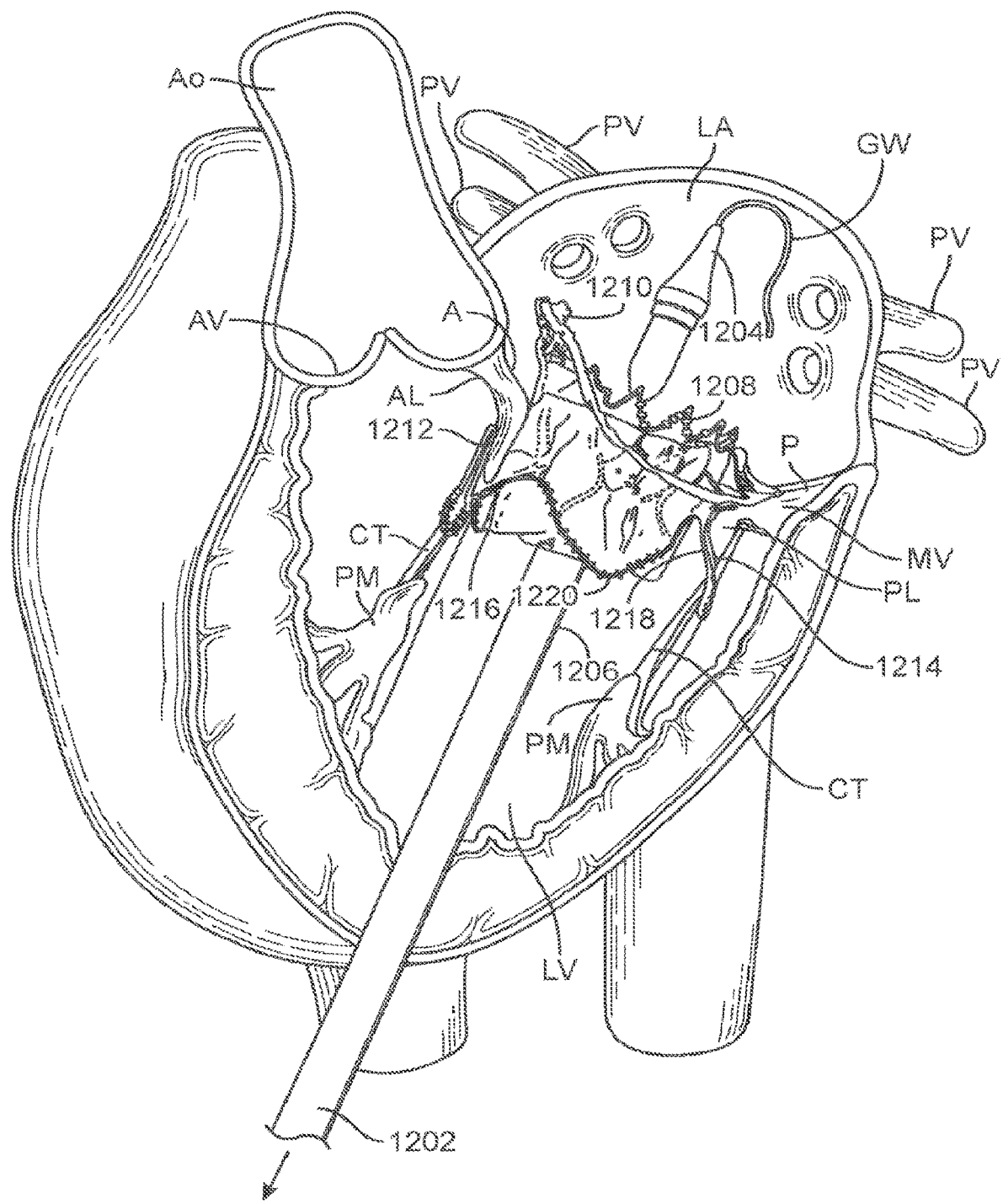

In FIG. 12G, further retraction of the outer sheath 1206 then releases the constraints from the posterior tab 1214 allowing it to complete its self-expansion, thereby capturing the posterior leaflet PL between an inner surface of the posterior tab 1214 and an outer surface of the ventricular skirt 1218. In FIG. 12H, the sheath is retracted further releasing the ventricular skirt 1220 and allowing the ventricular skirt 1220 to radially expand outward, further capturing the anterior and posterior leaflets between the outer surface of the ventricular skirt and their respective anterior or posterior tabs. Expansion of the ventricular skirt also pushes the anterior and posterior leaflets outward, thereby ensuring that the native leaflets do not interfere with any portion of the prosthetic valve or the prosthetic valve leaflets. The prosthetic valve is now anchored in position above the mitral valve, along the annulus, to the valve leaflets, and below the mitral valve, thereby securing it in position.

Figure 12I:
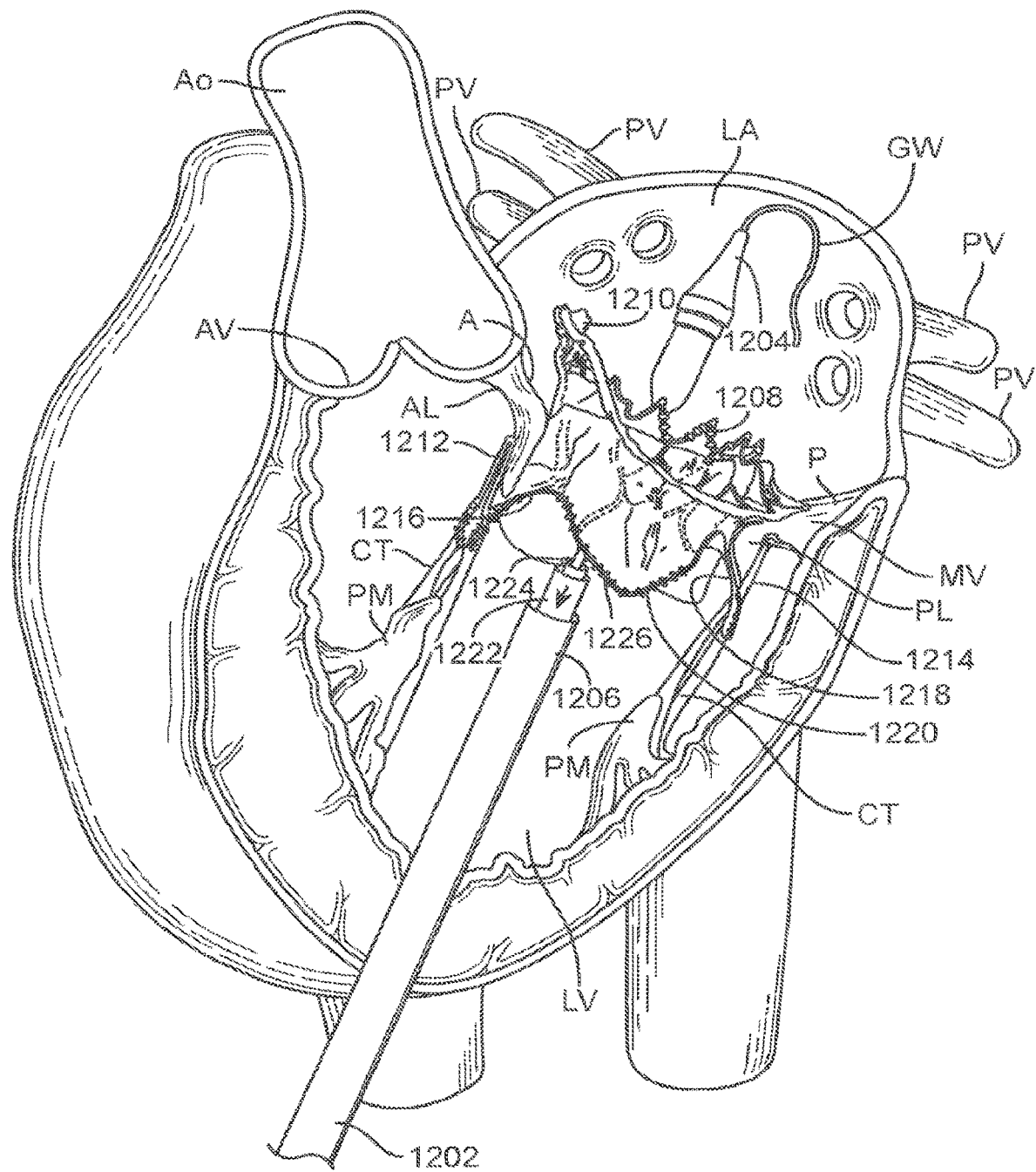
Figure 12J:
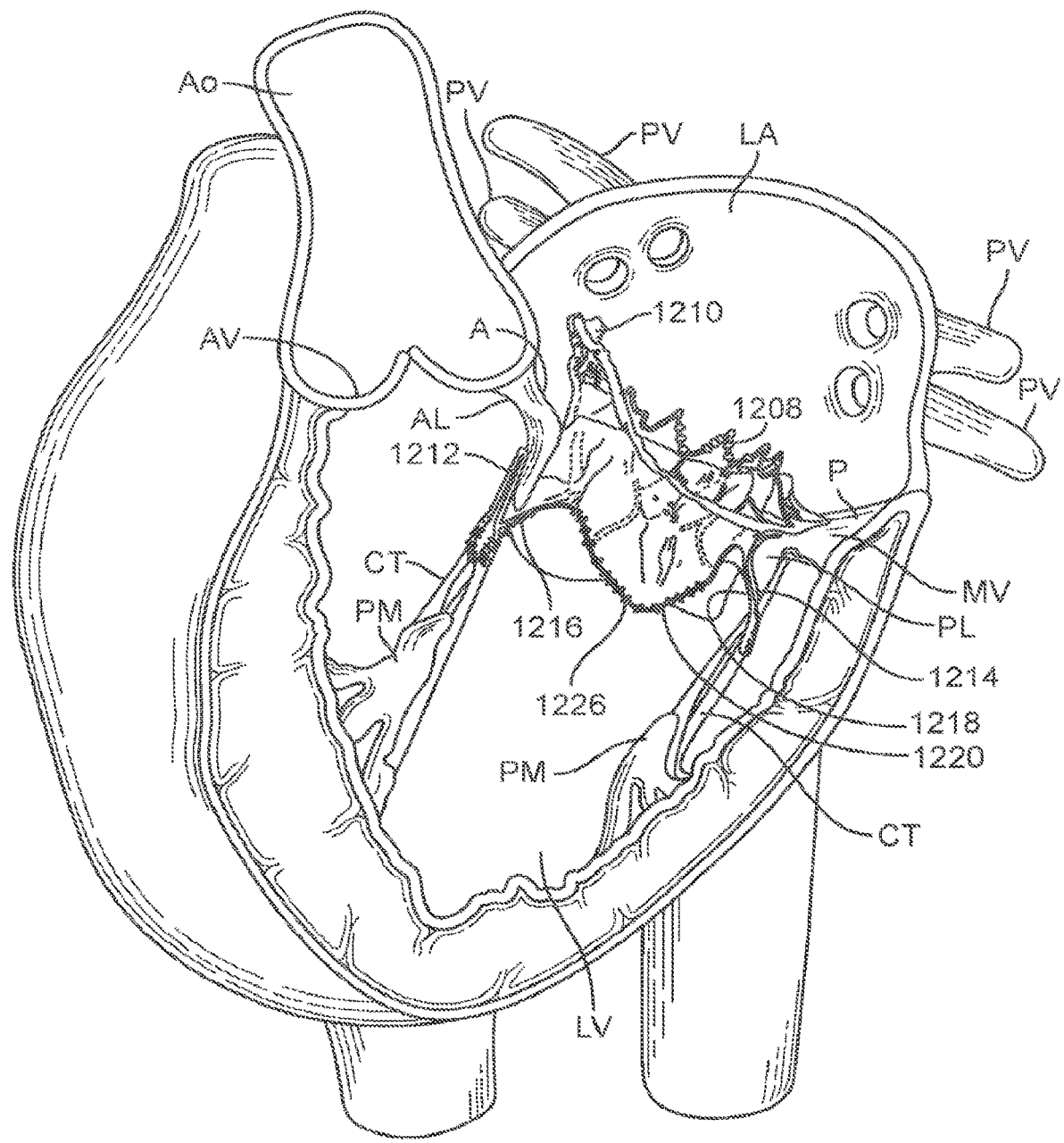

Further actuation of the delivery device now retracts the outer sheath 1206 and the bell catheter shaft 1222 so as to remove the constraint from the hub catheter 1224, as illustrated in FIG. 12I. This permits the prosthetic valve commissures 1226 to be released from the hub catheter, thus the commissures expand to their biased configuration. The delivery system 1202 and guidewire GW are then removed, leaving the prosthetic valve 1208 in position where it takes over for the native mitral valve, as seen in FIG. 12J.

Figure 12K:
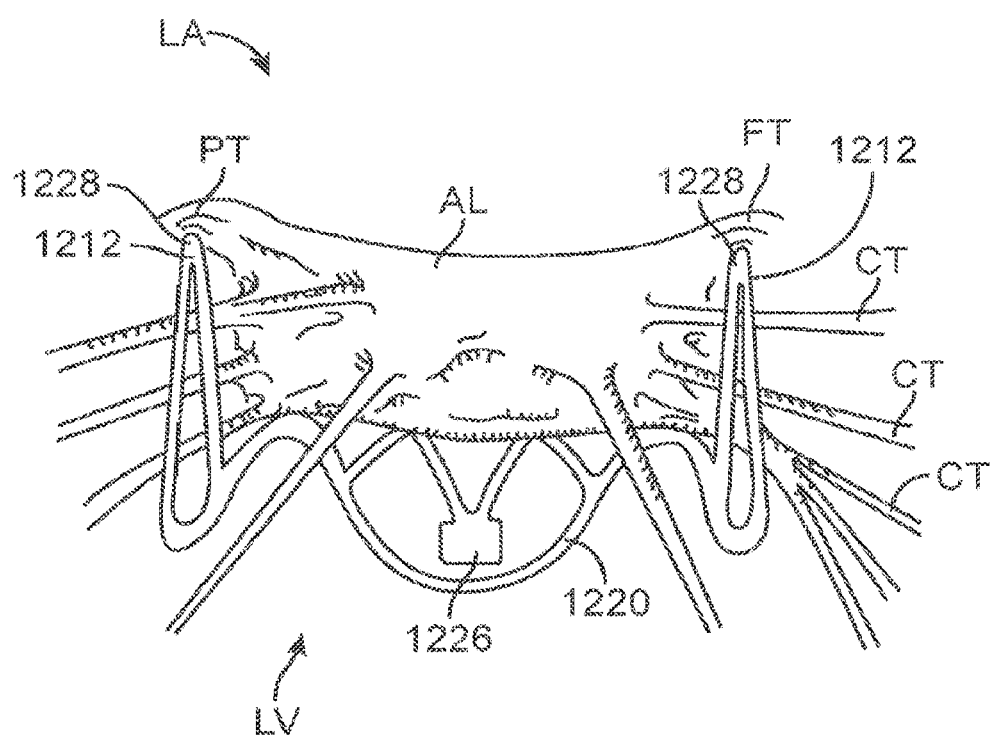
Figure 12L:
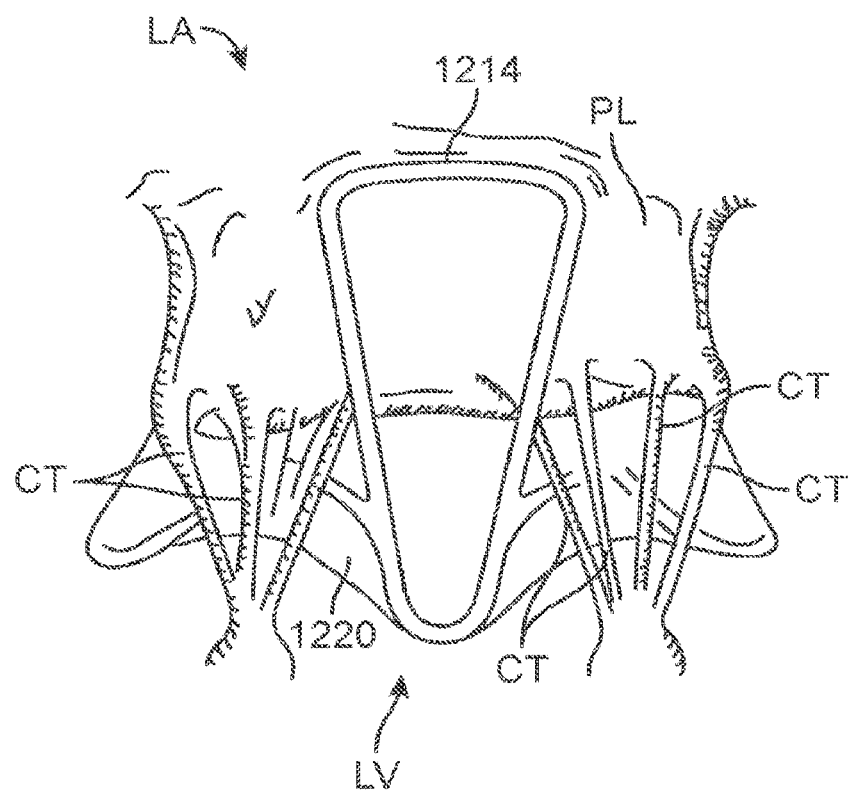

FIGS. 12K and 12L highlight engagement of the anterior and posterior tabs with the respective anterior and posterior leaflets. In FIG. 12K, after anterior tabs 1212 have been fully expanded, they capture the anterior leaflet AL and adjacent chordae tendineae between an inside surface of the anterior tab and an outer surface of the ventricular skirt 1220. In other words, the anterior tabs 1212 advance under (toward the ventricle) and behind the anterior leaflet AL and adjacent chordae tendineae, before the ventricular skirt 1220 expands and pushes out to capture the anterior leaflet AL and adjacent chordae tendinae between the ventricular skirt 1220 and the anterior tabs 1212. Moreover, the tips 1228 of the anterior tabs 1212 are engaged with the fibrous trigones FT of the anterior side of the mitral valve. The fibrous trigones are fibrous regions of the valve thus the anterior tabs further anchor the prosthetic valve into the native mitral valve anatomy. One anterior tab anchors into the left fibrous trigone, and the other anterior tabs anchors into the right fibrous trigone. The trigones are on opposite sides of the anterior side of the leaflet. FIG. 12L illustrates engagement of the posterior tab 1214 with the posterior leaflet PL which is similarly captured between an inner surface of the posterior tab and an outer surface of the ventricular skirt 1220. Additionally, adjacent chordae tendineae are also captured between the posterior tab and ventricular skirt. In other words, the posterior tab 1214 advance under toward the ventricle) and behind the posterior leaflet PL and adjacent chordae tendineae, before the ventricular skirt 1220 expands and pushes out to capture the posterior leaflet PL and adjacent chordae tendinae between the ventricular skirt 1220 and the posterior tab 1214.

FIGS. 13A-13L illustrate another exemplary embodiment of a delivery method. This embodiment is similar to that previously described, with the major difference being the order in which the prosthetic cardiac valve self-expands into engagement with the mitral valve. Any delivery device or any prosthetic cardiac valve disclosed herein may be used, however in preferred embodiments, the embodiment of FIG. 7 is used. Varying the order may allow better positioning of the implant, easier capturing of the valve leaflets, and better anchoring of the implant. This exemplary method also preferably uses a transapical route, although transseptal may also be used.

Figure 13A:
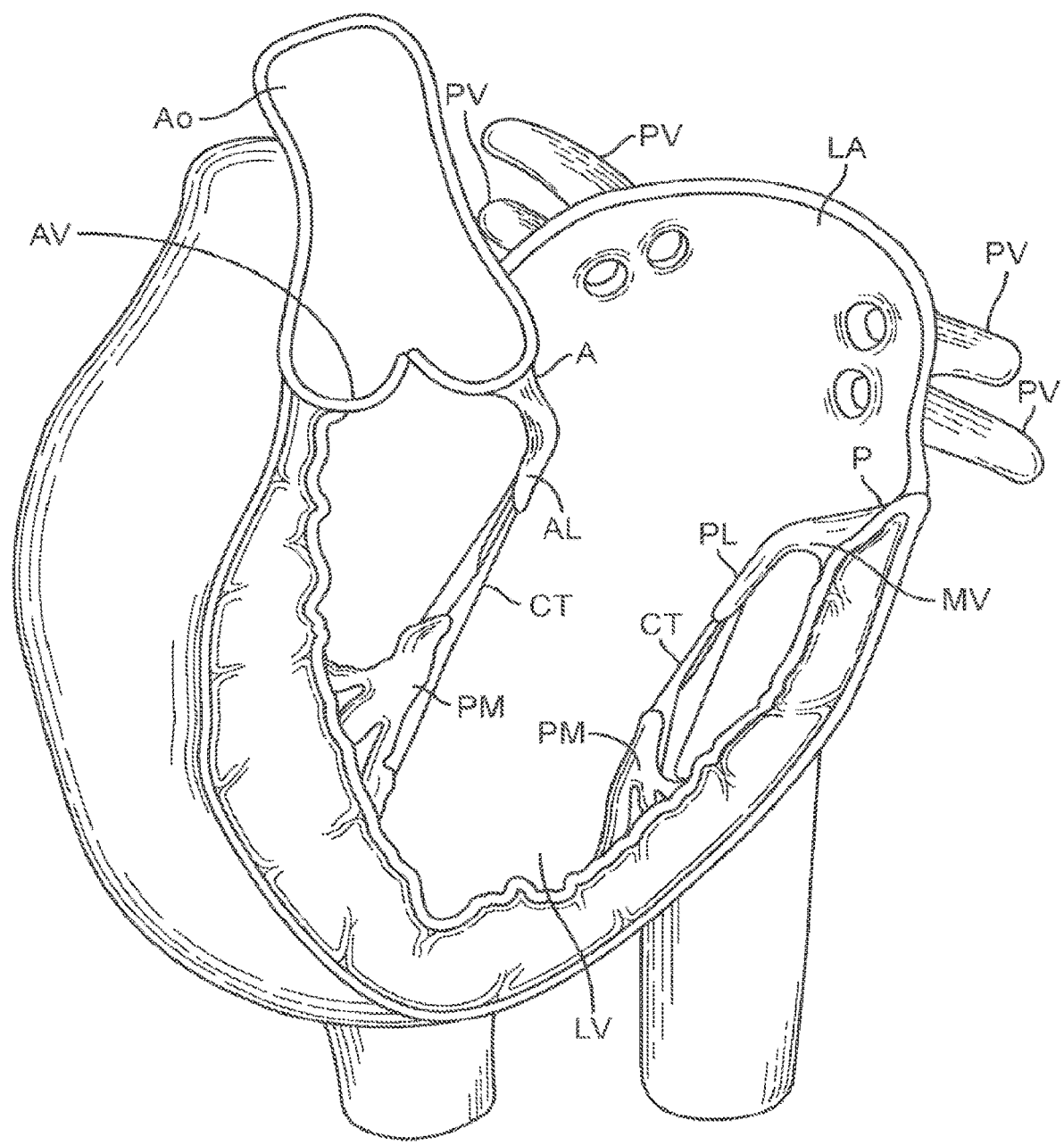
FIGS. 13A-13L illustrate another exemplary method of implanting a prosthetic cardiac valve.

FIG. 13A illustrates the basic anatomy of the left side of a patient's heart including the left atrium LA and left ventricle LV. Pulmonary veins PV return blood from the lungs to the left atrium and the blood is then pumped from the left atrium into the left ventricle across the mitral valve MV. The mitral valve includes an anterior leaflet AL on an anterior side A of the valve and a posterior leaflet PL on a posterior side P of the valve. The leaflets are attached to chordae tendineae CT which are subsequently secured to the heart walls with papillary muscles PM. The blood is then pumped out of the left ventricle into the aorta AO with the aortic valve AV preventing regurgitation.

Figure 13B:
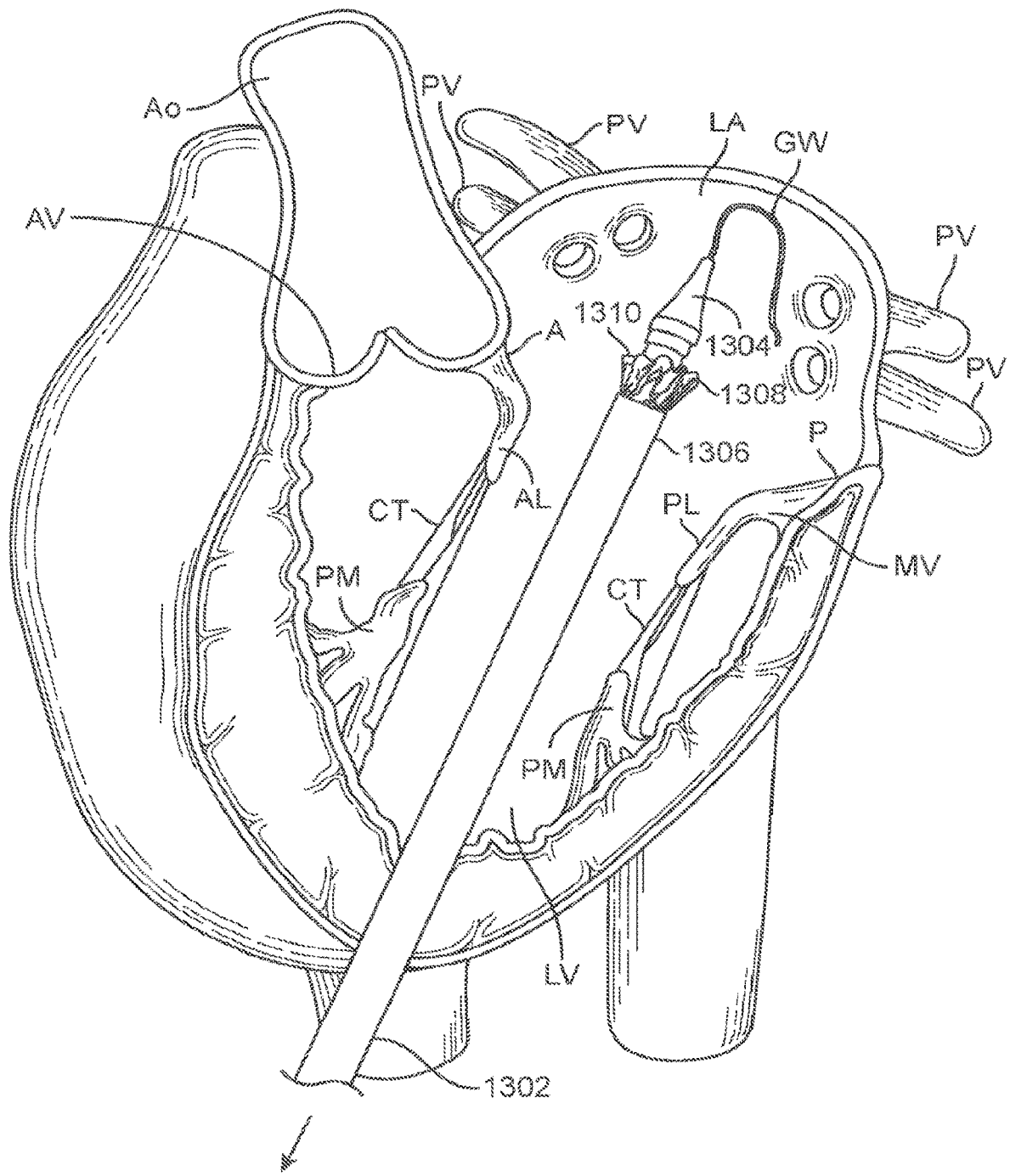
Figure 13C:
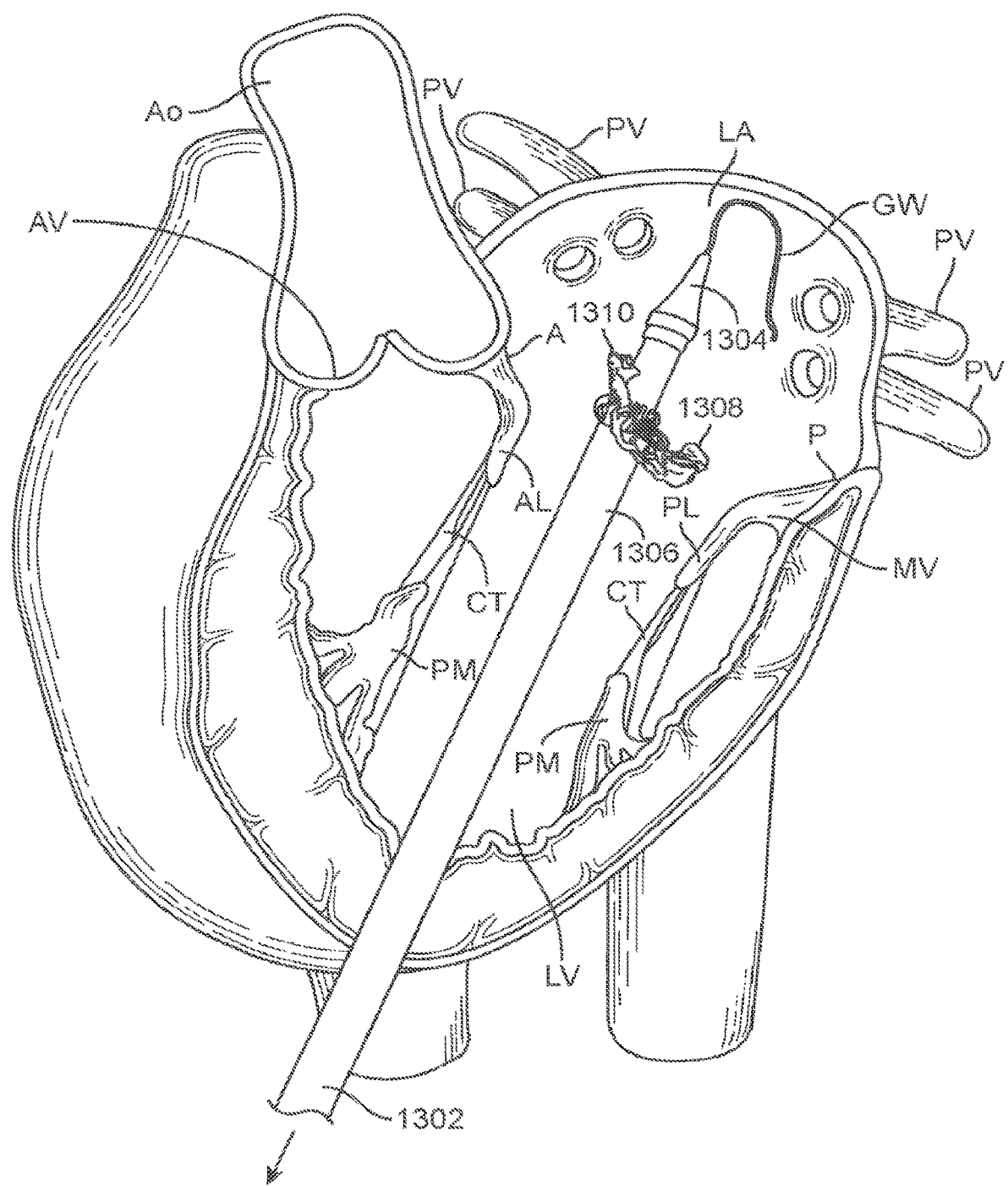
Figure 13D:
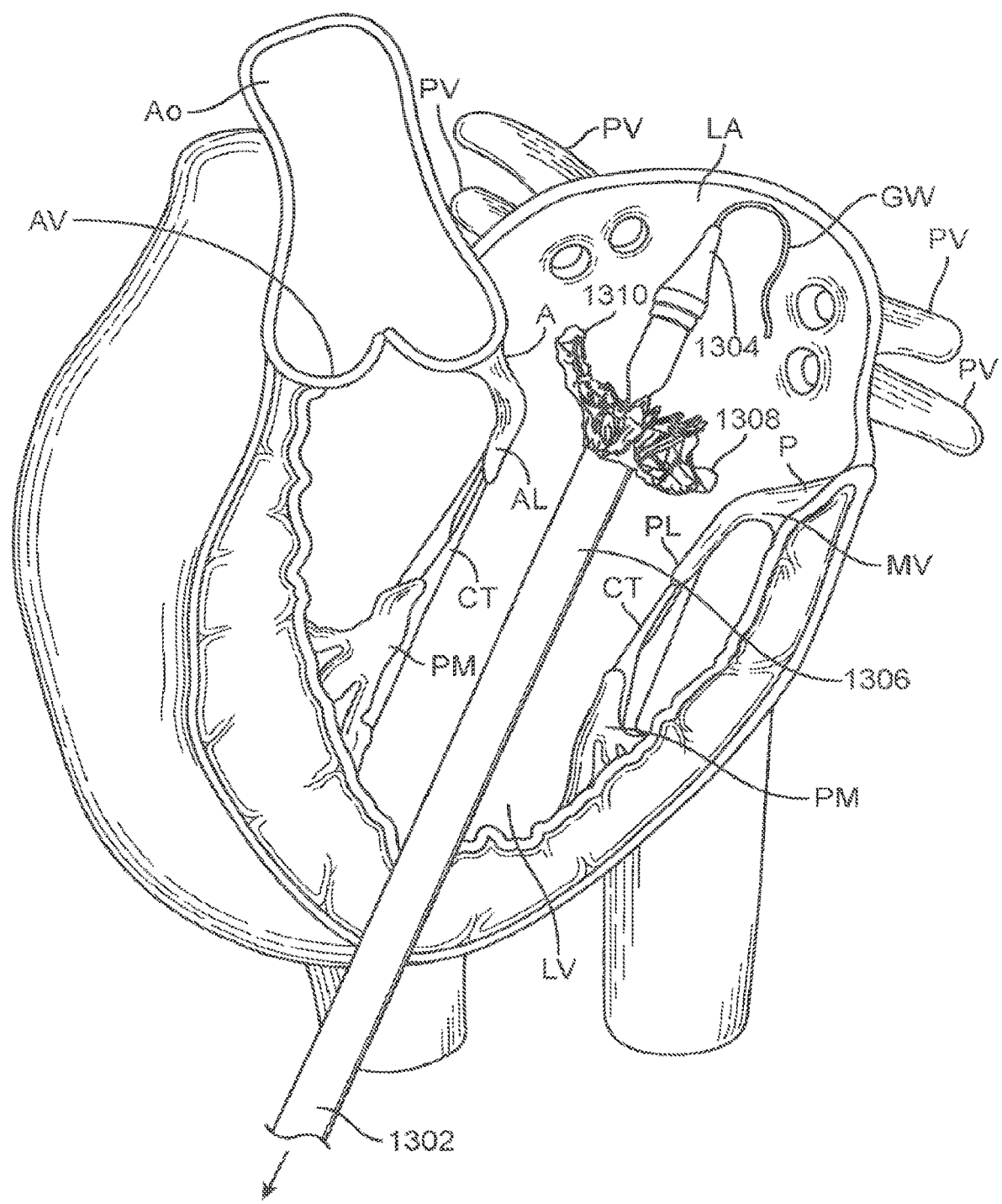

FIG. 13B illustrates transapical delivery of a delivery system 1302 through the apex of the heart into the left atrium LA via the left ventricle LV. The delivery system 1302 may be advanced over a guidewire GW into the left atrium, and a tissue penetrating tip 1304 helps the delivery system pass through the apex of the heart by dilating the tissue and forming a larger channel for the remainder of the delivery system to pass through. The delivery catheter carries prosthetic cardiac valve 1308. Once the distal portion of the delivery system has been advanced into the left atrium, the outer sheath 1306 may be retracted proximally (e.g. toward the operator) thereby removing the constraint from the atrial portion of the prosthetic valve 1308. This allows the atrial skirt 1310 to self-expand radially outward. In FIG. 13C, as the outer sheath is further retracted, the atrial skirt continues to self-expand and peek out, until it fully deploys as seen in FIG. 13D. The atrial skirt may have a cylindrical shape or it may be D-shaped as discussed above with a flat anterior portion and a cylindrical posterior portion so as to avoid interfering with the aortic valve and other aspects of the left ventricular outflow tract. The prosthesis may be oriented and properly positioned by rotating the prosthesis and visualizing the alignment element previously described. Also, the prosthetic cardiac valve may be advanced upstream or downstream to properly position the atrial skirt. In preferred embodiments, the atrial skirt forms a flange that rests against a superior surface of the mitral valve and this anchors the prosthetic valve and prevents it from unwanted movement downstream into the left ventricle.

Figure 13E:
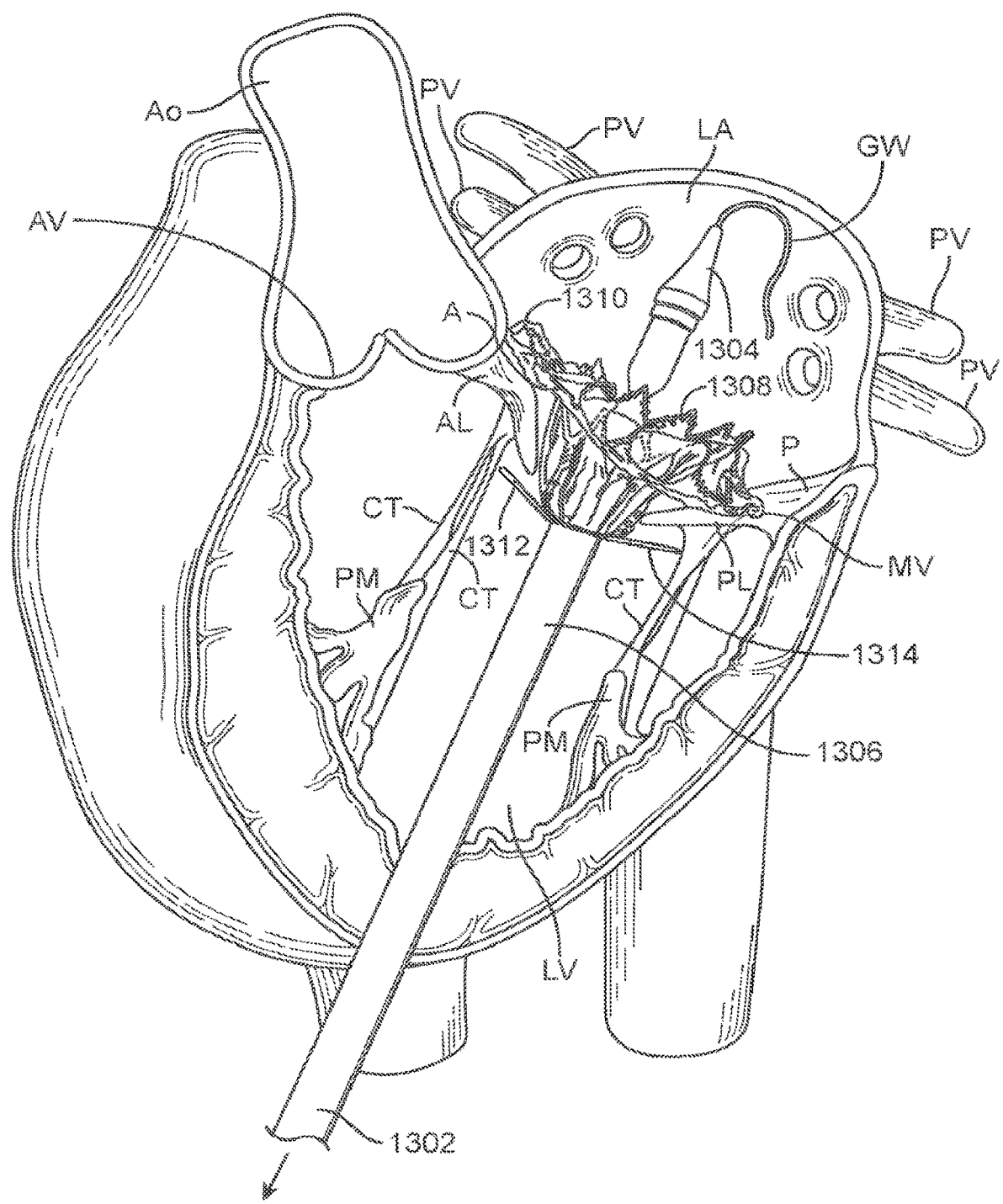
Figure 13F:
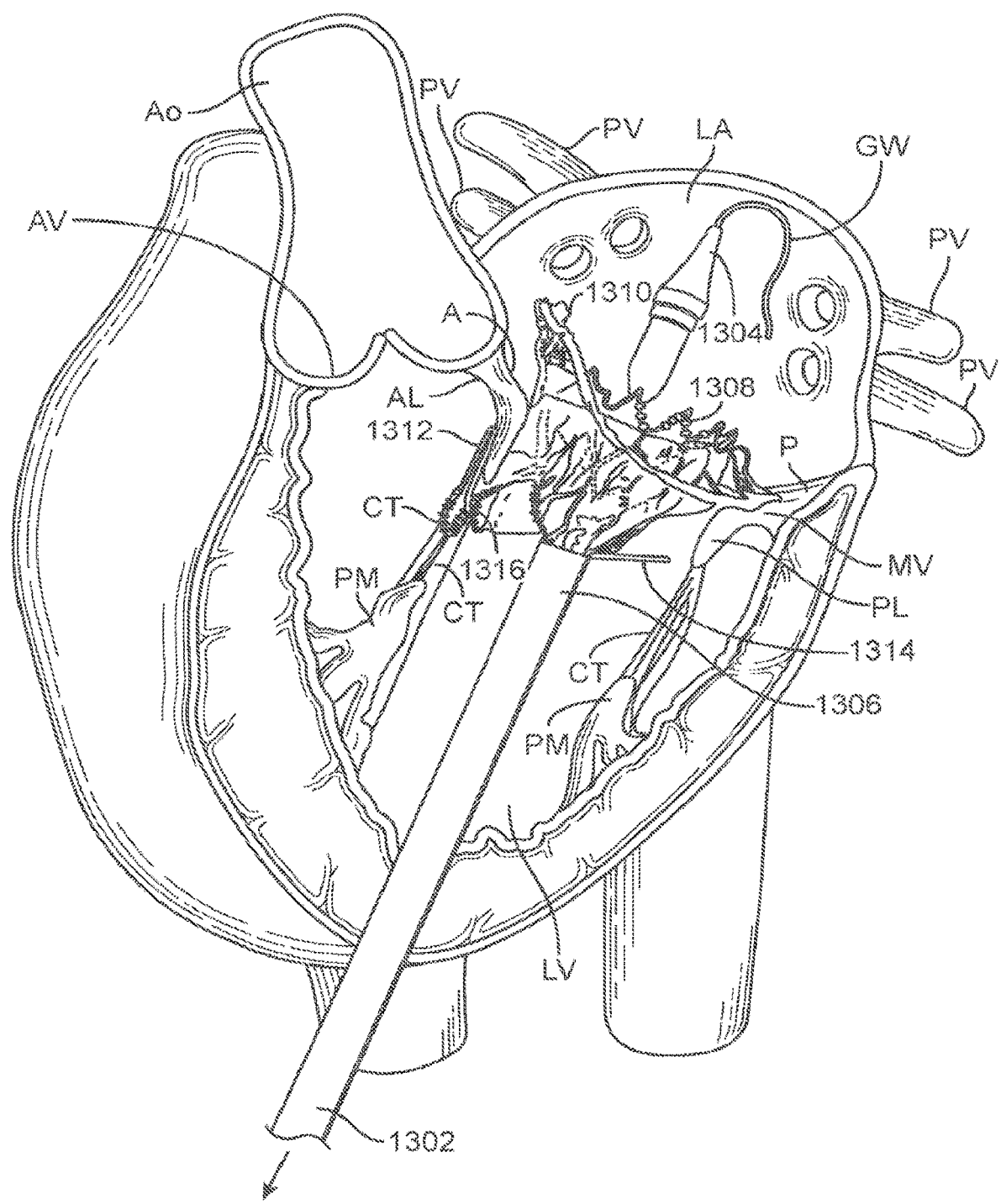

As the outer sheath 1306 continues to be proximally retracted, the annular region of the prosthetic cardiac valve self-expands within the valve annulus. The annular region also preferably has the D-shaped geometry, although it may also be cylindrical or have other geometries to match the native anatomy. In FIG. 13E, retraction of sheath 1306 eventually allows both the anterior 1312 and posterior 1314 tabs to partially self-expand outward preferably without engaging the anterior or posterior leaflets or the chordae tendineae. In this embodiment, further retraction of the outer sheath 1306 then allows both the anterior tabs 1312 (only one visible in this view) to complete their self-expansion so that the anterior leaflet is captured between an inner surface of each of the anterior tabs and an outer surface of the ventricular skirt 1316, as illustrated in FIG. 13F. The posterior tab 1214 remains partially open, but has not completed its expansion yet. Additionally, the tips of the anterior tabs also anchor into the left and right fibrous trigones of the mitral valve, as will be illustrated in greater detail below.

Figure 13G:
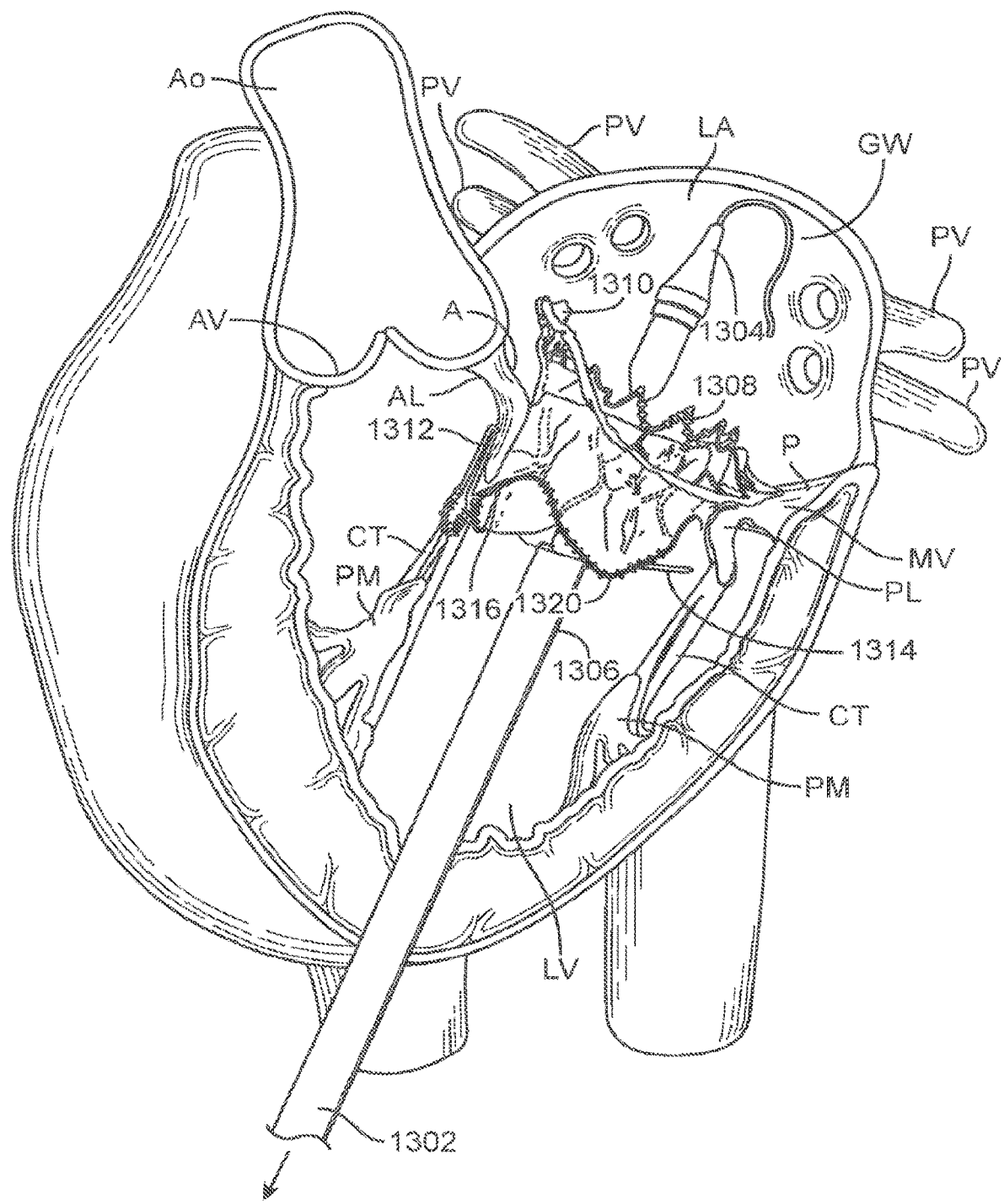
Figure 13H:
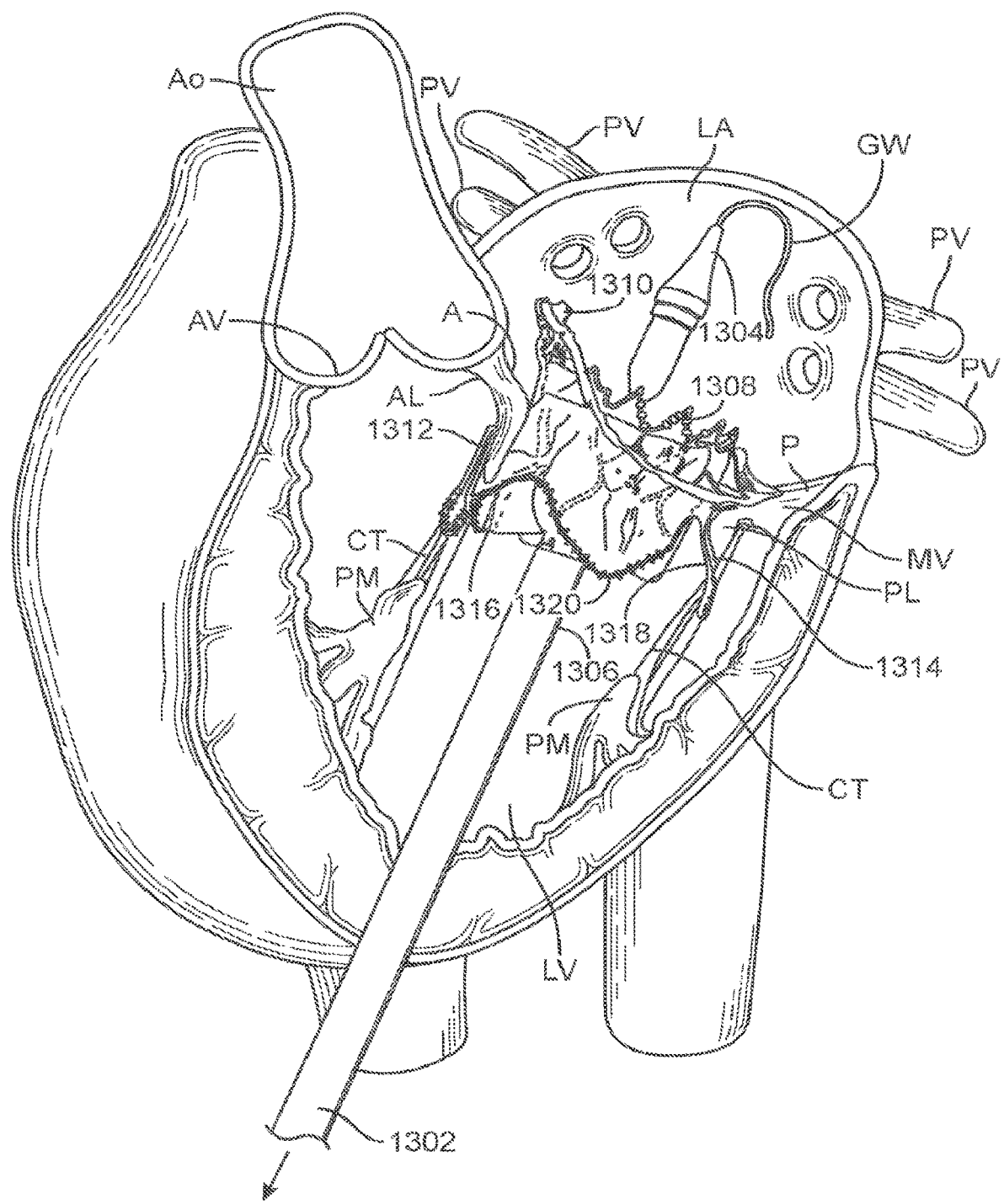

In FIG. 13G, further retraction of the outer sheath 1306 then releases the constraint from the ventricular skirt 1320 allowing the ventricular skirt to radially expand. This then further captures the anterior leaflets AL between the anterior tab 1312 and the ventricular skirt 1316. Expansion of the ventricular skirt also pushes the anterior and posterior leaflets outward, thereby ensuring that the native leaflets do not interfere with any portion of the prosthetic valve or the prosthetic valve leaflets. Further retraction of sheath 1306 as illustrated in FIG. 13H releases the constraint from the posterior tab 1314 allowing it to complete its self-expansion, thereby capturing the posterior leaflet PL between an inner surface of the posterior tab 1314 and an outer surface of the ventricular skirt 1318. The prosthetic valve is now anchored in position above the mitral valve, along the annulus, to the valve leaflets, and below the mitral valve, thereby securing it in position.

Figure 13I:
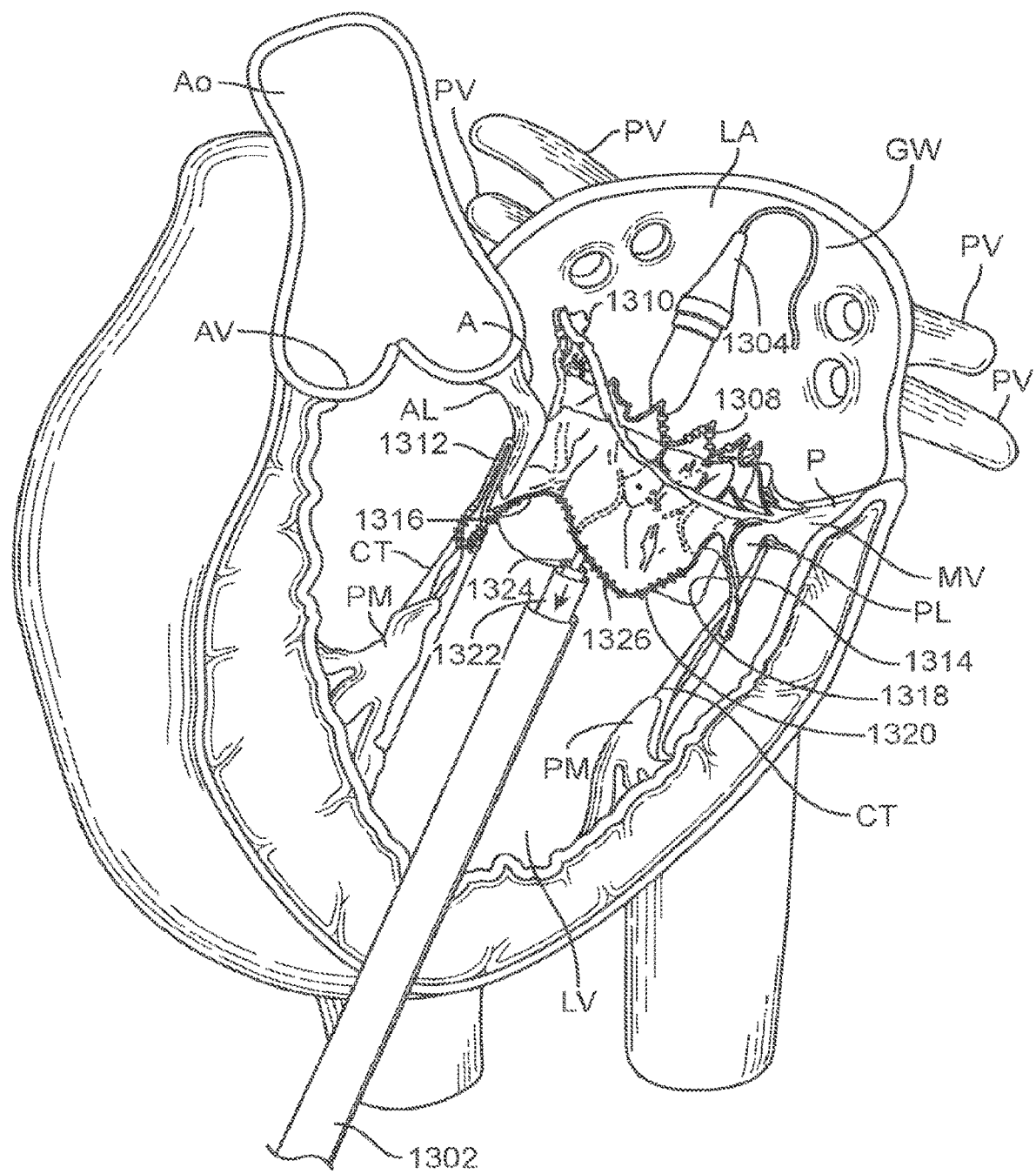
Figure 13J:
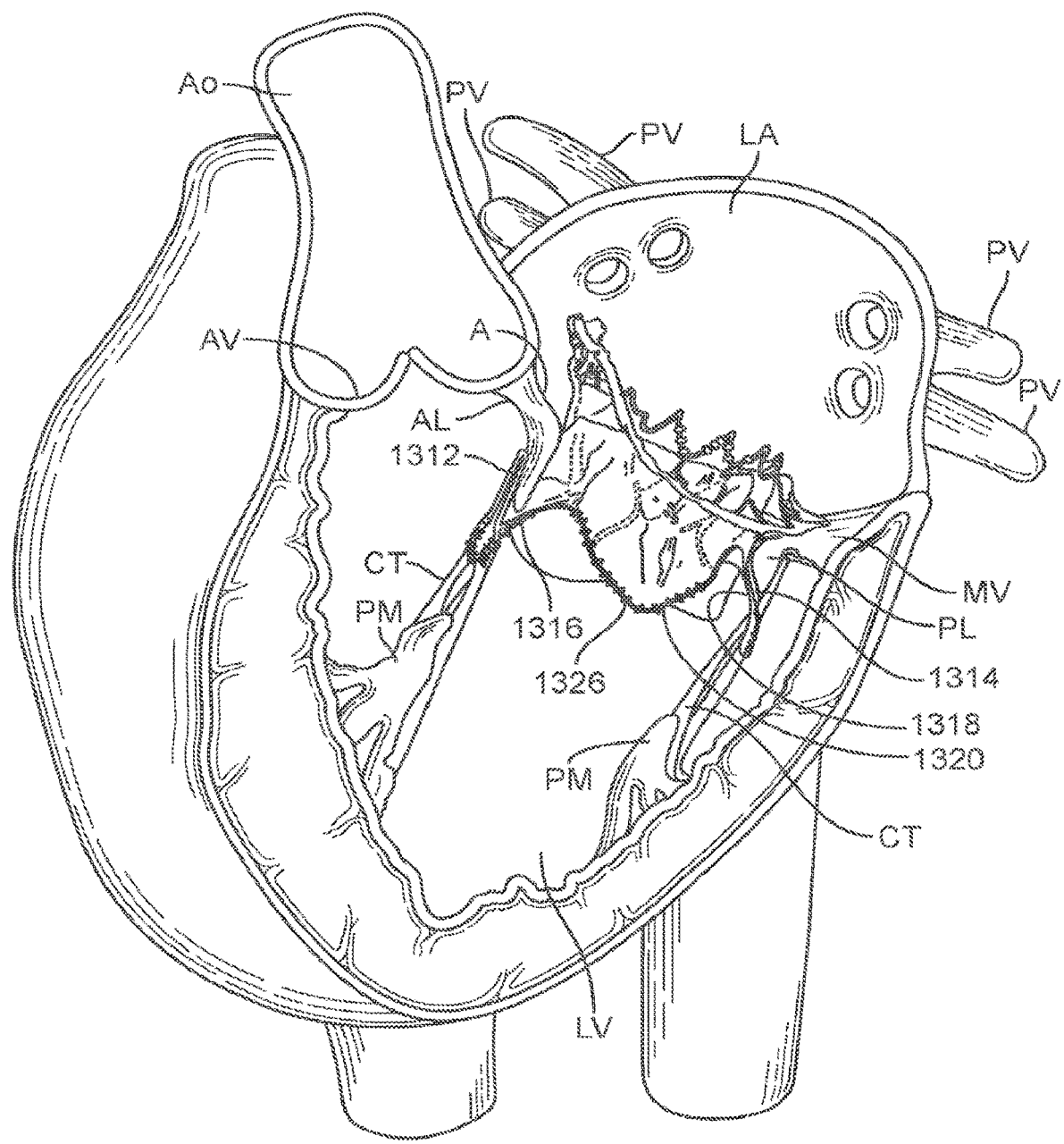

Further actuation of the delivery device now retracts the outer sheath 1306 and the bell catheter shaft 1322 so as to remove the constraint from the hub catheter 1324, as illustrated in FIG. 13I. This permits the prosthetic valve commissures 1326 to be released from the hub catheter, thus the commissures expand to their biased configuration. The delivery system 1302 and guidewire GW are then removed, leaving the prosthetic valve 1308 in position where it takes over for the native mitral valve, as seen in FIG. 13J.

Figure 13K:
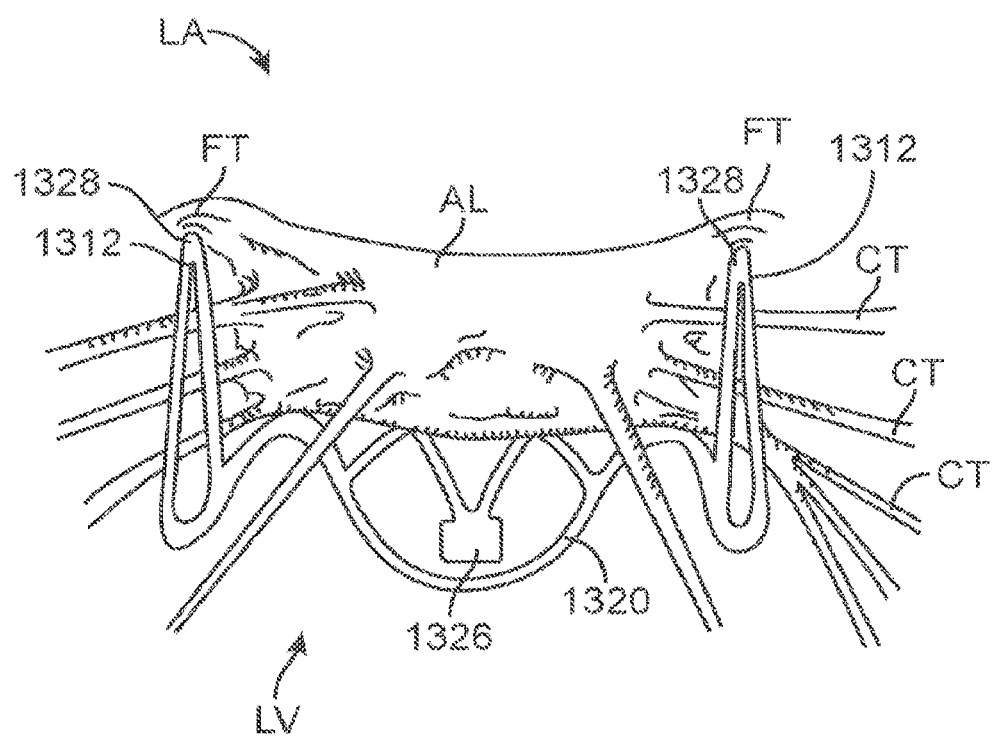
Figure 13L:
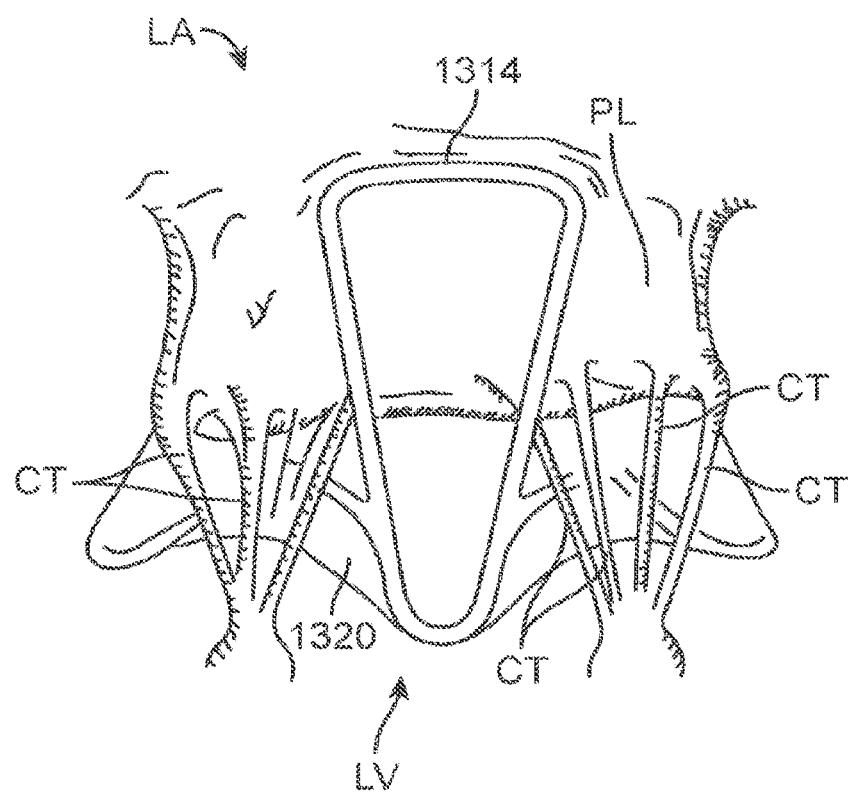

FIGS. 13K and 13L highlight engagement of the anterior and posterior tabs with the respective anterior and posterior leaflet. In FIG. 13K, after anterior tabs 1312 have been fully expanded, they capture the anterior leaflet AL and adjacent chordae tendineae between an inside surface of the anterior tab and an outer surface of the ventricular skirt 1320. Moreover, the tips 1328 of the anterior tabs 1312 are engaged with the fibrous trigones FT of the anterior side of the mitral valve (similarly to anterior tabs 1212 described above). The fibrous trigones are fibrous regions of the valve thus the anterior tabs further anchor the prosthetic valve into the native mitral valve anatomy. One anterior tab anchors into the left fibrous trigone, and the other anterior tabs anchors into the right fibrous trigone. The trigones are on opposite sides of the anterior side of the leaflet. FIG. 13L illustrates engagement of the posterior tab 1314 with the posterior leaflet PL which is captured between an inner surface of the posterior tab and an outer surface of the ventricular skirt 1320 (similarly to posterior tab 1214 described above). Additionally, adjacent chordae tendineae are also captured between the posterior tab and ventricular skirt.

Tab Covering. In the exemplary embodiments described above, the tabs (anterior trigonal tabs and posterior ventricular tab) are generally narrow and somewhat pointy. The embodiment previously described with respect to FIG. 8 includes a horizontal strut on the posterior tab that helps distribute force across a greater area and thereby reduces trauma to the tissue. FIGS. 14A-14D illustrate another embodiment that is preferably used with the anterior trigonal tabs to help reduce trauma. It may also be used with the posterior tab if desired.

Figure 14A:
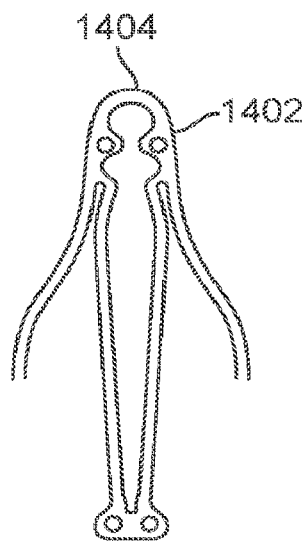
FIGS. 14A-14D illustrate an exemplary embodiment of a tab covering.
Figure 14B:
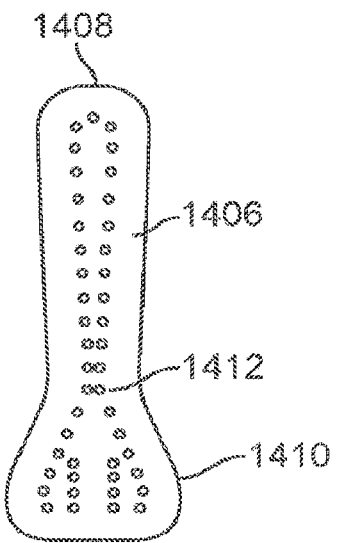
Figure 14C:
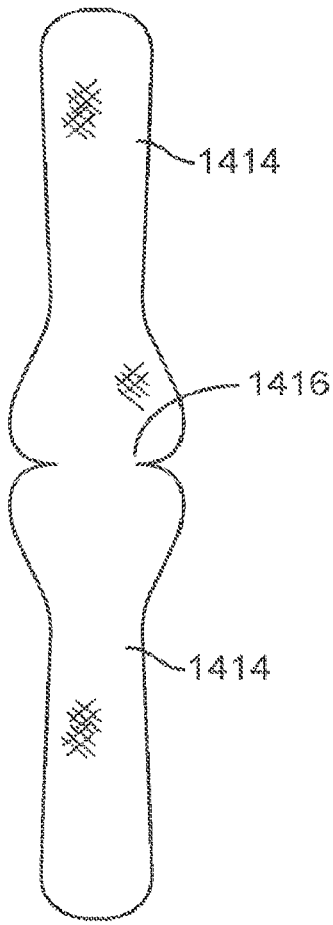
Figure 14D:
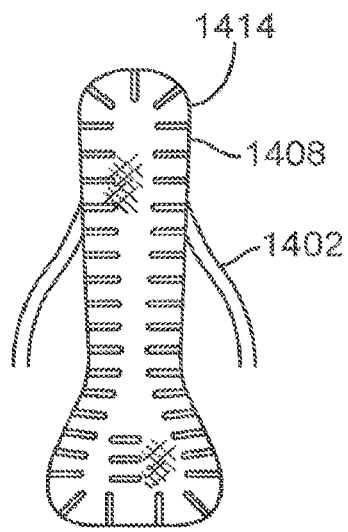

FIG. 14A illustrates an anterior trigonal tab 1402 having a tip 1404. This tip can be narrow and pointy and thereby induce tissue trauma when deployed into the tissue. Therefore, in some embodiments, it may be desirable to place a cover over the tip to help reduce tissue trauma. FIG. 14B illustrates a polymer tab 1406 that may be attached to the trigonal tab 1402. In other embodiments, the tab may be formed from other materials such as fabric, metals, or other materials known in the art. The polymer tab may be laser cut from a sheet of polymer and includes a long axial portion 1408 and an enlarged head region 1410. A plurality of suture holes 1412 may be pre-cut into the polymer tab 1406 and the holes are sized to receive suture material. Precut holes on the polymer tab may be aligned with pre-cut holes on the trigonal tab and then the polymer tab may be secured to the trigonal tab with sutures, adhesives, or other coupling techniques known in the art. A fabric cover 1414 having two symmetric halves separated by a hinged area 1416 is then wrapped around the polymer tab and attached to the polymer tab by sutures, thereby forming a shroud around the trigonal tab. The fabric may be Dacron, ePTEE, or any other biocompatible material known in the art. Thus, the cover increases the surface area of contact between the trigonal tabs and the tissue thereby reducing potential trauma and likelihood of piercing the heart wall. Additionally, the material may allow tissue ingrowth which further helps to anchor the prosthesis. Materials and dimensions are also selected in order to maintain the low profile of the device during delivery in the collapsed configuration.

Sequential Deployment. As discussed above and herein, the deployment of the tabs, particularly the sequence of deployment (and thereby capture and/or engagement of the anterior leaflet AL, the posterior leaflet PL, and the adjacent chordae tendinae), may be controlled by controlling strut length and/or axial position of the anterior and/or posterior tabs. For instance, the axial position of the atrial end of the tabs may be varied to vary when the tabs begin deployment as the constraining sheath is retracted, and the axial position of the ventricular end of the tabs may be varied to vary when the tabs are fully deployed as the constraining sheath is retracted. Particular sequences of deployment may be more optimal to certain anatomies and may allow the prosthetic valve to be more accurately delivered and more securely anchored into position. For example, either the anterior tab(s) or the posterior tab(s) may be more easily visualized than the other in at least some cases, and the more easily visualized tab may be configured to deploy first as a guide to orient the frame during implantation. In at least some cases, the Inventors have found that the posterior tab is easier to visualize using ultrasound and/or fluoroscopy. The sequence of tab deployment may be customized to the individual patient and their anatomy in some cases and the customization may be based on pre-screen imaging data for the individual patient. The tabs that are projected to be more easily visualized, such as by using ultrasound and/or fluoroscopy, may be configured to deploy first. The initially deployed tabs can allow for intermediate movement of the imaging source, e.g., the C-arm controlling the ultrasound or X-ray device for fluoroscopy, so as to provide verification of the initial tab placements. If needed, the prosthetic valve may be repositioned and/or reoriented with the initial tab(s) partially and/or fully deployed (and the remaining tab(s) yet to be partially and/or fully deployed) based on the imaging or visualization. To further improve the visibility of the tabs, the length and/or curvature of one or more of the tabs may be customized for the individual patient and their anatomy. The length and/or curvature of the one or more tabs may be customized to provide an optimum fit for the individual patient's anatomy, such as the deployment area behind the valve leaflet(s) and/or the chordae tendinae.

In some embodiments, the first and second anterior tabs may be deployed concurrently. FIGS. 15A-15E schematically illustrate the deployment of a prosthetic cardiac valve 1500*a* whereby its first anterior tab A1 and its second anterior tab A2 are concurrently deployed. FIG. 15A shows a constraining sheath 1550 fully constraining the prosthetic cardiac valve 1500*a*. The prosthetic cardiac valve 1500*a* may be deployed as the constraining sheath 1550 is retracted from the atrial (ATR) side of the prosthetic cardiac valve 1500*a* to the ventricular (VEN) side. As shown in FIG. 15B, the retraction of the constraining sheath 1550 may first allow the atrial skirt 1506 of the prosthetic cardiac valve 1500 to begin to self-expand radially outward. As shown in FIG.

15C, the constraining sheath 1550 may be retracted further to concurrently release the first anterior tab A1 and the second anterior tab A2 from constraint, exposing the tabs. As shown in FIG. 15D, further retraction of the constraining sheath 1500a allows the first anterior tab A1 and the second anterior tab A2 to partially spring radially outward to be in orientations that are transverse to the longitudinal axes of the constraining sheath 1550 and prosthetic cardiac valve 1500a as described above. The first and second anterior tabs A1, A2 may have the same length and/or may be positioned on the prosthetic cardiac valve so that their atrial ends are positioned in the same axial position, hence, the retraction of the constraining sheath 1550 may expose the anterior tabs A1, A2 and/or allow the anterior tabs A1, A2 to partially deploy concurrently. As shown in FIG. 15E, the constraining sheath 1550 may be fully retracted to fully release the prosthetic cardiac valve 1500a, allowing the anterior tabs A1, A2 to fully deploy to capture the adjacent chordae tendineae and also to allow the ventricular skirt 1516 to self-expand radially outward. The posterior tab PTB of the prosthetic cardiac valve 1500, while not shown in FIGS. 15A-15E, may be configured to deploy before, concurrently with, or after the anterior tabs A1, A2.

Figure 15I:
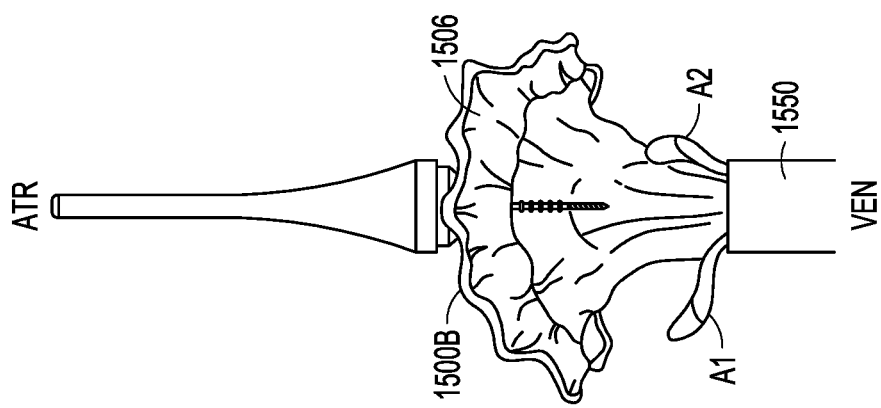
Figure 15H:
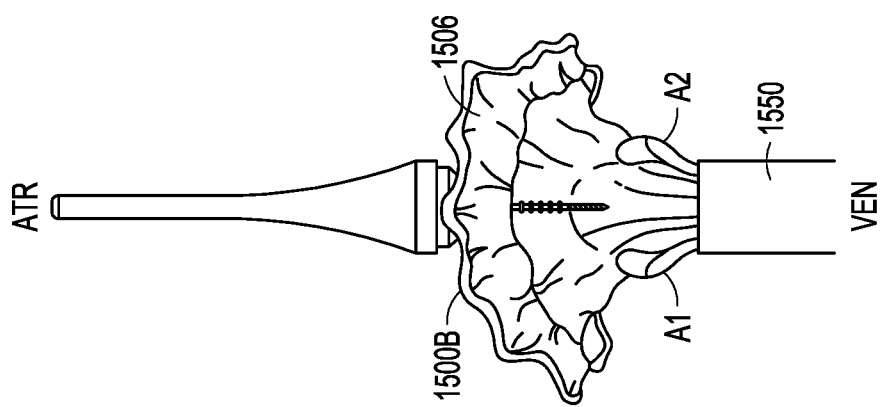
Figure 15G:
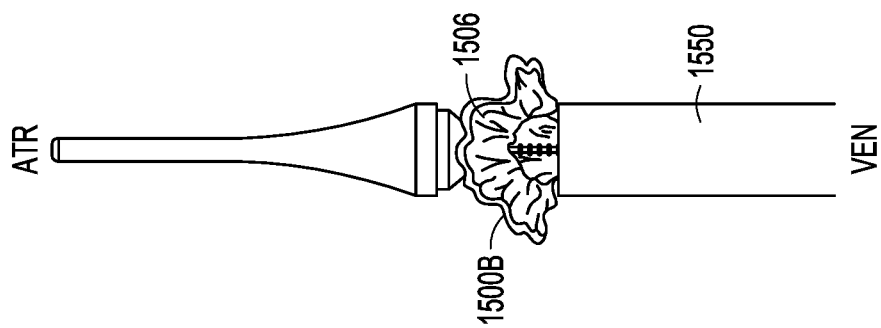
Figure 15F:
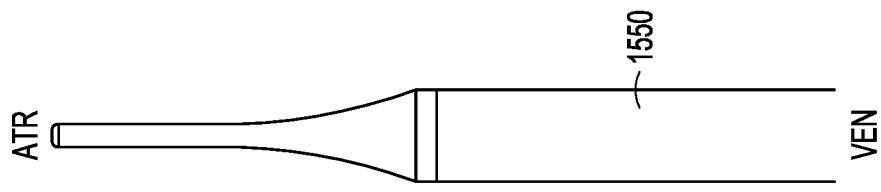

In some embodiments, the first and second anterior tabs may be deployed sequentially. FIGS. 15F-15L schematically illustrate the deployment of a prosthetic cardiac valve 1500b whereby its first anterior tab A1 and its second anterior tab A2 are sequentially deployed. FIG. 15F shows a constraining sheath 1550 fully constraining the prosthetic cardiac valve 1500b. The prosthetic cardiac valve 1500b may be deployed as the constraining sheath 1550 is retracted from the atrial (ATR) side of the prosthetic cardiac valve 1500 to the ventricular (VEN) side. As shown in FIG. 15G, the retraction of the constraining sheath 1550 may first allow the atrial skirt 1506 of the prosthetic cardiac valve 1500b to begin to self-expand radially outward. As shown in FIG. 15H, the constraining sheath 1550 may be retracted further to concurrently release the first anterior tab A1 and the second anterior tab A2 from constraint, exposing the tabs. As shown in FIG. 15I, further retraction of the constraining sheath 1550 allows the first anterior tab A1 to partially spring radially outward to be in orientations that are transverse to the longitudinal axes of the constraining sheath 1550 and prosthetic cardiac valve 1500b as described above, while the second anterior tab A2 remains in an undeployed configuration. As shown in FIG. 15I, even further retraction of the constraining sheath 1550 fully frees the first anterior tab A1 from constraint, allowing the first anterior tab A1 to fully deploy to capture adjacent chordae tendineae. As shown in FIG. 15K, subsequent retraction of the constraining sheath 1550 allows the second anterior tab A1 to partially spring radially outward to be in orientations that are transverse to the longitudinal axes of the constraining sheath 1550 and prosthetic cardiac valve 1500b as described above. As shown in FIG. 15I, even further retraction of the constraining sheath 1550 fully frees the second anterior tab A2 from constraint, allowing the second anterior tab A2 to fully deploy to capture adjacent chordae tendineae as well the ventricular skirt 1516 to self-expand radially outward. The posterior tab PTB of the prosthetic cardiac valve 1500b, while not shown in FIGS. 15F-15L, may be configured to deploy before one or both of the anterior tabs A1, A2, concurrently with one of the anterior tabs A1, A2, or after one or both of the anterior tabs A1, A2.

While FIGS. 15A-15E and FIGS. 15F-15I, show particular sequences of fully deploying the first and second anterior tabs A1, A2 and the posterior tab PTB, the first and second tabs A1, A2 and the posterior tab PTB may be configured to fully deploy in any order.

FIG. 16A shows the prosthetic cardiac valve 1500 held within the constraining sheath 1550 while FIG. 16B schematically illustrates a cross-section of the prosthetic cardiac calve 1500 taken along line B-B of FIG. 16B and showing the relative positions of the first and second tabs A1, A2 and the posterior tab PTB. For the ease of illustration in FIGS. 17A-17M, the first and second anterior tabs A1, A2 (particularly their ventricular ends), the posterior tab PTB (particularly its ventricular end), and the edges V1, V2, and V3 are show in a rolled out configuration relative to a retracting constraining sheath 1550 to show various orders of full deployment of the first and second anterior tabs A1, A2 and the posterior tab PTB.

In some embodiments, the lengths of the tabs and/or the axial positions of the free ends 1701, 1702, 1703 of the tabs may be varied such that two or more of the two anterior tabs A1, A2 and the posterior tab PTB are fully deployed concurrently.

As shown in FIG. 17A, a distal edge 1650 of the constraining sheath 1550 is arranged to retract proximally in the direction of arrow AR1 parallel to the longitudinal axis of the valve during tab deployment. In FIG. 17A, the first and second anterior tabs A1, A2 and the posterior tab PTB may all have the same length and/or have their free ends 1701, 1702, 1703 in the same axial positions. Therefore, the three tabs A1, A2, PTB are be fully deployed concurrently with one another as the distal edge 1650 of the constraining sheath 1550 retracts proximally in the direction of arrow A1 parallel to the longitudinal axis of the valve. The edges V1, V2, V3 of the ventricular skirt are closer to the annular region than the free ends 1701, 1702 1703 of the three tabs A1, A2, PTB such that, as the sheath 1550 is retracted, the ventricular skirt is configured to deploy before the tabs A1, A2, PTB finish expanding.

As shown in FIG. 17B, the distal edge 1650 of the constraining sheath 1550 is arranged to retract proximally in the direction of arrow AR1 parallel to the longitudinal axis of the valve during tab deployment. In FIG. 17B, the first and second anterior tabs A1, A2 may have the same length as each other, and the posterior tab PTB may have a greater length than the first and second anterior tabs A1, A2, and/or the free end 1703 of the posterior tab PTB may be further from the annular region than the free ends 1701, 1702 of the first and second anterior tabs A1, A2. Therefore, as the distal edge 1650 of the constraining sheath 1550 retracts proximally in the direction of arrow AR1 parallel to the longitudinal axis of the valve, the first and second anterior tabs A1, A2 are concurrently fully deployed before the posterior tab PTB is fully deployed. The edges V1, V2, V3 of the ventricular skirt are closer to the annular region than the free ends 1701, 1702, 1703 of the three tabs A1, A2, PTB such that, as the sheath 1550 is retracted, the ventricular skirt is configured to deploy before the tabs A1, A2, PTB finish expanding.

Figure 17D:
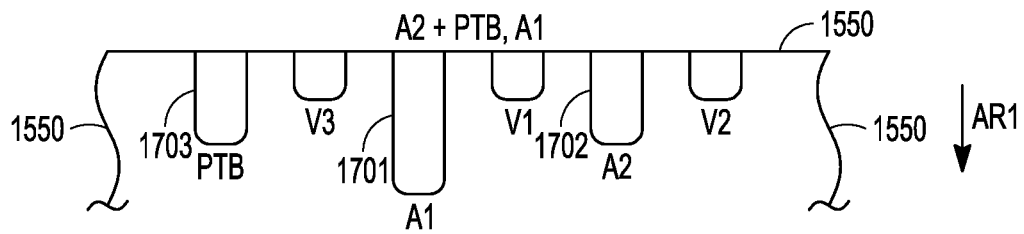
Figure 17E:
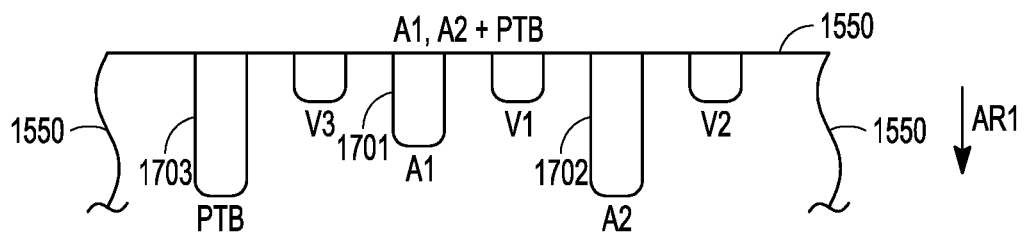
Figure 17F:
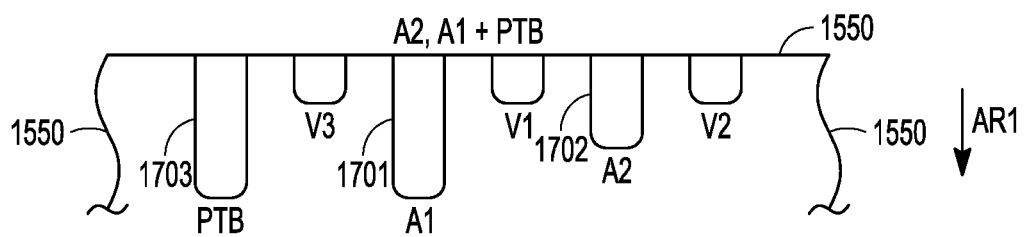
Figure 17G:
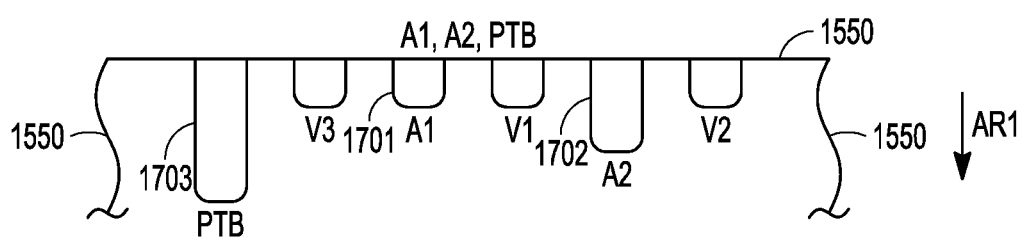
Figure 17H:
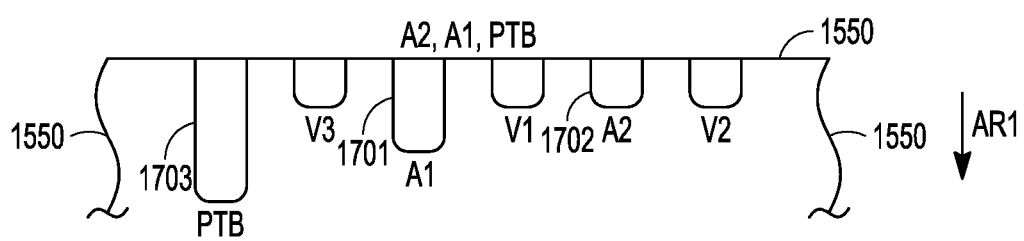
Figure 17I:
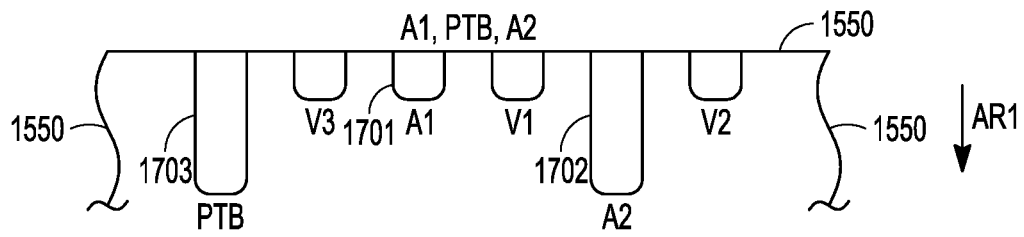
Figure 17J:
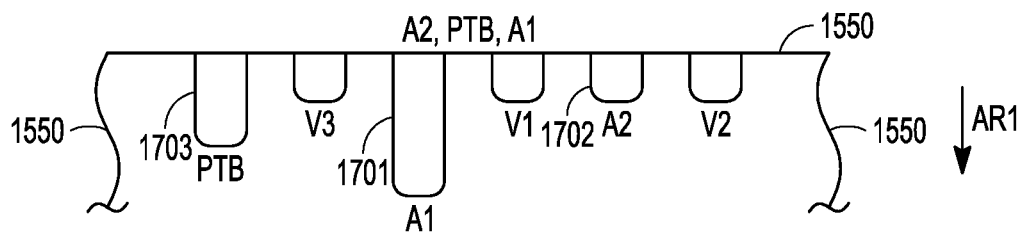
Figure 17K:
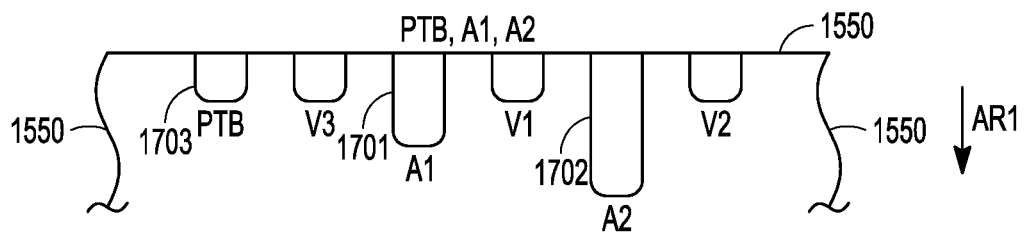
Figure 17L:
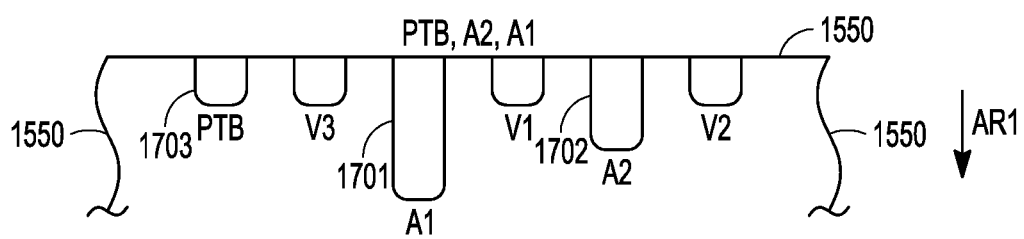
Figure 17M:
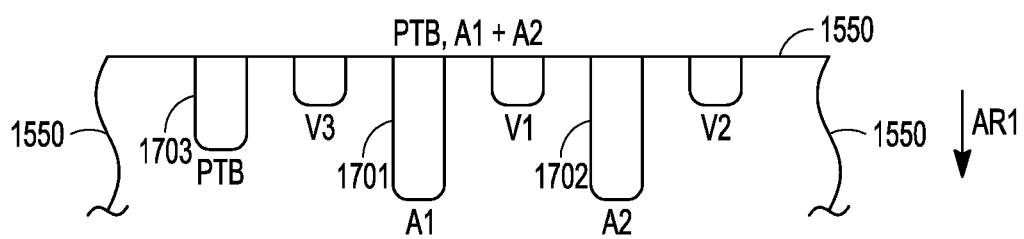

As shown in FIG. 17M (described further below), the distal edge 1650 of the constraining sheath 1550 is arranged to retract proximally in the direction of arrow AR1 parallel to the longitudinal axis of the valve during tab deployment. In FIG. 17M, the first and second anterior tabs A1, A2 may have the same length as each other, and the posterior tab PTB may have a shorter length than the first and second anterior tabs A1, A2, and/or the free end 1703 of the posterior tab PTB may be closer to the annular region than the free ends 1701, 1702 of the first and second anterior tabs A1, A2. Therefore, as the distal edge 1650 of the constraining sheath 1550 retracts proximally in the direction of arrow AR1 parallel to the longitudinal axis of the valve, the first and second anterior tabs A1, A2 are concurrently fully deployed after the posterior tab PTB is fully deployed. The edges V1, V2, V3 of the ventricular skirt are closer to the annular region than the free ends 1701, 1702, 1703 of the three tabs A1, A2, PTB such that, as the sheath 1550 is retracted, the ventricular skirt is configured to deploy before the tabs A1, 42, PTB finish expanding.

In some embodiments, the lengths of the tabs and/or the axial positions of the ventricular ends of the tabs may be varied such that one of the two anterior tabs A1, A2 may have the same length as the posterior tab PTB and/or their free ends may be in the same axial position. In this case, one of the two anterior tabs A1, A2 is fully deployed concurrently with the posterior tab PTB. The lengths of the tabs and/or the axial positions of the free ends of the tabs may be varied such that the second of the anterior tabs A1, A2 may be allowed to fully deploy before or after the concurrent full deployment of the first of the anterior tabs A1, 42 and the posterior tab PTB.

As shown in FIG. 17C, the distal edge 1650 of the constraining sheath 1550 is arranged to retract proximally in the direction of arrow AR1 parallel to the longitudinal axis of the valve during tab deployment. In FIG. 17C, the first anterior tab A1 may have the same length as the posterior tab PTB and/or their free ends 1701, 1703 may be in the same axial position. The second anterior tab A2 may have a greater length than the first anterior tab A1 and the posterior tab PTB and/or its free end 1702 may be further from the annular region than the free ends 1701, 1703 of the first anterior tab A1 and the posterior tab PTB. In this case, as the distal edge 1650 of the constraining sheath 1550 is retracted proximally in the direction of arrow AR1 parallel to the longitudinal axis of the valve, the first anterior tab A1 fully deploys concurrently with the posterior tab PTB, and the second anterior tab A2 fully deploys after them. The edges V1, V2, V3 of the ventricular skirt are closer to the annular region than the free ends 1701, 1702, 1703 of the three tabs A1, A2, PTB such that, as the sheath 1550 is retracted, the ventricular skirt is configured to deploy before the tabs A1, A2, PTB finish expanding.

As shown in FIG. 17D, the distal edge 1650 of the constraining sheath 1550 is arranged to retract proximally in the direction of arrow AR1 parallel to the longitudinal axis of the valve during tab deployment. In FIG. 17D, the second anterior tab A2 and the posterior tab PTB may have the same length as each other, as the first anterior tab A1 may have a longer length than the second anterior tab A2 and the posterior tab PTB, and/or the free ends 1702, 1703 of the second anterior tab A2 and the posterior tab PTB may be closer to the annular region than the free end 1701 of the first anterior tab A1. Therefore, as the distal edge 1650 of the constraining sheath retracts proximally in the direction of arrow AR1 parallel to the longitudinal axis of the valve, the second anterior tab A2 fully deploys concurrently with the posterior tab PTB, and the first anterior tab A1 fully deploys after. The edges V1, V2, V3 of the ventricular skirt are closer to the annular region than the free ends 1701, 1702, 1703 of the three tabs A1, A2, PTB such that, as the sheath 1550 is retracted, the ventricular skirt is configured to deploy before the tabs A1, A2, PTB finish expanding.

As shown in FIG. 17E, the distal edge 1650 of the constraining sheath 1550 is arranged to retract proximally in the direction of arrow AR1 parallel to the longitudinal axis of the valve during tab deployment. In FIG. 17E, the second anterior tab A2 and the posterior tab PTB may have the same length as each other and the first anterior tab A1 may have a shorter length than the second anterior tab A2 and the posterior tab PTB, and/or the free ends 1702, 1703 of the second anterior tab A2 and the posterior tab PTB may be further from the annular region than the free end 1701 of the first anterior tab A1. Therefore, as the distal edge 1650 of the constraining sheath retracts proximally in the direction of arrow AR1 parallel to the longitudinal axis of the valve, the first anterior tab A1 fully deploy first, followed by the second anterior tab A2 and the posterior tab PTB concurrently. The edges V1, V2, V3 of the ventricular skirt are closer to the annular region than the free ends 1701, 1702, 1703 of the three tabs A1, A2, PTB such that, as the sheath 1550 is retracted the ventricular skirt is configured to deploy before the tabs A1, A2, PTB finish expanding.

As shown in FIG. 17F, the distal edge 1650 of the constraining sheath 1550 is arranged to retract proximally in the direction of arrow AR1 parallel to the longitudinal axis of the valve during tab deployment. In FIG. 17F, the first anterior tab A1 and the posterior tab PTB may have the same length as each other and the second anterior tab A1 may have a shorter length than the first anterior tab A1 and the posterior tab PTB, and/or the free ends 1701, 1703 of the first anterior tab A1 and the posterior tab PTB may be further from the annular region than the free end 1702 of the second anterior tab A2. Therefore, as the distal edge 1650 of the constraining sheath retracts proximally in the direction of arrow AR1 parallel to the longitudinal axis of the valve, the second anterior tab A2 fully deploy first, followed by the first anterior tab A1 and the posterior tab PTB concurrently. The edges V1, V2, V3 of the ventricular skirt are closer to the annular region than the free ends 1701, 1702, 1703 of the three tabs A1, A2, PTB such that, as the sheath 1550 is retracted, the ventricular skirt is configured to deploy before the tabs A1, A2, PTB finish expanding.

In some embodiments, the lengths of the tabs and/or the axial positions of the ventricular ends of the tabs may be varied such that one of the two anterior tabs A1, A2 is fully deployed before the posterior tab PTB. The lengths of the tabs and/or the axial positions of the ventricular ends of the tabs may be varied such that the second of the anterior tabs A1, A2 may be allowed to fully deploy before or after the full deployment of the posterior tab PTB.

As shown in FIG. 17G, the distal edge 1650 of the constraining sheath 1550 is arranged to retract proximally in the direction of arrow AR1 parallel to the longitudinal axis of the valve during tab deployment. In FIG. 17G, the posterior tab PTB may be longer than the second anterior tab A2 which may be longer than the first anterior tab A1, and/or the free end 1703 of the posterior tab PTB may be further from the annular region than the free end 1702 of the second anterior tab A2 which may be further from the annular region than the free end 1701 of the first anterior tab A1. In this case, as the distal edge 1650 of the constraining sheath 1550 is retracted proximally in the direction of arrow AR1 parallel to the longitudinal axis of the valve, the first anterior tab A1 fully deploys first, followed by the second anterior tab A2, and then followed by the posterior tab PTB. The edges V1, V2, V3 of the ventricular skirt are closer to the annular region than the free ends 1701, 1702, 1703 of the three tabs A1, A2, PTB such that, as the sheath 1550 is retracted, the ventricular skirt is configured to deploy before the tabs A1, A2, PTB finish expanding.

As shown in FIG. 17H, the distal edge 1650 of the constraining sheath 1550 is arranged to retract proximally in the direction of arrow AR1 parallel to the longitudinal axis of the valve during tab deployment. In FIG. 17H, the posterior tab PTB may be longer than the first anterior tab A1 which may be longer than the second anterior tab A2, and/or the free end 1703 of the posterior tab PTB may be further from the annular region than the free end 1701 of the first anterior tab A1 which may be further from the annular region than the free end 1702 of the second anterior tab A2. In this case, as the distal edge 1650 of the constraining sheath 1550 is retracted proximally in the direction of arrow AR1 parallel to the longitudinal axis of the valve, the second anterior tab A2 fully deploy first, followed by the first anterior tab A1, and then followed by the posterior tab PTB. The edges V1, V2, V3 of the ventricular skirt are closer to the annular region than the free ends 1701, 1702, 1703 of the three tabs A1, A2, PTB such that, as the sheath 1550 is retracted, the ventricular skirt is configured to deploy before the tabs A1, A2, PTB finish expanding.

As shown in FIG. 17I, the distal edge 1650 of the constraining sheath 1550 is arranged to retract proximally in the direction of arrow AR1 parallel to the longitudinal axis of the valve during tab deployment. In FIG. 17I, the second anterior tab A2 may be longer than the posterior tab PTB which may be longer than the first anterior tab A1, and/or the free end 1702 of the second anterior tab A2 may be further from the annular region than the free end 1703 of the posterior tab PTB which may be further from the annular region than the free end 1701 of the first anterior tab. In this case, as the distal edge 1650 of the constraining sheath 1550 is retracted proximally in the direction of arrow AR1 parallel to the longitudinal axis of the valve, the first anterior tab A1 fully deploys first, followed by the posterior tab PTB, and then followed by the second anterior tab A2. The edges V1, V2, V3 of the ventricular skirt are closer to the annular region than the free ends 1701, 1702, 1703 of the three tabs A1, A2, PTB such that, as the sheath 1550 is retracted, the ventricular skirt is configured to deploy before the tabs A1, A2, PTB finish expanding.

As shown in FIG. 17J, the distal edge 1650 of the constraining sheath 1550 is arranged to retract proximally in the direction of arrow AR1 parallel to the longitudinal axis of the valve during tab deployment. In FIG. 17J, the first anterior tab A1 may be longer than the posterior tab PTB which may be longer than the second anterior tab A2, and/or the free end 1701 of the first anterior tab A1 may be further from the annular region than the free end 1703 of the posterior tab PTB which may be further from the annular region than the free end 1702 of the second anterior tab A2. In this case, as the distal edge 1650 of the constraining sheath 1550 is retracted proximally in the direction of arrow AR1 parallel to the longitudinal axis of the valve, the second anterior tab A1 fully deploys first, followed by the posterior tab PTB, and then followed by the second anterior tab A2. The edges V1, V2, V3 of the ventricular skirt are closer to the annular region than the free ends 1701, 1702, 1703 of the three tabs A1, A2, PTB such that, as the sheath 1550 is retracted, the ventricular skirt is configured to deploy before the tabs A1, A2, PTB finish expanding.

In some embodiments, the lengths of the tabs and/or the axial positions of the ventricular ends of the tabs may be varied such that the posterior tab PTB is fully deployed first. The lengths of the tabs and/or the axial positions of the ventricular ends of the tabs may be varied such that the anterior tabs A1, A2 fully deploy either sequentially or concurrently after the full deployment of the posterior tab PTB.

As shown in FIG. 17K, the distal edge 1650 of the constraining sheath 1550 is arranged to retract proximally in the direction of arrow AR1 parallel to the longitudinal axis of the valve during tab deployment. In FIG. 17K, the second anterior tab A2 may be longer than the first anterior tab A1 which may be longer than the posterior tab PTB, and/or the free end 1702 of the second anterior tab A2 may be further from the annular region than the free end 1701 of the first anterior tab A1 which may be further from the annular region than the free end 1703 of the posterior tab PTB. In this case, as the distal edge 1650 of the constraining sheath 1550 is retracted proximally in the direction of arrow AR1 parallel to the longitudinal axis of the valve, the posterior tab PTB fully deploys first, followed by the first anterior tab A1 and then the second anterior tab A2. The edges V1, V2, V3 of the ventricular skirt are closer to the annular region than the free ends 1701, 1702, 1703 of the three tabs A1, A2, PTB such that, as the sheath 1550 is retracted, the ventricular skirt is configured to deploy before the tabs A1, A2, PTB finish expanding.

As shown in FIG. 17I, the distal edge 1650 of the constraining sheath 1550 is arranged to retract proximally in the direction of arrow AR1 parallel to the longitudinal axis of the valve during tab deployment. In FIG. 17L, the first anterior tab A1 may be longer than the second anterior tab A2 which may be longer than the posterior tab PTB, and/or the free end 1701 of the first anterior tab A1 may be further from the annular region than the free end 1702 of the second anterior tab A2 which may be further from the annular region than the free end 1703 of the posterior tab PTB. In this case, as the distal edge 1650 of the constraining sheath 1550 is retracted proximally in the direction of arrow AR1 parallel to the longitudinal axis of the valve, the posterior tab PTB fully deploys first, followed by the second anterior tab A1 and then the first anterior tab A2. The edges V1, V2, V3 of the ventricular skirt are closer to the annular region than the free ends 1701, 1702. 1703 of the three tabs A1, A2, PTB such that, as the sheath 1550 is retracted, the ventricular skirt is configured to deploy before the tabs A1, A2, PTB finish expanding.

As shown in FIG. 17M, the distal edge 1650 of the constraining sheath 1550 is arranged to retract proximally in the direction of arrow AR1 parallel to the longitudinal axis of the valve during tab deployment. In FIG. 17M, the first anterior tab A1 and the second anterior tab A2 may have the same length and both may be longer than the posterior tab PTB, and/or the free end 1701 of the first anterior tab A1 and the free end 1702 of the second anterior tab A2 may be the same distance from the annular region and both may be further from the annular region than the free end 1703 of the posterior tab. In this case, the posterior tab PTB fully deploys first, followed by the first anterior tab A1 and the second anterior tab A2 concurrently. The edges V1, V2, V3 of the ventricular skirt are closer to the annular region than the free ends 1701, 1702, 1703 of the three tabs A1 before the tabs A1, A2, PTB finish expanding.

While FIGS. 17A-17M show the ventricular skirt (and its edges V1, V2, V3) deploying concurrently with the first deployed tab or before any of the tabs, the ventricular skirt may be configured to deploy in any order, for example, before any combination of the tabs, after any combination of the tabs, and/or concurrently with any of the tabs. One or more of the sides V1, V2, and V3 may deploy before the remaining sides.

As described above and herein, the anterior and posterior tabs may partially deploy upon retraction of the constraining sheath 1550, such as to deploy to an orientation transverse to the longitudinal axes of the prosthetic cardiac valve and the constraining sheath. This partially deployed position of the tabs may position the tabs relative to one or more of the anterior leaflet AL, the posterior leaflet PL, or the adjacent chordae tendinae for subsequent engagement and capture by the tabs upon full deployment. One or more of the partially deployed anterior or posterior tabs may be visualized to confirm proper positioning and/or orientation of the prosthetic cardiac valve and its tabs. If needed, the prosthetic valve may be repositioned and/or reoriented with the initial tab(s) deployed (and the remaining tab(s) yet to be deployed) based on the imaging or visualization. In response to the visualization, the prosthetic cardiac valve may be repositioned and/or reoriented. The anterior and posterior tabs may partially deploy in any order and in any combination with any order of the full deployment of the tabs as described above with respect to FIGS. 17A-17B. For the ease of illustration in the following described FIGS. 18A-18M the first and second anterior tabs A1, A2 (particularly their atrial ends 1801, 1802) and the posterior tab PTB (particularly its atrial end 1803) are show in a rolled out configuration relative to a retracting constraining sheath 1550 to show various orders of partial deployment of the first and second anterior tabs A1, A2 and the posterior tab PTB.

In some embodiments, the lengths of the tabs and/or the axial positions of the atrial ends of the tabs may be varied such that two or more of the two anterior tabs A1, A2 and the posterior tab PTB are partially deployed concurrently.

Figure 18A:
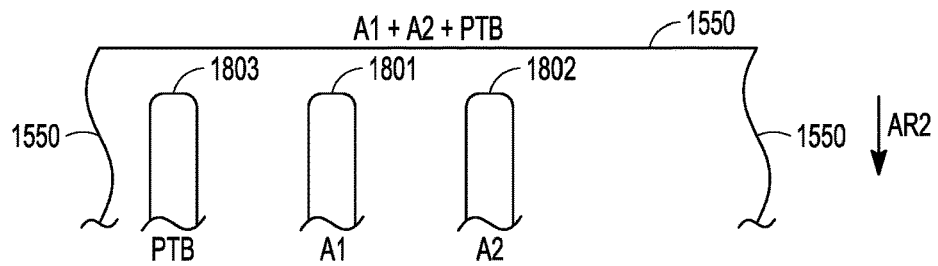
FIGS. 18A-18M schematically illustrate variations of different sequences for partially deploying a first anterior tab, a second anterior tab, and a posterior tab of a prosthetic cardiac valve, according to many embodiments.

As shown in FIG. 18A, the distal edge 1650 of the constraining sheath 1550 is arranged to retract proximally in the direction of arrow AR2 parallel to the longitudinal axis of the valve during tab deployment. In FIG. 18A, the first and second anterior tabs A1, A2 and the posterior tab PTB may have the same lengths, and/or their atrial ends 1801, 1802, 1803 may be in the same axial position away from the annular region. The first and second anterior tabs A1, A2 and the posterior tab PTB will partially deploy concurrently with one another as the constraining sheath 1550 is retracted.

Figure 18B:
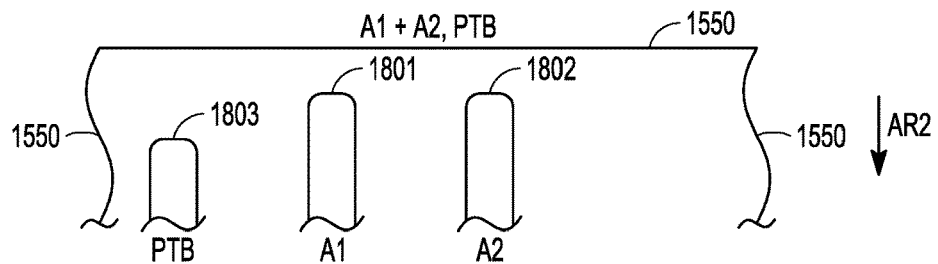

As shown in FIG. 18B, the distal edge 1650 of the constraining sheath 1550 is arranged to retract proximally in the direction of arrow AR2 parallel to the longitudinal axis of the valve during tab deployment. In FIG. 18B, the first and second anterior tabs A1, A2 may have the same lengths and both may be longer than the posterior tab PTB, and/or the atrial ends 1801, 1802 of both the first and second anterior tabs A1, A2 may be in the same axial position away from the annular region and both may be further from the annular region than the atrial end 1803 of the posterior tab PTB. The first and second anterior tabs A1, A2 will concurrently partially deploy before the posterior tab PTB is partially deployed as the constraining sheath 1550 is retracted.

Figure 18C:
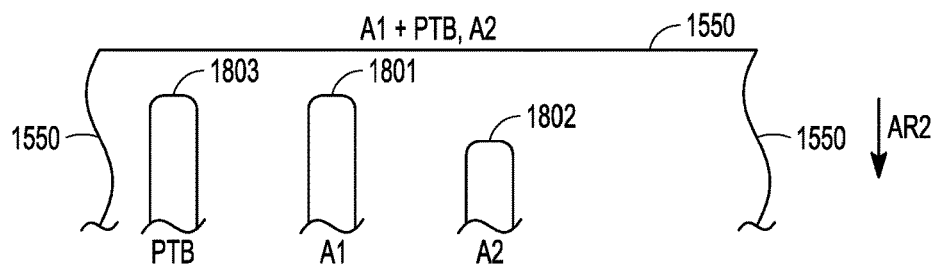
Figure 18D:
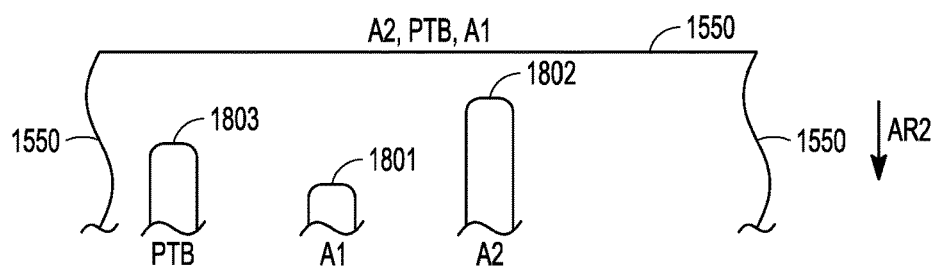
Figure 18E:
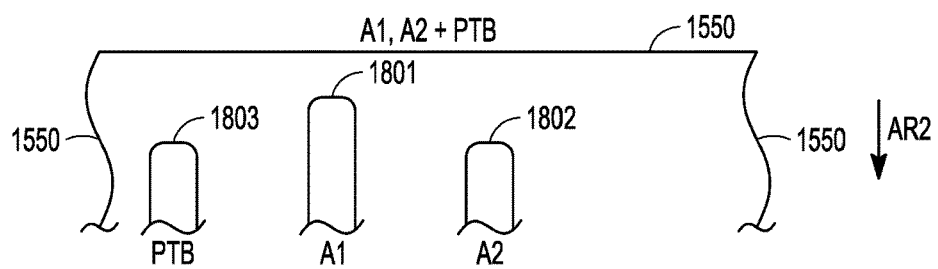
Figure 18F:
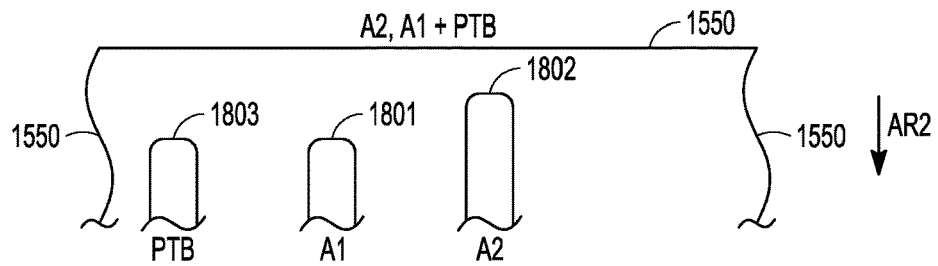
Figure 18G:
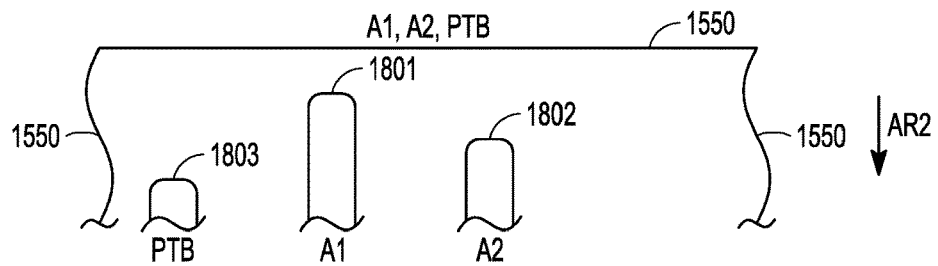
Figure 18H:
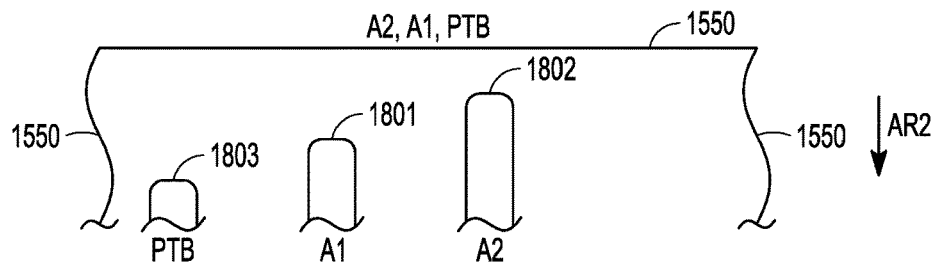
Figure 18I:
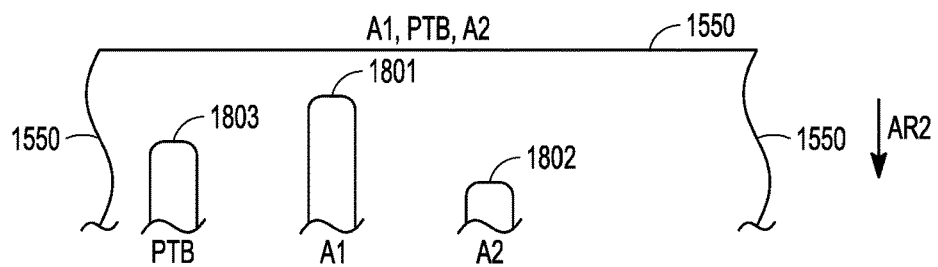
Figure 18J:
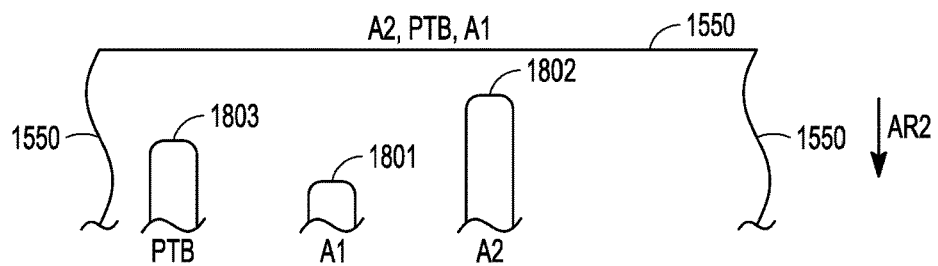
Figure 18K:
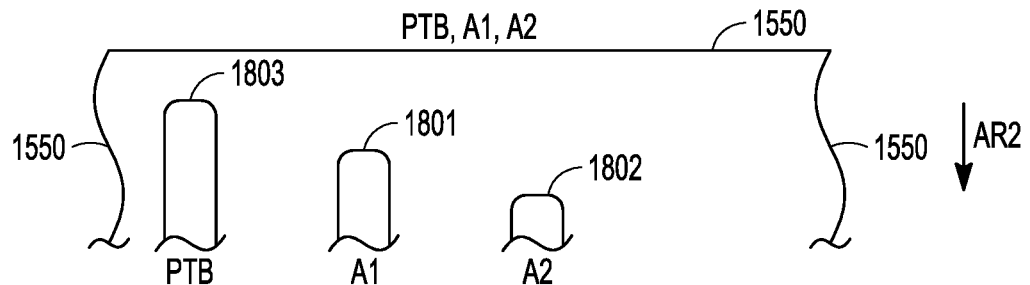
Figure 18L:
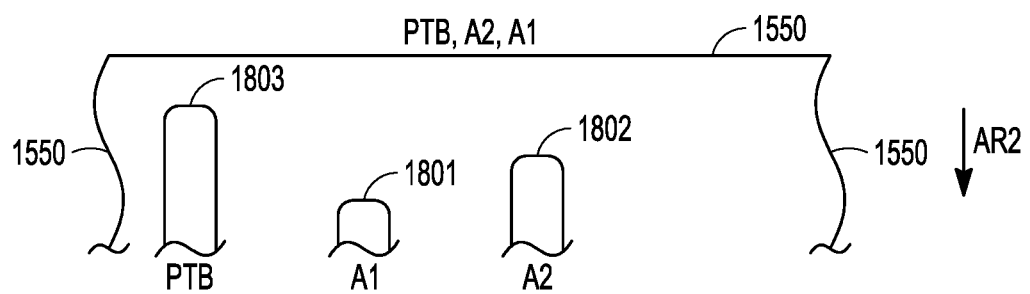
Figure 18M:
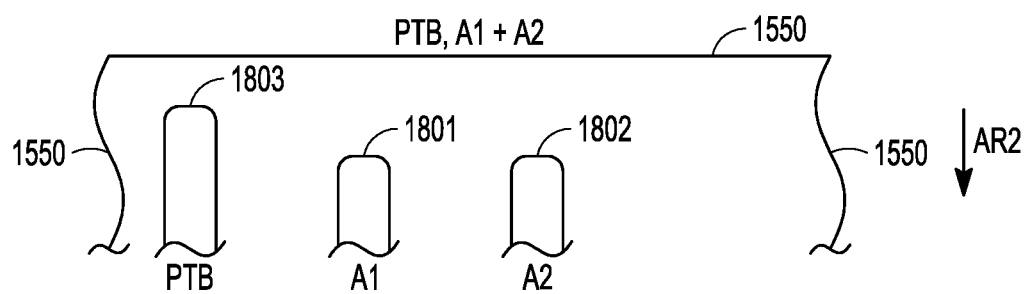

As shown in FIG. 18M (described further below), the distal edge 1650 of the constraining sheath 1550 is arranged to retract proximally in the direction of arrow AR2 parallel to the longitudinal axis of the valve during tab deployment. In FIG. 18M, the first and second anterior tabs A1, A2 may have the same lengths and both may be shorter than the posterior tab PTB, and/or the atrial ends 1801, 1802 of both the first and second anterior tabs A1, A2 may be in the same axial position away from the annular region and both may be closer to the annular region than the atrial end 1803 of the posterior tab PTB. The first and second anterior tabs A1, A2 will concurrently partially deploy after the posterior tab PTB is partially deployed as the constraining sheath 1550 is retracted.

In some embodiments, the lengths of the tabs and/or the axial positions of the atrial ends of the tabs may be varied such that one of the two anterior tabs A1, A2 is partially deployed concurrently with the posterior tab PTB. The lengths of the tabs and/or the axial positions of the atrial ends of the tabs may be varied such that the second of the anterior tabs A1, A2 may be allowed to partially deploy before or after the concurrent partial deployment of the first of the anterior tabs A1, A2 and the posterior tab PTB.

As shown in FIG. 18C, the distal edge 1650 of the constraining sheath 1550 is arranged to retract proximally in the direction of arrow AR2 parallel to the longitudinal axis of the valve during tab deployment. In FIG. 18C, the first anterior tab A1 and the posterior tab PTB may have the same lengths and both may be longer than the second anterior tab A2, and/or the atrial ends 1801, 1803 of both the first anterior tab A1 and posterior tab PTB may be in the same axial position away from the annular region and both may be further from the annular region than the atrial end 1802 of the second anterior tab A2. The first anterior tab A1 will partially deploy concurrently with the posterior tab PTB and the second anterior tab A2 will partially deploys after as the constraining sheath 1550 is retracted.

As shown in FIG. 18D, the distal edge 1650 of the constraining sheath 1550 is arranged to retract proximally in the direction of arrow AR2 parallel to the longitudinal axis of the valve during tab deployment. In FIG. 18D, the second anterior tab A2 may be longer than the posterior tab PTB which may be longer than the first anterior tab A1, and/or the atrial end 1802 of the second anterior tab A2 may be in an axial position further from the annular region than the atrial end 1803 of the posterior tab PTB which may be in an axial position further from the annular region than the atrial end 1801 of the first anterior tab A1. The second anterior tab A2 will partially deploy concurrently with the posterior tab PTB and the first anterior tab A1 will partially deploy after as the constraining sheath 1550 is retracted.

As shown in FIG. 18E, the distal edge 1650 of the constraining sheath 1550 is arranged to retract proximally in the direction of arrow AR2 parallel to the longitudinal axis of the valve during tab deployment. In FIG. 18E, the second anterior tab A2 and the posterior tab PTB may have the same length and both may be shorter than the first anterior tab A1, and/or the atrial ends 1802, 1803 of the second anterior tab A2 and the posterior tab PTB may be in the same axial positions away from the annular region which are closer to the annular region than the atrial end 1801 of the first anterior tab A1. The first anterior tab A1 will partially deploy first, followed by the second anterior tab A2 and the posterior tab PTB concurrently, as the constraining sheath 1550 is retracted.

As shown in FIG. 18F, the distal edge 1650 of the constraining sheath 1550 is arranged to retract proximally in the direction of arrow AR2 parallel to the longitudinal axis of the valve during tab deployment. In FIG. 18I, the first anterior tab A1 and the posterior tab PTB may have the same length and both may be shorter than the second anterior tab A1, and/or the atrial ends 1801, 1803 of the first anterior tab A1 and the posterior tab PTB may be in the same axial positions away from the annular region which are closer to the annular region than the atrial end 1802 of the second anterior tab A2. The second anterior tab A2 will partially deploy first, followed by the first anterior tab A1 and the posterior tab PTB concurrently, as the constraining sheath 1550 is retracted.

In some embodiments, the lengths of the tabs and/or the axial positions of the atrial ends of the tabs may be varied such that one of the two anterior tabs A1, A2 is partially deployed before the posterior tab PTB. The lengths of the tabs and/or the axial positions of the atrial ends of the tabs may be varied such that the second of the anterior tabs A1, A2 may be allowed to partially deploy before or after the full deployment of the posterior tab PTB.

As shown in FIG. 18G, the distal edge 1650 of the constraining sheath 1550 is arranged to retract proximally in the direction of arrow AR2 parallel to the longitudinal axis of the valve during tab deployment. In FIG. 18G, the first anterior tab A1 may be longer than the second anterior tab A2 which may be longer than the posterior tab PTB, and/or the atrial end 1801 of the first anterior tab A1 may be in an axial position away from the annular region further than the atrial end 1802 of the second anterior tab A2 which may be in an axial position further from the annular region than the atrial end 1803 of the posterior tab PTB. The first anterior tab A1 will partially deploy first, followed by the second anterior tab A2, and then followed by the posterior tab PTB, as the constraining sheath 1550 is retracted.

As shown in FIG. 18H, the distal edge 1650 of the constraining sheath 1550 is arranged to retract proximally in the direction of arrow AR2 parallel to the longitudinal axis of the valve during tab deployment. In FIG. 18H, the second anterior tab A2 may be longer than the first anterior tab A1 which may be longer than the posterior tab PTB, and/or the atrial end 1802 of the second anterior tab A2 may be in an axial position away from the annular region further than the atrial end 1801 of the first anterior tab A1 which may be in an axial position further from the annular region than the atrial end 1803 of the posterior tab PTB. The second anterior tab A2 will partially deploy first, followed by the first anterior tab A1, and then followed by the posterior tab PTB, as the constraining sheath 1550 is retracted.

As shown in FIG. 18I, the distal edge 1650 of the constraining sheath 1550 is arranged to retract proximally in the direction of arrow AR2 parallel to the longitudinal axis of the valve during tab deployment. In FIG. 18I, the first anterior tab A1 may be longer than the posterior tab PTB which may be longer than the second anterior tab A2, and/or the atrial end 1801 of the first anterior tab A1 may be in an axial position away from the annular region further than the atrial end 1803 of the posterior tab PTB which may be in an axial position further from the annular region than the atrial end 1802 of the second anterior tab A2. The first anterior tab A1 will partially deploy first, followed by the posterior tab PTB, and then followed by the second anterior tab A2, as the constraining sheath 1550 is retracted.

As shown in FIG. 18J, the distal edge 1650 of the constraining sheath 1550 is arranged to retract proximally in the direction of arrow AR2 parallel to the longitudinal axis of the valve during tab deployment. In FIG. 18J, the second anterior tab A2 may be longer than the posterior tab PTB which may be longer than the first anterior tab A1, and/or the atrial end 1802 of the second anterior tab A2 may be in an axial position away from the annular region further than the atrial end 1803 of the posterior tab PTB which may be in an axial position further from the annular region than the atrial end 1801 of the first anterior tab A1. The second anterior tab A1 will partially deploy first, followed by the posterior tab PTB, and then followed by the second anterior tab A2, as the constraining sheath 1550 is retracted.

In some embodiments, the lengths of the tabs and/or the axial positions of the atrial ends of the tabs may be varied such that the posterior tab PTB is partially deployed first. The lengths of the tabs and/or the axial positions of the atrial ends of the tabs may be varied such that the anterior tabs A1, A2 partially deploy either sequentially or concurrently after the partial deployment of the posterior tab PTB.

As shown in FIG. 18K, the distal edge 1650 of the constraining sheath 1550 is arranged to retract proximally in the direction of arrow AR2 parallel to the longitudinal axis of the valve during tab deployment. In FIG. 18K, the posterior tab PTB may be longer than the first anterior tab A1 which may be longer than the second anterior tab A2, and/or the atrial end 1803 of the posterior tab PTB may be in an axial position away from the annular region further than the atrial end 1801 of the first anterior tab A1 which may be in an axial position further from the annular region than the atrial end 1802 of the second anterior tab A2. The posterior tab PTB will partially deploy first, followed by the first anterior tab A1 and then the second anterior tab A2, as the constraining sheath 1550 is retracted.

As shown in FIG. 18L, the distal edge 1650 of the constraining sheath 1550 is arranged to retract proximally in the direction of arrow AR2 parallel to the longitudinal axis of the valve during tab deployment. In FIG. 18L, the posterior tab PTB may be longer than the second anterior tab A2 which may he longer than the first anterior tab A1, and/or the atrial end 1803 of the posterior tab PTB may be in an axial position away from the annular region further than the atrial end 1802 of the second anterior tab A2 which may be in an axial position further from the annular region than the atrial end 1801 of the first anterior tab A1. The posterior tab PTB will partially deploy first, followed by the second anterior tab A1 and then the first anterior tab A2, as the constraining sheath 1550 is retracted.

As shown in FIG. 18M, the distal edge 1650 of the constraining sheath 1550 is arranged to retract proximally in the direction of arrow AR2 parallel to the longitudinal axis of the valve during tab deployment. In FIG. 18M, the posterior tab PTB may be longer than the second anterior tab A2 which may the same length as the first anterior tab A1, and/or the atrial end 1803 of the posterior tab PTB may he in an axial position away from the annular region further than the atrial ends 1801, 1802 of the first anterior tab A1 and second anterior tab A2 which may be in the same axial positions from the annular region. The posterior tab PTB will partially deploy first, followed by the first anterior tab A1 and the second anterior tab A2 concurrently, as the constraining sheath 1550 is retracted.

The first and second anterior tabs A1, A2 and the posterior tab PTB may all partially deploy before any of the same tabs concurrently deploy. Alternatively, one or more of the first and second anterior tabs A1, A2 and the posterior tab PTB may partially deploy before one or more of the first and second anterior tabs A1, A2 and the posterior tab PTB fully deploys.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of delivering an implantable prosthetic valve to a patient's heart, the patient's heart having a mitral valve with an anterior leaflet and a posterior leaflet, said method comprising:

providing a prosthetic valve, wherein the prosthetic valve comprises an expandable frame having a first end, a second end opposite the first end, a first anterior tab on an anterior portion of the expandable frame, a posterior tab on a posterior portion of the expandable frame, and a ventricular skirt adjacent the first end of the expandable frame, and wherein the prosthetic valve has an expanded configuration for engaging the heart and a collapsed configuration;

delivering the prosthetic valve in the collapsed configuration to the patient's heart adjacent the mitral valve;

expanding the first anterior tab radially outward such that a tip portion of the first anterior tab engages a first fibrous trigone on a first side of the anterior leaflet of the mitral valve, and wherein the anterior leaflet and adjacent anterior chordae tendinae are disposed between the first anterior tab and an outer anterior surface of the ventricular skirt;

prior to radially expanding the first anterior tab, radially expanding the posterior tab outward such that the posterior leaflet of the mitral valve and adjacent posterior chordae tendinae are disposed between the posterior tab and an outer posterior surface of the ventricular skirt; and radially expanding the ventricular skirt outward thereby engaging the anterior and posterior leaflets, wherein the anterior leaflet and the adjacent anterior chordae tendinae are captured between the first anterior tab and the outer anterior surface of the ventricular skirt, and wherein the posterior leaflet and the adjacent posterior chordae tendinae are captured between the posterior tab and the posterior outer surface of the ventricular skirt.

2. The method of claim 1, wherein the prosthetic valve further comprises a second anterior tab on the anterior portion of the expandable frame, the method further comprising expanding the second anterior tab radially outward such that a tip portion of the second anterior tab engages a second fibrous trigone on a second side of the anterior leaflet opposite the first side of the anterior leaflet, and wherein the anterior leaflet and adjacent anterior chordae tendinae are disposed between the second anterior tab and an outer surface of the ventricular skirt.

3. The method of claim 2, wherein the second anterior tab is radially expanded outward after the first anterior tab and the posterior tab are radially expanded outward.

4. The method of claim 2, wherein the second anterior tab is radially expanded outward before the first anterior tab and the posterior tab are radially expanded outward.

5. The method of claim 2, wherein the second anterior tab is radially expanded outward before the first anterior tab is radially expanded outward and after the posterior tab is radially expanded outward.

6. The method of claim 2, wherein radially expanding the second anterior tab outward comprises retracting a constraining sheath from the second anterior tab so that the second anterior tab is free to self-expand radially outward.

7. The method of claim 2, wherein the ventricular skirt is radially expanded outward before the second anterior tab is radially expanded outward.

8. The method of claim 2, wherein the ventricular skirt is radially expanded outward after the second anterior tab is radially expanded outward.

9. The method of claim 2, wherein the ventricular skirt is radially expanded outward concurrently with the second anterior tab being radially expanded outward.

10. The method of claim 2, further comprising, prior to the anterior leaflet and the adjacent anterior chordae tendineae being disposed between the second anterior tab and the outer anterior surface of the ventricular skirt, partially expanding the second anterior tab radially outward such that the first anterior tab is transverse to a longitudinal axis of the prosthetic valve.

11. The method of claim 10, wherein partially expanding the second anterior tab radially outward comprises partially retracting a constraining sheath from the second anterior tab so that the second anterior tab is partially free to self-expand radially outward.

12. The method of claim 1, further comprising, prior to the anterior leaflet and the adjacent anterior chordae tendineae being disposed between the first anterior tab and the outer anterior surface of the ventricular skirt, partially expanding the first anterior tab radially outward such that the first anterior tab is transverse to a longitudinal axis of the prosthetic valve.

13. The method of claim 12, wherein partially expanding the first anterior tab radially outward comprises partially retracting a constraining sheath from the first anterior tab so that the first anterior tab is partially free to self-expand radially outward.

14. The method of claim 1, further comprising, prior to disposing the posterior leaflet of the mitral valve and the adjacent posterior chordae tendineae between the posterior tab and the outer posterior surface of the ventricular skirt, partially expanding the posterior tab radially outward such that the posterior tab is transverse to a longitudinal axis of the posterior valve.

15. The method of claim 14, wherein partially expanding the posterior tab radially outward comprises partially retracting a constraining sheath from the posterior tab so that the posterior tab is partially free to self-expand radially outward.

16. The method of claim 1, wherein the ventricular skirt is radially expanded outward before the first anterior tab and posterior tab are radially expanded outward.

17. The method of claim 1, wherein the ventricular skirt is radially expanded outward after the first anterior tab and posterior tab are radially expanded outward.

18. The method of claim 1, wherein the ventricular skirt is radially expanded outward before the first anterior tab is radially expanded and after the posterior tab is radially expanded outward.

19. The method of claim 1, wherein the ventricular skirt is radially expanded outward concurrently with the first anterior tab.

20. The method of claim 1, wherein the ventricular skirt is radially expanded outward concurrently with the posterior tab.

21. The method of claim 1, wherein expanding the first anterior tab comprises retracting a constraining sheath from the first anterior tab so that the first anterior tab is free to self-expand radially outward.

22. The method of claim 1, wherein expanding the posterior tab comprises retracting a constraining sheath from the posterior tab so that the posterior tab is free to self-expand radially outward.

23. The method of claim 1, wherein radially expanding the ventricular skirt comprises retracting a constraining sheath from the ventricular skirt so that the ventricular skirt is free to self-expand radially outward.

24. The method of claim 1, further comprising providing a delivery catheter, wherein the prosthetic valve is releasably coupled thereto.

25. The method of claim 1, wherein delivering the prosthetic valve comprises transapically delivering the prosthetic valve from a region outside the heart to the left ventricle of the heart.

26. The method of claim 1, wherein delivering the prosthetic valve comprises transseptally delivering the prosthetic valve from the right atrium to the left atrium of the body.

27. The method of claim 1, wherein delivering the prosthetic valve comprises positioning the prosthetic valve across the mitral valve so that the first end of the expandable frame is inferior to a portion of the mitral valve and the second end of the expandable frame is superior to a position of the mitral valve.

28. The method of claim 1, wherein the ventricular skirt comprises a plurality of barbs, and wherein expanding the ventricular skirt comprises anchoring the plurality of barbs into heart tissue.

29. The method of claim 1, wherein the prosthetic valve further comprises a plurality of commissures, and wherein expanding the ventricular skirt displaces the anterior and posterior mitral valve leaflets radially outward thereby preventing interference between the commissures and both of the anterior and posterior leaflets.

30. The method of claim 1, wherein expanding the ventricular skirt displaces the anterior and posterior valve leaflets radially outward without contacting an inner wall of the left ventricle, and without obstructing a left ventricular outflow tract.

31. The method of claim 1, wherein radially expanding the ventricular skirt expands the ventricular skirt asymmetrically such that an anterior portion of the ventricular skirt is substantially flat, and a posterior portion of the ventricular skirt is cylindrically shaped.

32. The method of claim 1, further comprising reducing or eliminating mitral regurgitation.

33. The method of claim 1, wherein the prosthetic valve carries a therapeutic agent, and the method further comprises eluting the therapeutic agent from the prosthetic valve into adjacent tissue.

34. The method of claim 1, wherein the prosthetic valve comprises an alignment element, and wherein a second fibrous trigone is disposed on a second side of the anterior leaflet opposite the first side of the anterior leaflet, the method further comprising aligning the alignment element with an aortic root and disposing the alignment element between the first and second fibrous trigones.

35. The method of claim 34, wherein aligning the alignment element comprises rotating the prosthetic valve.

36. The method of claim 1, wherein the prosthetic valve further comprises a plurality of commissures with a covering disposed thereover whereby a plurality of prosthetic valve leaflets are formed, the method further comprising releasing the plurality of prosthetic valve leaflets from a delivery catheter.

37. The method of claim 36, wherein the plurality of prosthetic valve leaflets form a tricuspid valve, the tricuspid valve having an open configuration and a closed configuration, wherein the plurality of prosthetic valve leaflets are disposed away from one another in the open configuration thereby permitting antegrade blood flow therethrough, and wherein the plurality of prosthetic valve leaflets engage one another in the closed configuration thereby substantially preventing retrograde blood flow therethrough.

38. The method of claim 1, wherein the prosthetic valve further comprises an atrial skirt, the method further comprising:
    expanding the atrial skirt radially outward so as to lie over a superior surface of the mitral valve; and engaging the atrial skirt against the superior surface of the mitral valve.

39. The method of claim 38, wherein expanding the atrial skirt comprises retracting a constraining sheath from the atrial skirt so that the atrial skirt is free to self-expand radially outward.

40. The method of claim 38, further comprising moving the prosthetic valve upstream or downstream relative to the mitral valve to ensure that the atrial skirt engages the superior surface of the mitral valve.

41. The method of claim 38, wherein engaging the atrial skirt against the superior surface seals the atrial skirt against the superior surface of the mitral valve to prevent or substantially prevent blood flow therebetween.

42. The method of claim 1, wherein the prosthetic valve further comprises an annular region, the method further comprising:
    expanding the annular region radially outward so as to cover an annulus of the mitral valve.

43. The method of claim 42, wherein expanding the annular region comprises retracting a constraining sheath from the annular region so that the annular region is free to self-expand radially outward.

44. The method of claim 42, wherein expanding the annular region comprises asymmetrically expanding the annular region such that an anterior portion of the annular region is substantially flat, and a posterior portion of the annular region is cylindrically shaped.

* * * * *

UNITED STATES PATENT AND TRADEMARK OFFICE
CERTIFICATE OF CORRECTION

| | | |
|---|---|---|
| PATENT NO. | : 10,856,984 B2 | Page 1 of 3 |
| APPLICATION NO. | : 16/111898 | |
| DATED | : December 8, 2020 | |
| INVENTOR(S) | : Lane et al. | |

It is certified that error appears in the above-identified patent and that said Letters Patent is hereby corrected as shown below:

On the Title Page

On page 3, in Column 2, Item (56) under "Foreign Patent Documents", Line 44, delete "1458301" and insert --1458313-- therefor In the Specification In Column 2, Line 1, delete "stale" and insert --state-- therefor In Column 3, Line 4, delete "Solent," and insert --Solem,-- therefor In Column 5, Line 10, delete "leaflet, in" and insert --leaflet. In-- therefor In Column 6, Line 43, delete "minal" and insert --mitral-- therefor In Column 11, Line 63, delete "tract, in" and insert --tract. In-- therefor In Column 12, Line 41, delete "mitred" and insert --mitral-- therefor In Column 12, Line 50, delete "m" and insert --an-- therefor In Column 13, Line 4, delete "he" and insert --be-- therefor In Column 14, Line 21, after "tabs", insert --,--

In Column 14, Line 46, delete "tract, in" and insert --tract. In-- therefor

In Column 14, Line 53, delete "catty" and insert --carry-- therefor

In Column 17, Line 35, delete "tale" and insert --the-- therefor

Signed and Sealed this
Ninth Day of November, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,856,984 B2

In Column 18, Line 30, delete "he" and insert --be-- therefor

In Column 27, Line 19, delete "constrainimg" and insert --constraining-- therefor In Column 28, Line 13, delete "PTFE" and insert --ePTFE-- therefor In Column 31, Line 50, before "toward", insert --(--

In Column 34, Line 5, delete "ePTEE," and insert --ePTFE,-- therefor

In Column 35, Line 5, delete "1500a" and insert --1550-- therefor

In Column 35, Line 47, delete "FIG. 15I," and insert --FIG. 15J,-- therefor

In Column 35, Line 52, delete "A1" and insert --A2-- therefor

In Column 35, Line 56, delete "FIG. 15I," and insert --FIG. 15L,-- therefor

In Column 35, Line 66, delete "FIGS. 15F-15I," and insert --FIGS. 15F-15L-- therefor In Column 36, Line 31, delete "A1" and insert --AR1-- therefor In Column 36, Line 34, after "1702", insert --,--

In Column 37, Line 10, delete "42," and insert --A2,-- therefor

In Column 37, Line 21, delete "42" and insert --A2-- therefor

In Column 38, Line 15, after "retracted", insert --,--

In Column 38, Line 22, delete "A1" and insert --A2-- therefor

In Column 39, Line 51, delete "A1" and insert --A2-- therefor

In Column 40, Line 19, delete "FIG. 17I," and insert --FIG. 17L,-- therefor

In Column 40, Line 33, delete "A1" and insert --A2-- therefor

In Column 40, Line 33, delete "A2." and insert --A1.-- therefor

In Column 40, Line 35, delete "1702." and insert --1702,-- therefor

In Column 40, Line 53, delete "A1" and insert --A1, A2, PTB such that, as the sheath 1550 is retracted, the ventricular skirt is configured to deploy--

In Column 41, Lines 16-17, after "FIGS. 18A-18M", insert --,--

CERTIFICATE OF CORRECTION (continued)
U.S. Pat. No. 10,856,984 B2

In Column 42, Line 53, delete "FIG. 18I," and insert --FIG. 18F,-- therefor

In Column 42, Line 56, delete "A1," and insert --A2,-- therefor

In Column 43, Line 58, delete "A1" and insert --A2-- therefor

In Column 44, Line 15, delete "FIG. 18I," and insert --FIG. 18L,-- therefor

In Column 44, Line 27, delete "A1" and insert --A2-- therefor

In Column 44, Line 27, delete "A2," and insert --A1,-- therefor

In Column 44, Line 35, delete "he" and insert --be-- therefor